United States Patent
Becker et al.

(10) Patent No.: US 9,156,862 B2
(45) Date of Patent: Oct. 13, 2015

(54) SILYLATED AZULENYL NITRONE SPIN TRAPS AS CHROMOTROPIC SUPEROXIDE DETECTORS

(71) Applicant: THE FLORDIA INTERNATIONAL UNIVERSITY BOARD OF TRUSTEES, Miami, FL (US)

(72) Inventors: David A. Becker, Parkland, FL (US); Relina Tamrakar, Miramar, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 14/353,511

(22) PCT Filed: Nov. 1, 2012

(86) PCT No.: PCT/US2012/062908
§ 371 (c)(1),
(2) Date: Apr. 23, 2014

(87) PCT Pub. No.: WO2013/067084
PCT Pub. Date: May 10, 2013

(65) Prior Publication Data
US 2014/0296184 A1    Oct. 2, 2014

Related U.S. Application Data

(60) Provisional application No. 61/554,030, filed on Nov. 1, 2011.

(51) Int. Cl.
*C07F 7/08* (2006.01)
*C07F 7/18* (2006.01)
*G01N 33/52* (2006.01)

(52) U.S. Cl.
CPC ............ *C07F 7/0818* (2013.01); *C07F 7/0812* (2013.01); *C07F 7/1856* (2013.01); *G01N 33/52* (2013.01); *G01N 2800/7009* (2013.01)

(58) Field of Classification Search
CPC .............................. C07F 7/0818; C07F 7/0812
See application file for complete search history.

(56) References Cited

FOREIGN PATENT DOCUMENTS

| EA | 004931 | 10/2014 | |
|---|---|---|---|
| EP | 0 888 290 | * 1/1999 | ............ C07C 251/14 |
| EP | 0888290 A1 | 1/1999 | |
| RU | 2225392 C2 | 3/2004 | |

OTHER PUBLICATIONS

Adachi et al., Effects of oxygen on protein carbonyl and aging in *Caenorhabditis elegans* mutants with long (age-1) and short (mev-1) life spans. J Gerontol A Biol Sci Med Sci, 53:B240-4 (1998).
Adrian et al., Electron spin resonance spectrum of HO2 in argon at 4.2° K. J. Chem. Phys., 47:5441-2 (1967).
Aikens et al., Perhydroxyl radical (HOO.bul.) initiated lipid peroxidation. The role of fatty acid hydroperoxides. J. Biol. Chem. 266:15091-8 (1991).
Akerboom et al., Assay of glutathione, glutathione disulfide, and glutathione mixed disulfides in biological samples. Methods Enzymol., 77:373-82 (1981).
Alexander, Hypertension and the pathogenesis of atherosclerosis. Oxidative stress and the mediation of arterial inflammatory response: a new perspective. Hypertension (Dallas), 25:155-61 (1995).
Alexandrova et al., Oxidative stress during the chronic phase after stroke. Free Radical Biol. Med. 39:297-316 (2005).
Allouch et al., Spin trapping of superoxide by diester-nitrones. Org. Biomol. Chem. 3:2458-62 (2005).
Amemiya et al., The novel oxidation of 1-alkylazulenes to 1-acylazulenes with DDQ, Chem. Lett., 587-90 (1977).
Anderson et al., Electrophilic substitution of some 1,3-disubstituted azulenes. J. Org. Chem., 28:2578-81 (1963).
Anderson et al., Preconditioning and the oxidants of sudden death. Curr Opin Crit Care, 9:194-8 (2003).
Aragno et al., Oxidative derangement in rat synaptosomes induced by hyperglycaemia: restorative effect of dehydroepiandrosterone treatment. Biochemical Pharmacology, 60:389-95 (2000).
Arditti et al., (eds.) Orchid Biology: Reviews and Perspectives, VII, 1997.
Ashburn et al., Generation and [3 + 2] cycloaddition reactions of oxazoline N-oxides. J. Org. Chem., 49:3127-33 (1984).
Ashok et al., Electron-transfer reactions. Reaction of nitrones with potassium. Can. J. Chem., 65:2039-49 (1987).
Augusto et al., Nitrogen dioxide and carbonate radical anion: two emerging radicals in biology. Free Radical Biol. Med. 32:841-59 (2002).
Aust et al., Evidence for superoxide generation by NADPH-cytochrome c reductase of rat liver microsomes. Biochem. Biophys. Res. Commun. 47:1133-7 (1972).
Babior et al., Oxygen-dependent microbial killing by phagocytes. Part 1. N. Engl. J. Med. 298:659-68 (1978).
Babior, NADPH oxidase: an update. Blood, 93:1464-76 (1999).
Babior, Phagocytes and oxidative stress. Am. J. Med. 109:33-44 (2000).
Babior, The NADPH oxidase of endothelial cells. IUBMB Life, 50:267-9 (2000).
Bagasra et al., Activation of the inducible form of nitric oxide synthase in the brains of patients with multiple sclerosis. Proc. Natl. Acad. Sci. U. S. A. 92: 12041-5 (1995).
Barrett et al., Regulation of PTP1B via Glutathionylation of the Active Site Cysteine 215. Biochemistry, 38:6699-705 (1999).
Bartoli et al., Production of superoxide anions and hydrogen peroxide in Ehrlich ascites tumour cell nuclei. Biochimica et Biophysica Acta (BBA)—General Subjects, 497:622-6 (1977).
Baynes, Role of oxidative stress in development of complications in diabetes. Diabetes. 40:405-12 (1991).
Beard et al., Iron in the brain. Nutr Rev., 51 :157-70 (1993).
Becker et al., A new synthesis of substituted azulenes. J. Am. Chem. Soc., 111:389-91 (1989).

(Continued)

*Primary Examiner* — Joseph Kosack
(74) *Attorney, Agent, or Firm* — Marshall, Gerstein & Borun LLP

(57) ABSTRACT

Silylated nitrones and methods of detecting and/or superoxide using silylated nitrones are disclosed herein.

18 Claims, No Drawings

(56) References Cited

OTHER PUBLICATIONS

Becker et al., Stilbazulenyl Nitrone (STAZN): A Nitronyl-Substituted Hydrocarbon with the Potency of Classical Phenolic Chain-Breaking Antioxidants. J. Am. Chem. Soc., 124:4678-84 (2002).
Becker, Diagnostic and therapeutic applications of azulenyl nitrone spin traps. Cell. Mol. Life Sci., 56:626-33 (1999).
Becker, Highly sensitive colorimetric detection and facile isolation of diamagnetic free radical adducts of novel chromotropic nitrone spin trapping agents readily derived from guaiazulene. Book of Abstracts, 211th ACS National Meeting, New Orleans, LA, Mar. 24-28 1996, ORGN-426.
Beckman et al., Apparent hydroxyl radical production by peroxynitrite: implications for endothelial injury from nitric oxide and superoxide. Proc. Natl. Acad. Sci. U. S. A. 87:1620-4 (1990).
Beckman et al., Nitric oxide, superoxide, and peroxynitrite: the good, the bad, and the ugly. Am. J. Physiol. 271:C1424-C1437 (1996).
Beckman, Oxidative Damage and Tyrosine Nitration from Peroxynitrite. Chem. Res. Toxicol., 9:836-44 (1996).
Belayev et al., Stilbazulenyl nitrone, a novel azulenyl nitrone antioxidant: improved neurological deficit and reduced contusion size after traumatic brain injury in rats. J. Neurosurg., 96:1077-83 (2002).
Benov et al., Critical evaluation of the use of hydroethidine as a measure of superoxide anion radical. Free Radical Biol. Med., 25:826-31 (1998).
Bergendi et al., Chemistry, physiology and pathology of free radicals. Life Sci. 65:1865-74 (1999).
Berliner et al., Distance Measurements in Biological Systems by EPR. Biol. Magn. Reson., 19 (2000).
Bernotas et al., Synthesis and radical scavenging activity of 3,3-dialkyl-3,4-dihydroisoquinoline 2-oxides. Bioorg. Med. Chem. Lett., 6, 1105-10 (1996).
Bernotas et al., Synthesis of benzazepine-based nitrones as radical traps. Tetrahedron, 52:6519-26 (1996).
Bhunia et al., Redox-regulated signaling by lactosylceramide in the proliferation of human aortic smooth muscle cells, J. Biol. Chem., 272(25):15642-9 (1997).
Bilski et al., Quenching and generation of singlet oxygen by hydroethidine and related chromophores. Chem. Phys. Lett., 475:116-9 (2009).
Bindokas et al., Superoxide production in rat hippocampal neurons: selective imaging with hydroethidine. J. Neurosci., 16:1324-36 (1996).
Black, The biochemistry of sulfur-containing compounds. Annu. Rev. Biochem. 32:399-418 (1963).
Bonnett et al., Experiments towards the synthesis of corrins. II. Preparation and reactions of 1-pyrroline 1-oxides. J. Chem. Soc., 2094-102 (1959).
Boveris et al., Mitochondrial generation of hydrogen peroxide. General properties and effect of hyperbaric oxygen. Biochem. J. 134:707-16 (1973).
Breen et al., Reactions of oxyl radicals with DNA. Free Radical Biology and Medicine, 18:1033-77 (1995).
Britigan et al., Do human neutrophils make hydroxyl radical? Determination of free radicals generated by human neutrophils activated with a soluble or particulate stimulus using electron paramagnetic resonance spectrometry. J. Biol. Chem., 261:4426-31 (1986).
Brown et al., $\Delta$1-Pyrroline N-oxides. Proc. Chem. Soc., 97-8 (1957).
Buettner et al., Considerations in the spin trapping of superoxide and hydroxyl radical in aqueous systems using 5,5-dimethyl-1-pyrroline-1-oxide. Biochem. Biophys. Res. Commun., 83:69-74 (1978).
Bunn et al., Oxygen sensing and molecular adaptation to hypoxia. Physiol. Rev. 76: 839-85 (1996).
Burda et al., Mechanisms of ischemic tolerance acquisition: the role of nitric oxide. NO-cGMP Signaling Spinal Cord Brain Stem Circuitry,1-10 (2009).
Busciglio et al., Apoptosis and increased generation of reactive oxygen species in Down's syndrome neurons in vitro. Nature, 378:776-9 (1995).
Butterfield et al., Evidence that amyloid beta-peptide-induced lipid peroxidation and its sequelae in Alzheimer's disease brain contribute to neuronal death. Neurobiol Aging, 23:655-64 (2002).
Cadenas et al., Mitochondrial free radical generation, oxidative stress, and aging. Free Radical Biol. Med., 29:222-30 (2000).
Cadenas, Basic mechanisms of antioxidant activity. BioFactors, 6:391-7 (1997).
Cadet et al., Hydroxyl radicals and DNA base damage. Mutat. Res., Fundam. Mol. Mech. Mutagen. 424:9-21 (1999).
Cairo et al., The iron regulatory proteins: targets and modulators of free radical reactions and oxidative damage. Free Radical Biol. Med. 32:1237-43 (2002).
Campbell et al., Preparation of unsymmetrical secondary aliphatic amines. J. Am. Chem. Soc., 66:82-4 (1944).
Candeias et al., Free hydroxyl radicals are formed on reaction between the neutrophil-derived species superoxide anion and hypochlorous acid. FEBS Lett. 333:151-3 (1993).
Carter et al. Intracellular hydrogen peroxide and superoxide anion detection in endothelial cells. J. Leukocyte Biol., 55:253-8 (1994).
Chalfont et al., Probe for homolytic reactions in solution. II. Polymerization of styrene. J. Amer. Chem. Soc., 90:7141-2 (1968).
Chalier et al., 5-Diisopropoxyphosphoryl-5-methyl-1-pyrroline N-oxide, DIPPMPO, a crystalline analog of the nitrone DEPMPO: synthesis and spin trapping properties. J. Chem. Soc., Perkin Trans. 2, 2110-7 (2002).
Chalier et al., Design of New Derivatives of Nitrone DEPMPO Functionalized at C-4 for Further Specific Applications in Superoxide Radical Detection. J. Org. Chem., 72:7886-92 (2007).
Chamoun et al., Pathophysiologic role of selectins and their ligands in ischemia reperfusion injury. Front. Biosci., 5: E103-E109 (2000).
Chance et al., Hydroperoxide metabolism in mammalian organs. Physiol. Rev. 59:527-605 (1979).
Chancel, Sur la propylpropylidene-amine, Bull. Soc. Chim., 11:933-7 (1894). [French only].
Chapter 3 The detection and characterization of free radical species. In: Evans (ed.), Laboratory Techniques in Biochemistry and Molecular Biology, Elsevier, vol. 22; pp. 51-100 (1991).
Chen et al., Increased oxidative damage and mitochondrial abnormalities in the peripheral blood of Huntington's disease patients. Biochem. Biophys. Res. Commun., 359: 335-40 (2007).
Chiacchio et al., New Rearrangement of 4-Isoxazoline System: Conversion of Ketones into $\alpha,\beta$-Unsaturated Amides. J. Org. Chem. 68:3718-20 (2003).
Chiacchio et al., Novel approach to the ring-opening of 4-isoxazolines: one-pot synthesis of $\alpha,\beta$-enones. Tetrahedron, 48:123-32 (1992).
Chiacchio et al., Ring opening of 4-isoxazolines: competitive formation of enamino derivatives and $\alpha,\beta$-enones. Heterocycles, 36:585-600 (1993).
Chobanian et al., Influence of hypertension on aortic atherosclerosis in the Watanabe rabbit. Hypertension, 14:203-9 (1989).
Clement et al., Production of Intracellular Superoxide Mediates Dithiothreitol-Dependent Inhibition of Apoptotic Cell Death. Antioxid. Redox Signaling, 7:456-64 (2005).
Commoner et al., Free radicals in biological materials. Nature, 174:689-91 (1954).
Cooke et al., Oxidative DNA damage: mechanisms, mutation, and disease. Faseb J., 17:1195-214 (2003).
Dage et al., Evidence for a novel pentyl radical adduct of the cyclic nitrone spin trap MDL 101,002. Free Radical Biol. Med., 22:807-12 (1997).
Davies, Protein damage and degradation by oxygen radicals. I. General aspects. J. Biol. Chem., 262:9895-901 (1987).
de Haan et al., Elevation in the ratio of Cu/Zn-superoxide dismutase to glutathione peroxidase activity induces features of cellular senescence and this effect is mediated by hydrogen peroxide. Hum. Mol. Genet. 5:283-92 (1996).
De Mattia et al., Influence of reduced glutathione infusion on glucose metabolism in patients with non-insulin-dependent diabetes mellitus. Metab., Clin. Exp., 47:993-7 (1998).
De Sandro et al., Mechanism of NADPH oxidation catalyzed by horse-radish peroxidase and 2,4-diacetyl-[2H]heme-substituted horse-radish peroxidase. Eur J Biochem, 201:507-13 (1991).

(56) References Cited

OTHER PUBLICATIONS

Dean et al.. Biochemistry and pathology of radical-mediated protein oxidation. Biochem. J., 324:1-18 (1997).
Dehnel et al., Designer spin traps with a cyclic nitrone structure. J. Org. Chem. 53:1566-7 (1988).
Deng et al., Mutations in UBQLN2 cause dominant X-linked juvenile and adult-onset ALS and ALS/dementia. Nature, 477:211-5 (2011).
Dikalov et al., Measurement of reactive oxygen species in cardiovascular studies, Hypertension, 49(4):717-27 (2007).
Dillard et al., Fluorescent damage products of lipid peroxidation. Methods Enzymol., 105:337-41 (1984).
Downey, Free radicals and their involvement during long-term myocardial ischemia and reperfusion. Annu. Rev. Physiol., 52:487-504 (1990).
Droge, Free radicals in the physiological control of cell function, Physiol. Rev., 82:47-95 (2002).
Dupeyre et al., Nitroxides. XIX. Norpseudopelletierine-N-oxyl, a new, stable, unhindered free radical. J. Am. Chem. Soc., 88: 3180-1 (1966).
Durackova, Antioxidants as good and bad compounds. Klin. Biochem. Metab., 5: 194-9 (1997).
Elroy-Stein et al., Overproduction of human copper/zinc-superoxide dismutase in transfected cells: extenuation of paraquat-mediated cytotoxicity and enhancement of lipid peroxidation. Embo J., 5:615-22 (1986).
Engelmann et al., Variability of the Fenton reaction characteristics of the EDTA, DTPA, and citrate complexes of iron. BioMetals, 16:519-27 (2003).
Esterbauer et al., Chemistry and biochemistry of 4-hydroxynonenal, malonaldehyde and related aldehydes. Free Radical Biology and Medicine, 11:81-128 (1991).
Fahl et al., DNA damage related to increased hydrogen peroxide generation by hypolipidemic drug-induced liver peroxisomes. Proc. Natl. Acad. Sci. U. S. A. 81:7827-30 (1984).
Farooqui et al., Lipid peroxides in the free radical pathophysiology of brain diseases. Cell. Mol. Neurobiol. 18:599-608 (1998).
Faulkner et al., Luminol and lucigenin as detectors for O2s[combining dot above]. Free Radical Biology and Medicine, 15:447-51 (1993).
Fernandes et al., Analysis of DHE-derived oxidation products by HPLC in the assessment of superoxide production and NADPH oxidase activity in vascular systems. Am J Physiol Cell Physiol, 292:C413-22 (2007).
Ferrari et al., Role of oxygen free radicals in ischemic and reperfused myocardium. Am. J. Clin. Nutr. 53:215S-22S (1991).
Finkel, Oxygen radicals and signaling. Curr. Opin. Cell Biol. 10:248-53 (1998).
Finkelstein et al., Spin trapping of superoxide and hydroxyl radical: Practical aspects. Archives of Biochemistry and Biophysics, 200:1-16 (1980).
Finkelstein et al., Spin trapping of superoxide. Mol. Pharmacol., 16:676-85 (1979).
Floyd et al., Oxidative biochemical markers; clues to understanding aging in long-lived species. Exp. Gerontol. 36:619-40 (2001).
Fowler, New synthesis of unsymmetrical azo compounds. J. Org. Chem. 37:510-11 (1972).
Fraga et al., Oxidative damage to DNA during aging: 8-hydroxy-2'-deoxyguanosine in rat organ DNA and urine. Proc. Natl. Acad. Sci. U. S. A., 87:4533-7 (1990).
Fredriksson et al., MPTP-induced deficits in motor activity: neuroprotective effects of the spin-trapping agent, α-phenyl-tert-butyl-nitrone (PBN). J. Neural Transm., 104:579-92 (1997).
Frejaville et al., 5-(Diethoxyphosphoryl)-5-methyl-1-pyrroline N-oxide: A New Efficient Phosphorylated Nitrone for the in Vitro and in Vivo Spin Trapping of Oxygen-Centered Radicals. J. Med. Chem., 38:258-65 (1995).
Frejaville et al., 5-Diethoxyphosphoryl-5-methyl-1-pyrroline N-oxide (DEPMPO): a new phosphorylated nitrone for the efficient in vitro and in vivo spin trapping of oxygen-centered radicals. J. Chem. Soc., Chem. Commun. 1793-4 (1994).
Frey et al., L-Thiocitrulline. A stereospecific, heme-binding inhibitor of nitric-oxide synthases. J. Biol. Chem. 269:26083-91 (1994).
Fridovich et al., Superoxide radical: an endogenous toxicant, Annu. Rev. Pharmacol. Toxicol., 23:239-57 (1983).
Fridovich, Superoxide radical and superoxide dismutaseAcc. Chem. Res., 5:321-6 (1972).
Fridovich, Evidence for the symbiotic origin of mitochondria. Life Sci, 14:819-26 (1974).
Fridovich, Superoxide radical: an endogenous toxicant, Free Radicals in Biology, 1:239-77 (1976).
Friestad et al., Ion-Radical Organic Chemistry: Principles and Applications, 2nd ed. by Zory Vlad Todres, vol. 131 2009).
Gerschman et al., Oxygen poisoning and x-irradiation: mechanism in common. Science (Washington, DC, U. S.), 119:623-6 (1954).
Gersh, Current issues in reperfusion therapy. Am J Cardiol., 82:3P-11P (1998).
Giner-Sorolla et al., Synthesis of purine-6-carboxaldehyde and related derivatives. J. Am. Chem. Soc., 81:2515-21 (1959).
Goldstein et al., Chemical and pharmacological aspects of heteroarylnitrones. Curr. Med. Chem., 7:1255-67 (2000).
Gomberg, An instance of trivalent carbon: triphenylmethyl. J. Am. Chem. Soc. 22:757-71 (1900).
Goode et al., Reperfusion injury, antioxidants and hemodynamics during orthotopic liver transplantation. Hepatology, 19:354-9 (1994).
Gothelf et al., Catalytic enantioselective 1,3-dipolar cycloaddition reactions of nitrones. Chem. Commun. (Cambridge), 1449-58 (2000).
Goto et al., An improved synthesis of N-hydroxy amino acids and their esters using (Z)-2-furaldehyde oxime. Chem. Pharm. Bull., 34:3202-7 (1986).
Granger, Role of xanthine oxidase and granulocytes in ischemia-reperfusion injury. Am J Physiol., 255: H1269-75 (1988).
Greenlee et al., Chemiluminescence induced by operation of iron-flavo-proteins. Biochemistry, 1:779-83 (1962).
Griendling et al., Modulation of protein kinase activity and gene expression by reactive oxygen species and their role in vascular physiology and pathophysiology. Arterioscler. Thromb. Vasc. Biol. 20:2175-83 (2000).
Griscavage et al., Nitric oxide inhibits neuronal nitric oxide synthase by interacting with the heme prosthetic group. Role of tetrahydrobiopterin in modulating the inhibitory action of nitric oxide. J. Biol. Chem., 269:21644-9 (1994).
Grollman et al., Mutagenesis by 8-oxoguanine: an enemy within. Trends in Genetics, 9:246-9 (1993).
Gruenwedel et al. (eds.), Food Analysis: Principles and Techniques, vol. 4, Separation Techniques, 1987.
Grunfeld et al., Role of superoxide in the depressed nitric oxide production by the endothelium of genetically hypertensive rats. Hypertension, 26:854-7 (1995).
Gurney et al., Mutant Cu,Zn superoxide dismutase in motor neuron disease, Age, 21 (2):85-9 (1998).
Guyton et al., Oxidative mechanisms in carcinogenesis. Br. Med. Bull. 49:523-44 (1993).
Gyllenhammar, Lucigenin chemiluminescence in the assessment of neutrophil superoxide production. J. Immunol. Methods, 97:209-13 (1987).
Hack et al., Cystine levels, cystine flux, and protein catabolism in cancer cachexia, HIV/SIV infection, and senescence. Faseb J., 11:84-92 (1997).
Halliwell et al., The definition and measurement of antioxidants in biological systems, Free Radicals in Biology and Medicine, 18(1):125-6 (1988).
Halliwell, Free radicals, reactive oxygen species and human disease: a critical evaluation with special reference to atherosclerosis. Br J Exp Pathol., 70:737-57 (1989).
Halliwell, Generation of the superoxide radical during the peroxidatic oxidation of NADH by catalase at acid pH values. FEBS Lett., 80:291-3 (1977).
Halliwell, Lignin synthesis: the generation of hydrogen peroxide and superoxide by horseradish peroxidase and its stimulation by manganese(II) and phenols. Planta, 140:81-8 (1978).
Hamer et al., Nitrones. Chem. Rev., 64:473-95 (1964).

(56) References Cited

OTHER PUBLICATIONS

Harbour et al., Electron spin resonance study of the spin adducts of hydroxy and hydrogen dioxide radicals with nitrones in the ultraviolet photolysis of aqueous hydrogen peroxide solutions. Can. J. Chem., 52:3549-53 (1974).
Harman, Aging: a theory based on free radical and radiation chemistry. J Gerontol., 11:298-300 (1956).
Harrison, Structure and function of xanthine oxidoreductase: where are we now? Free Radical Biology and Medicine, 33:774-97 (2002).
He, Mortality and apnea index in obstructive sleep apnea. Experience in 385 male patients. Chest, 94:9-14 (1988).
Hengartner, The biochemistry of apoptosis. Nature, 407:770-6 (2000).
Hensley et al., Reactive oxygen species, cell signaling, and cell injury. Free Radical Biol. Med., 28:1456-62 (2000).
Hink et al., Mechanisms underlying endothelial dysfunction in diabetes mellitus. Circ. Res., 88:e14-e22 (2001).
Hoffmann et al., A new stable free radical: di-tert-Butylnitroxide. J. Am. Chem. Soc., 83:4671 (1961).
Houk et al., Nitrone ionization potentials and cycloaddition regioselectivities. Heterocycles, 7:293-9 (1977).
Huisgen et al., 1,3-Dipolar cycloaddition. XLVII. Reactions of heteroaromatic amines oxide with carboxylic esters of the ethylene and acetylene series. Chem. Ber. 102:915-25 (1969).
Huisgen et al., The chemistry of an isolable azomethine ylide. Heterocycles, 22: 21-6 (1984).
Hussain et al., Oxy-radical induced mutagenesis of hotspot codons 248 and 249 of the human p53 gene. Oncogene. 9: 2277-81 (1994).
Hussain et al., Radical causes of cancer. Nat. Rev. Cancer, 3:276-85 (2003).
Ignarro et al., The pharmacological and physiological role of cyclic GMP in vascular smooth muscle relaxation. Annu Rev Pharmacol Toxicol., 25:171-91 (1985).
Ignarro, Nitric oxide: a unique endogenous signaling molecule in vascular biology. Prix Nobel, 252-72 (1999).
International Search Report and Written Opinion, corresponding international application No. PCT/US2012/062908, mailing date Feb. 28, 2013.
Iwamura et al., Novel formation of nitroxide radicals by radical addition to nitrones. Bull. Chem. Soc. Jpn., 40:703 (1967).
Janzen et al., On spin trapping hydroxyl and hydroperoxy radicals. Can. J. Chem. 56:2237-42 (1978).
Janzen et al., Rate constants for spin trapping tert-butoxy radicals as studied by electron spin resonance. J. Am. Chem. Soc., 95:8205 (1973).
Janzen et al., Spin trapping in SDS micelles. J. Am. Chem. Soc., 106:1962-8 (1984).
Jenner, Oxidative stress and Parkinson's disease. IN: Aminoff (ed.), Handbook of Clinical Neurology, Elsevier, vol. 83; pp. 507-520 (2007).
Jones et al., Light-dependent reduction of copper(II) and its effect on cell-mediated, thiol-dependent superoxide production. Biochemical and Biophysical Research Communications. 128:1031-6 (1985).
Kambayashi et al., Reestimation of Cypridina luciferin analogs (MCLA) as a chemiluminescence probe to detect active oxygen species: cautionary note for use of MCLA. J. Toxicol. Sci., 28:139-48 (2003).
Kanofsky, Singlet oxygen production by chloroperoxidase-hydrogen peroxide-halide systems. J. Biol. Chem., 259:5596-600 (1984).
Kanofsky, Singlet oxygen production by lactoperoxidase. Evidence from 1270 nm chemiluminescence. J. Biol. Chem. 258:5991-3 (1983).
Karoui et al., ESR-spin trapping in the presence of cyclodextrins. Detection of PBN-superoxide spin adduct. Tetrahedron Letters, 45:1043-5 (2004).
Katz et al., Reperfusion injury following single-lung transplantation: The tissue glutathione response. J. Pediatric Surg., 28:1301-6 (1993).
Keszler et al., Comparative investigation of superoxide trapping by cyclic nitrone spin traps: the use of singular value decomposition and multiple linear regression analysis. Free Radical Biology and Medicine, 35:1149-57 (2003).
Kim et al., Alpha-phenyl-N-tert-butyl nitrone (PBN) derivatives: synthesis and protective action against microvascular damages induced by ischemia/reperfusion, Bi000rg. Med. Chem., 15(10):3572-8 (2007).
Kinscherf et al., Characterization of apoptotic macrophages in atheromatous tissue of humans and heritable hyperlipidemic rabbits. Atherosclerosis, 144:33-9 (1999).
Klein et al., Metallation reactions. XIV. Generality of the 1,3-sigmatropic shift of hydrogen in allenyllithium compounds. Tetrahedron, 28:5385-92 (1972).
Klivenyi et al., Azulenyl nitrone spin traps protect against MPTP neurotoxicity. Exp. Neurol., 152:163-6 (1998).
Klotz, Oxidant-induced signaling: effects of peroxynitrite and singlet oxygen. Biol. Chem. 383:443-56 (2002).
Koppenol, The Haber-Weiss cycle—70 years later. Redox Rep., 6:229-34 (2001).
Kukreja et al., PGH synthase and lipoxygenase generate superoxide in the presence of NADH or NADPH. Circ. Res. 59: 612-9 (1986).
Kulkarni et al., Superoxide generation links nociceptin/orphanin FQ (NOC/oFQ) release to impaired N-methyl-D-aspartate cerebrovasodilation after brain injury. Stroke, 31:1990-6 (2000).
Lapchak et al., De-Risking of Stilbazulenyl Nitrone (STAZN), a Lipophilic Nitrone to Treat Stroke Using a Unique Panel of In Vitro Assays. Trans!. Stroke Res., 2:209-17 (2011).
Lauricella et al., A new kinetic approach to the evaluation of rate constants for the spin trapping of superoxide/hydroperoxyl radical by nitrones in aqueous media. Org. Biomol. Chem. 2:1304-9 (2004).
Laursen et al., Role of superoxide in angiotensin II-induced but not catecholamine-induced hypertension. Circulation, 95:588-93 (1997).
Levine, R. L.; Stadtman, E. R.: Oxidative modification of proteins during aging. Exp. Gerontol., 36:1495-1502 (2001).
Ley et al., Neuroprotective antioxidant STAZN protects against myocardial ischemia/reperfusion injury. Biochem. Pharmacol., 75:448-56 (2008).
Ley et al., Stilbazulenyl nitrone, a second-generation azulenyl nitrone antioxidant, confers enduring neuroprotection in experimental focal cerebral ischemia in the rat: neurobehavior, histopathology, and pharmacokinetics. J Pharmacol Exp Ther, 313:1090-100 (2005).
Li et al., Validation of lucigenin (bis-N-methylacridinium) as a chemilumigenic probe for detecting superoxide anion radical production by enzymic and cellular systems. J. Biol. Chem., 273:2015-23 (1998).
Li et al., Ab lnitio Molecular Dynamics Study of the Electronic Structure of Superoxide Radical Anion in Solution. J. Phys. Chem. A 113:800-4 (2009).
Liochev et al., Lucigenin (bis-N-methylacridinium) as a mediator of superoxide anion production, Arch. Biochem. Biophys., 337:115-20 (1997).
Liu et al., Enhanced oxygen radical production in a transgenic mouse model of familial amyotrophic lateral sclerosis. Ann. Neurol., 44:763-70 (1998).
Loft et al., Cancer risk and oxidative DNA damage in man. J. Mol. Med., 74:297-312 (1996).
Lombardo et al., Nucleophilic additions to nitrones. Synthesis, 759-74 (2000).
Lovell et al., Elevated 4-Hydroxynonenal in ventricular fluid in Alzheimer's disease. Neurobiol. Aging, 18:457-61 (1997).
Lowenstein et al., Nitric oxide: a physiologic messenger. Ann Intern Med, 120: 227-37 (1994).
Luo et al., A novel synthesis of cyanoalkynes via iodide-catalyzed cyanation of terminal acetylenes with cuprous cyanide. Tetrahedron Lett., 34:5911-4 (1993).
Luo et al., Preparation of cyanoalkynes: 3-phenyl-2-propynenitrile. Org. Synth. vol. 10,p. 645 (2004); vol. 75, p. 146(1998).
Lynch et al., Lipoxygenase-mediated production of superoxide anion in senescing plant tissue. FEBS Letters, 173:251-4 (1984).

(56) References Cited

OTHER PUBLICATIONS

Lyras et al., An assessment of oxidative damage to proteins, lipids, and DNA in brain from patients with Alzheimer's disease. J. Neurochem., 68:2061-9 (1997).
Maddipati et al., Characterization of the hydroperoxide-reducing activity of human plasma. Arch. Biochem. Biophys. 254:9-17 (1987).
Mann et al., Total synthesis of amiclenomycin, an inhibitor of biotin biosynthesis, Chemistry, 8(2):439-50 (2002).
Marnett, Oxyradicals and DNA damage. Carcinogenesis, 21:361-70 (2000).
McCarron et al., Health co-morbidities in ageing persons with Down syndrome and Alzheimer's dementia. J Intellect Disabil Res., 49:560-6 (2005).
McCord et al., Superoxide dismutase. Enzymic function for erythrocuprein (hemocuprein). J. Biol. Chem. 244:6049-55 (1969).
McCormick et al., Eosinophil peroxidase-dependent hydroxyl radical generation by human eosinophils. J. Biol. Chem. 269:27914-19 (1994).
Meisel et al., Hydroperoxyl radical reactions. II. Cupric ions in modulated photolysis. Electron paramagnetic resonance experiments. J. Phys. Chem., 78: 779-82 (1974).
Merritt et al., Electrochemical studies of the reactivity of superoxide ion with several alkyl halides in dimethyl sulfoxide. J. Org. Chem. 35:2157-9 (1970).
Mikkelsen et al., Biological chemistry of reactive oxygen and nitrogen and radiation-induced signal transduction mechanisms. Oncogene, 22:5734-54 (2003).
Milne et al., Effects of glutathione and chelating agents on copper-mediated DNA oxidation: pro-oxidant and antioxidant properties of glutathione. Arch Biochem Biophys, 304:102-9 (1993).
Misra, Generation of superoxide free radical during the autoxidation of thiols. J. Biol. Chem. 249:2151-5 (1974).
Mittal et al., Activation of guanylate cyclase by superoxide dismutase and hydroxyl radical: A physiological regulator of guanosine 3',5'-monophosphate formation. Proc. Natl. Acad. Sci. U. S. A. 74:4360-4 (1977).
Morawietz et al., Upregulation of Vascular NAD(P)H Oxidase Subunit gp91phox and Impairment of the Nitric Oxide Signal Transduction Pathway in Hypertension. Biochem. Biophys. Res. Comm., 285: 1130-5 (2001).
Morehouse et al., Generation of superoxide by the microsomal mixed-function oxidase system. Basic Life Sci. 49: 517-21 (1988).
Moriwaki et al., Enzymes involved in purine metabolism—a review of histochemical localization and functional implications. Histol. Histopathol. 14: 1321-40 (1999).
Nair et al., The reaction of cyclohexyl isocyanide and dimethyl acetylenedicarboxylate with aldehydes: a novel synthesis of 2-aminofuran derivatives. Chem. Commun. (Cambridge), 1019-1020 (2000).
Nakamura et al., Role of reactive oxygen in tumor promotion: implication of superoxide anion in promotion of neoplastic transformation in JB-6 cells by TPA. Carcinogenesis. 6:229-35 (1985).
Nakano et al., Chemiluminescence probe with Cypridina luciferin analog, 2-methyl-6-phenyl-3,7-dihydroimidazo[1,2-a]pyrazin-3-one, for estimating the ability of human granulocytes to generate O2. Anal. Biochem., 159:363-9 (1986).
Nakazono et al., Does superoxide underlie the pathogenesis of hypertension? Proc. Natl. Acad. Sci. U. S. A., 88:10045-8 (1991).
Nathan, Points of control in inflammation. Nature, 420:846-52 (2002).
Nelson et al., Corticosteroids increase superoxide anion production by rat liver microsomes. J. Clin. Invest. 56:1062-5 (1975).
Nishikawa et al., Normalizing mitochondrial superoxide production blocks three pathways of hyperglycemic damage. Nature, 404:787-91 (2000).
Novelli et al., Spin trap phenyl butyl nitrone prevents lethal shock in the rat. Free Radicals Liver Injury Proc. Int. Meet., 225-8 (1985).
Oberley et al., Role of superoxide dismutase in cancer: a review. Cancer Res, 39:1141-9 (1979).

Oberley, Free radicals and diabetes. Free Radic Biol Med, 5:113-24 (1998).
Ohara et al., Hypercholesterolemia increases endothelial superoxide anion production. J. Clin. Invest., 91:2546-51 (1993).
Okajima et al., Facile conversion of 1-methyl group of guaiazulene into 1-formyl group. Chem. Lett., 69-70 (1997).
Olive et al., 2-Ethoxycarbonyl-2-methyl-3,4-dihydro-2H-pyrrole-1-oxide: evaluation of the spin trapping properties. Free Radical Biol. Med., 28:403-8 (2000).
Omar et al., Inhibition of coronary artery superoxide dismutase attenuates endothelium-dependent and -independent nitrovasodilator relaxation. Circ. Res. 69:601-8 (1991).
Palazzolo-Ballance et al., Pathways for Intracellular Generation of Oxidants and Tyrosine Nitration by a Macrophage Cell Line. Biochemistry, 46:7536-48 (2007).
Pandey et al., Enzymatic oxidant and antioxidant of human blood platelets in unstable angina and myocardial infarction. International Journal of Cardiology, 76:33-8 (2000).
Papapostolou et al., The fluorescence detection of superoxide radical using hydroethidine could be complicated by the presence of heme proteins. Analytical Biochemistry, 332:290-8 (2004).
Park et al., Xanthine oxidase: biochemistry, distribution and physiology. Acta Physiol. Scand., Suppl. 548:87-99 (1986).
Peskin et al., Superoxide dismutase and glutathione peroxidase activities in tumors. FEBS Lett. 78:41-5 (1977).
Pfeiffer et al., Photochemical syntheses of indole derivatives. Justus Liebigs Ann. Chem., 411:72-158 (1916).
Poli et al., Oxidative stress and cell signaling. Curr. Med. Chem. 11:1163-82 (2004).
Pou et al., Problems associated with spin trapping oxygen-centered free radicals in biological systems. Anal. Biochem., 177:1-6 (1989).
Pratico et al., Increased F2-isoprostanes in Alzheimer's disease: evidence for enhanced lipid peroxidation in vivo. Faseb J. 12:1777-83 (1998).
Prousek, Fenton reaction after a century. Chem. Listy, 89:11-21 (1995).
Pryor et al., The chemistry of peroxynitrite: a product from the reaction of nitric oxide with superoxide. Am. J. Physiol., 268:L699-L722 (1995).
Prütz et al., The glutathione free radical equilibrium, GS. + GS-[right harpoon over left] GSS.-G, mediating electron transfer to FE(III)-cytochrome c. Biophysical Chemistry, 49: 101-11 (1994).
Radi, Peroxynitrite Reactions and Diffusion in Biology. Chem. Res. Toxicol. 11: 720-1 (1998).
Reckelhoff et al., Subpressor doses of angiotensin II increase plasma F2-isoprostanes in rats. Hypertension, 35:476-9 (2000).
Rehorek et al., Spin trapping in photochemistry of coordination compounds. Can. J. Chem. 60:1565-73 (1982).
Rembish et al., Further evidence that lucigenin-derived chemiluminescence monitors mitochondrial superoxide generation in rat alveolar macrophages. Free Radical Biology and Medicine, 17:117-26 (1994).
Reusch, Diabetes, microvascular complications, and cardiovascular complications: What is it about glucose? J. Clin. Invest., 112:986-8 (2003).
Rizzi et al., PPN-type nitrones: preparation and use of a new series of β-phosphorylated spin-trapping agents. J. Chem. Soc., Perkin Trans. 2, 2513-8 (1997).
Rosen et al., Detection of superoxide generated by endothelial cells, Proc. Natl. Acad. Sci. USA, 81(23): 7269-73 (1984).
Rosen et al., Free Radicals: Biology and Detection by Spin Trapping (1999).
Rosen et al., Mutations in copper/zinc superoxide dismutase gene are associated with familial amyotrophic lateral sclerosis. Nature, 362:59-62 (1993).
Roth et al., Regulation of T-cell activation and T-cell growth factor (TCGF) production by hydrogen peroxide. Cell. Immunol. 108:417-24 (1987).
Roubaud et al., Decay of superoxide spin adducts of new PBN-type phosphorylated nitrones. Res. Chem. Intermed., 22:405-16 (1996).
Roy et al., Superoxide generation by lipoxygenase in the presence of NADH and NADPH. Biochimica et Biophysica Acta (BBA)—Lipids and Lipid Metabolism 1214: 171-9 (1994).

(56) References Cited

OTHER PUBLICATIONS

Russo et al., Anti-oxidant status and lipid peroxidation in patients with essential hypertension. J. Hypertens., 16:1267-71 (1998).
Sabitha et al., LiCl catalyzed Knoevenagel condensation: comparative study of conventional method vs. microwave irradiation. Chem. Lett., 773-4 (1998).
Sagar et al. Oxygen free radicals in essential hypertension. Mol. Cell. Biochem. 111:103-8 (1992).
Saiki et al., Quantitative fluorescent microassay for identification of antiproliferative compounds. J. Natl. Cancer Inst., 77:1235-40 (1986).
Saito et al., Electron paramagnetic resonance spectrum of the HO2 radical in aqueous solution. J. Am. Chem. Soc., 83:4467-8 (1961).
Salvemini et al., A nonpeptidyl mimic of superoxide dismutase with therapeutic activity in rats. Science, 286:304-6 (1999).
Sayre et al., 4-Hydroxynonenal-derived advanced lipid peroxidation end products are increased in Alzheimer's disease. J. Neurochem. 68:2092-7 (1997).
Sayre et al., Chemistry and biochemistry of oxidative stress in neurodegenerative disease. Curr. Med. Chem. 8:721-38 (2001).
Sayre et al., Oxidative Stress and Neurotoxicity. Chem. Res. Toxicol. 21:172-88 (2008).
Schafer et al., Redox environment of the cell as viewed through the redox state of the glutathione disulfide/glutathione couple. Free Radical Biol. Med., 30:1191-212 (2001).
Schulz et al., Enhanced release of superoxide from polymorphonuclear neutrophils in obstructive sleep apnea. Impact of continuous positive airway pressure therapy. Am J Respir Crit Care Med, 162:566-70 (2000).
Searcey et al., A mild procedure for the production of secondary amines from oximes and benzisoxazoles. Tetrahedron Lett., 44:6745-7 (2003).
Shepard, Hypertension, cardiac arrhythmias, myocardial infarction, and stroke in relation to obstructive sleep apnea. Clin Chest Med, 13:437-58 (1992).
Shigenaga et al., Urinary 8-hydroxy-2'-deoxyguanosine as a biological marker of in vivo oxidative DNA damage. Proc. Natl. Acad. Sci. U. S. A., 86:9697-701 (1989).
Sies, Strategies of antioxidant defense. Eur. J. Biochem., 215:213-19 (1993).
Sipowicz et al., Increased oxidative DNA damage and hepatocyte overexpression of specific cytochrome P450 isoforms in hepatitis of mice infected with Helicobacter hepaticus. Am. J. Pathol. 151 :933-41 (1997).
Smith et al., Ortho-TMS benzaldehyde: an effective linchpin for type II anion relay chemistry (ARC). Angew. Chem., Int. Ed., 47:7082-6 (2008).
Smith, Aliphatic diazo compounds, nitrones, and structurally analogous compounds. Systems capable of undergoing 1,3-additions. Chem. Rev., 23:193-285 (1938).
Sorescu et al., Superoxide production and expression of Nox family proteins in human atherosclerosis. Circulation, 105:1429-35 (2002).
Sparaco et al., Friedreich's ataxia: Oxidative stress and cytoskeletal abnormalities. J. Neurologic. Sci., 287:111-8 (2009).
Stadtman, Metal ion-catalyzed oxidation of proteins: biochemical mechanism and biological consequences. Free Radic Biol Med, 9:315-25 (1990).
Stadtman, Protein oxidation in aging and age-related diseases. Ann. N. Y. Acad. Sci., 928:22-38 (2000).
Steenken, Purine bases, nucleosides, and nucleotides: aqueous solution redox chemistry and transformation reactions of their radical cations and e- and OH adducts. Chem. Rev., 89:503-20 (1989).
Stokker, Preparation of 1,2-benzisoxazoles from salicylaldoximes via trichloroacetyl isocyanate. J. Org. Chem., 48:2613-15 (1983).
Stuehr et al., Induction of nitrite/nitrate synthesis in murine macrophages by BCG infection, lymphokines, or interferon-γ. J. Immunol., 139: 518-25 (1987).
Sugimoto et al., Degradation and dehalogenation of polychlorobiphenyls and halogenated aromatic molecules by superoxide ion and by electrolytic reduction. Environ. Sci. Technol. 22:1182-6 (1988).
Tamao et al., Hydrogen peroxide oxidation of the silicon-carbon bond: mechanistic studies. Front. Organosilicon Chem., [Proc. Int. Symp. Organosilicon Chem.], 9th , 197-207 (1991).
Tamao et al., Silafunctional compounds in organic synthesis. 45. An efficient oxidative cleavage of carbon-silicon bonds by a dioxygen/hydroquinone system. Tetrahedron Lett., 30:6533-6 (1989).
Tamao et al., Silafunctional compounds in organic synthesis. Part 20. Hydrogen peroxide oxidation of the silicon-carbon bond in organoalkoxysilanes. Organometallics, 2:1694-6 (1983).
Tamao et al., Structure and reactivity of hypercoordinate silicon compounds. Mechanism of hydrogen peroxide oxidation of silicon-carbon bonds. Nippon Kagaku Kaishi, 509-15 (1990).
Tarakhovskii et al., Formation of superoxide radicals by nuclear membranes of human brain tumors. Byull. Eksp. Biol. Med. 99:88-90 (1985).
Tarr et al., Oxygen Free Radicals in Tissue Damage (1993).
Tawadros et al., Stilbazulenyl nitrone decreases oxidative stress and reduces lung injury after hemorrhagic shock/resuscitation and LPS. Antioxid Redox Signal, 9:1971-7 (2007).
Thannickal et al., Reactive oxygen species in cell signaling. Am J Physiol Lung Cell Mol Physiol.,279:L1005-28 (2000).
Thorand et al., Improved procedures for the palladium-catalyzed coupling of terminal alkynes with aryl bromides (Sonogashira coupling). J. Org. Chem., 63:8551-3 (1998).
Tietze et al., Efficient synthesis of branched propargyl- and allylsilanes. Synthesis, 1003-6 (1995).
Torssell, Nitrile Oxides, Nitrones, and Nitronates in Organic Synthesis. Novel Strategies in Synthesis, Wiley-VCH (1988).
Totter et al., Use of chemiluminescent compounds as possible indicators of radical production during xanthine oxidase action. J. Biol. Chem., 235:1839-42 (1960).
Tretter et al., Initiation of neuronal damage by complex I deficiency and oxidative stress in Parkinson's Disease. Neurochem. Res., 29:569-77 (2004).
Tsutsui et al., Mitochondrial oxidative stress and dysfunction in myocardial remodelling. Cardiovasc. Res. 81: 449-456 (2009).
Tu et al., Oxidative stress, mutant SOD1, and neurofilament pathology in transgenic mouse models of human motor neuron disease. Lab. Invest., 76:441-56 (1997).
Tufariello, Nitrones. 1,3 [One,Three]-Dipolar Cycloaddit. Chem. 2: 83-168 (1984).
Uppu et al., Acceleration of peroxynitrite oxidations by carbon dioxide. Arch. Biochem. Biophys. 327:335-43 (1996).
Valko et al., Free radicals and antioxidants in normal physiological functions and human disease, Int J Biochem Cell Biol., 39:44-84 (2007).
van Dam et al., The role of oxidative stress in neuropathy and other diabetic complications. Diabetes/Metab. Rev., 11:181-92 (1995).
Vanden Hoek et al., Significant Levels of Oxidants are Generated by Isolated Cardiomyocytes During Ischemia Prior to Reperfusion. Journal of Molecular and Cellular Cardiology, 29:2571-83 (1997).
Vasquez-Vivar et al., Superoxide anion formation from lucigenin: an electron spin resonance spin-trapping study, FEBS Lett., 403:127-130 (1997).
Vasquez-Vivar et al., Superoxide generation by endothelial nitric oxide synthase: the influence of cofactors. Proc. Natl. Acad. Sci. U. S. A. 95:9220-5 (1998).
Vaziri et al., Induction of oxidative stress by glutathione depletion causes severe hypertension in normal rats. Hypertension, 36:142-6 (2000).
Vieira et al., Hydroxyl radical induced damage to the purine bases of DNA: in vitro studies. J. Chim. Phys. Phys.Chim. Biol. 90:881-97 (1993).
Vignais, The superoxide-generating NADHP oxidase: structural aspects and activation mechanism. Cell. Mol. Life Sci. 59:1428-59 (2002).

(56) References Cited

OTHER PUBLICATIONS

Viner et al., Peroxynitrite modification of protein thiols: Oxidation, nitrosylation, and S-glutathiolation of functionally important cysteine residue(s) in the sarcoplasmic reticulum Ca-ATPase. Biochemistry, 38:12408-15 (1999).

Wei et al., ER and oxidative stresses are common mediators of apoptosis in both neurodegenerative and non-neurodegenerative lysosomal storage disorders and are alleviated by chemical chaperones. Hum. Mol. Genet., 17:469-77 (2008).

Wheeler et al., Absorption spectra of azo and related compounds. II. Substituted phenylnitrones, J. Am. Chem. Soc., 49:3127-33 (1984).

Wolff, Diabetes mellitus and free radicals. Free radicals, transition metals and oxidative stress in the etiology of diabetes mellitus and complications. Br. Med. Bull., 49:642-52 (1993).

Wood, The potential diagram for oxygen at pH 7. Biochem. J. 253:287-9 (1988).

Xu et al., ESR spin-trapping studies of free radicals generated by hydrogen peroxide activation of metmyoglobin. J. Agric. Food Chem. 38:1494-7 (1990).

Yamada et al., Transfer of the azido function from diphenylphosphoryl azide to malonic acid half esters. Tetrahedron Letters, 14:2343-6 (1973).

Yamazaki et al., Oxidation states of peroxidase. Mol. Cell. Biochem. 2:39-52 (1973).

Yan et al., Enhanced cellular oxidant stress by the interaction of advanced glycation end products with their receptors/binding proteins. J. Biol. Chem., 269: 9889-97 (1994).

Young et al., The occurrence of sleep-disordered breathing among middle-aged adults. N Engl J Med, 328:1230-5 (1993).

Zhang et al., Detection of superoxide anion using an isotopically labeled nitrone spin trap: potential biological applications. FEBS Lett., 473:58-62 (2000).

Zhao et al., Superoxide reacts with hydroethidine but forms a fluorescent product that is distinctly different from ethidium: potential implications in intracellular fluorescence detection of superoxide. Free Radical Biology and Medicine, 34:1359-68 (2003).

Zhao et al., Synthesis and biochemical applications of a solid cyclic nitrone spin trap: a relatively superior trap for detecting superoxide anions and glutathiyl radicals. Free Radical Biol. Med., 31:599-606 (2001).

Zielonka et al., Cytochrome c-mediated oxidation of hydroethidine and mito-hydroethidine in mitochondria: Identification of homo- and heterodimers. Free Radical Biol. Med., 44:835-46 (2008).

Zielonka et al., Detection of 2-hydroxyethidium in cellular systems: a unique marker product of superoxide and hydroethidine. Nat. Protoc., 3:8-21 (2008).

Zielonka et al., HPLC study of oxidation products of hydroethidine in chemical and biological systems: ramifications in superoxide measurements. Free Radical Biology and Medicine, 46:329-38 (2009).

Zielonka et al., Hydroethidine- and MitoSOX-derived red fluorescence is not a reliable indicator of intracellular superoxide formation: another inconvenient truth, Free Radic. Biol. Med., 48(8):983-1001 (2010).

Zielonka et al., Pulse radiolysis and steady-state analyses of the reaction between hydroethidine and superoxide and other oxidants. Archives of Biochemistry and Biophysics, 456:39-47 (2006).

Zielonka et al., The confounding effects of light, sonication, and Mn(III)TBAP on quantitation of superoxide using hydroethidine. Free Radical Biol. Med., 41:1050-7 (2006).

Zweier et al., The role of oxidants and free radicals in reperfusion injury. Cardiovasc. Res. 70:181-90 (2006).

\* cited by examiner

SILYLATED AZULENYL NITRONE SPIN TRAPS AS CHROMOTROPIC SUPEROXIDE DETECTORS

CROSS REFERENCE TO RELATED APPLICATIONS

The benefit under 35 U.S.C. §119 is claimed for U.S. Provisional Application No. 61/554,030, filed Nov. 1, 2011, the disclosure of which is incorporated by reference in its entirety.

INTRODUCTION

Increasing evidence of involvement of superoxide radical anion ($O_2.^-$) as a mediator of various pathological diseases,[1-3] and its importance in physiological processes led to the development of methods for detecting superoxide radical anion over the past decades. By far, the most commonly used probes include cyclic nitrones, hydroethidine, nitro blue tetrazolium, and other chemiluminescent and fluorescent species have received a criticism for various reasons.[4-7] To overcome the existing problem associated with these probes, an effective approach, a selective, mechanism-based colorimetric detection of superoxide anion has been developed by using a novel silylated azulenyl nitrone spin trap. The synthesized nitrones were found to trap superoxide anion, and hence, can be the potential biomarkers for superoxide production. The synthesized spin traps could offer a highly convenient method compared to other available colorimetric detection methods. This research describes the design, synthesis, chemical properties, testing and potential use of new silylated azulenyl nitrone compounds.

SUMMARY

Provided herein are compounds of formula (I) or (II), compositions of the same, and methods of using the same in trapping superoxide anion,

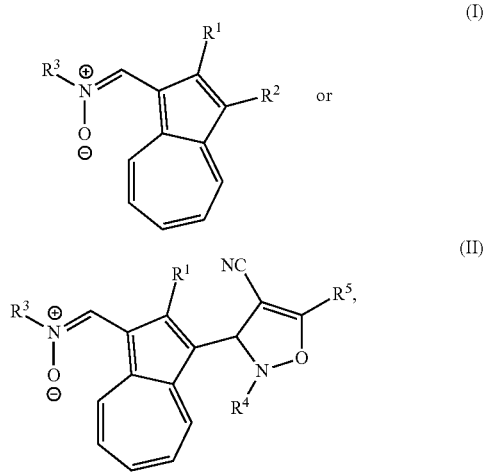

wherein $R^1$ is silyl; $R^2$ is CHO, alkyl, H, or —CH=N(O)—$R^6$; $R^3$ is alkyl; $R^4$ is H or alkyl; $R^5$ is alkyl, cycloalkyl, aryl, or heteroaryl, and $R^6$ is alkyl; or a salt, ester, hydrate or solvate thereof.

Methods disclosed herein using the compounds of formula (I) or (II) can be diagnostic and/or therapeutic. The compounds of formula (I) and (II) react with superoxide anion to form an adduct of the compound and superoxide anion. The resulting adduct can have absorbance properties different from the starting compound of formula (I) or (II), such as a different UV-Vis absorbance, color, or the like.

DEFINITIONS

"Alkyl" refers to a monovalent branched or unbranched saturated hydrocarbon group preferably having from 1 to about 11 carbon atoms, more preferably from 1 to 8 carbon atoms and still more preferably 1 to 6 carbon atoms. This term is exemplified by groups such as methyl, ethyl, n-propyl, isopropyl, n-butyl, isobutyl, tert-butyl, n-hexyl, n-octyl, tert-octyl and the like. The term "lower alkyl" refers to an alkyl group having from 1 to 11 carbon atoms. Alkyl groups can be substituted with 1 or more substituents, for instance from 1 to 5 substituents, and preferably from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkylene" refers to a divalent branched or unbranched saturated hydrocarbon group preferably having from 1 to 10 carbon atoms and more preferably from 1 to 6 carbon atoms. This term is exemplified by groups such as methylene (—CH$_2$—), ethylene (—CH$_2$CH$_2$—), the propylene isomers (e.g., CH$_2$CH$_2$CH$_2$— and —CH(CH$_3$)CH$_2$—) and the like.

"Alkynyl" refers to a monovalent branched or unbranched unsaturated hydrocarbon group preferably having from 2 to 10 carbon atoms and more preferably 2 to 6 carbon atoms and having at least 1 and preferably from 1-2 sites of carbon-carbon triple bond unsaturation. Preferred alkynyl groups include ethynyl (—C≡CH), propargyl (—CH$_2$C≡CH) and the like. Alkynyl groups can be substituted with 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Silyl" refers to a moiety with the following formula: —Si(R)$_3$, where R is individually selected from H, alkyl, and alkoxy. In some cases, each R is alkyl, and in more specific cases, each alkyl is the same. Non-limiting examples of silyl groups include TBDMS, TES, TMS, and TIPS.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, biphenyl, naphthyl and the like. Unless otherwise constrained by the definition for the individual substituent, such aryl groups can optionally be substituted with 1 or more substituents, for instance from 1 to 5 substituents, preferably 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Cycloalkyl" refers to a cyclic alkyl group of from 3 to 10 carbon atoms having a single cyclic ring or multiple condensed or bridged rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple or bridged ring structures such as adamantanyl and the like. The term "lower cycloalkyl" refers to a cycloalkyl group having from 3 to 6 carbon atoms. A cycloalkyl group can be substituted with 1 or more substituents, for instance from 1 to 5 substituents, and preferably from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, OCF$_3$, NO$_2$, CN, NC, OH, alkoxy, amino, CO$_2$H, CO$_2$alkyl, aryl, and heteroaryl. In some cases, the heteroaryl group is substituted with one or more of alkyl and alkoxy groups. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The term "alkoxy" used herein refers to straight or branched chain alkyl group covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

As used herein, the term "amino" refers to an unsubstituted, mono-substituted, or disubstituted nitrogen (e.g., —NH$_2$, NHR, or NR$_2$, where R is a substitution on the nitrogen). An ammonium group refers to a tri substituted nitrogen (e.g., —NR$_3$, where the nitrogen has a positive charge and R is a substitution on the nitrogen). The amino or ammonium group can be substituted with (e.g., the definition of R for the formulae directly above), with alkyl, alkenyl, alkynyl, aryl, alkylenearyl, heteroaryl, or the like.

The therapeutic methods and pharmaceutical compositions of the invention employ one or more azulenyl nitrones as the active agent. For the purposes of this invention, the nitrones of formula I are named using conventional nitrone nomenclature, i.e., the carbon atom of the carbon-nitrogen double bond (C=N) is designated the α-position and substituents on the nitrogen atom of the carbon-nitrogen double bond are given the N— prefix.

In some cases, the azulenyl nitrones of this invention may contain one or more chiral centers. Typically, such compounds will be prepared as a racemic mixture. If desired, however, such compounds can be prepared or isolated as pure stereoisomers, i.e., as individual enantiomers or diastereomers, or as stereoisomer-enriched mixtures. All such stereoisomers (and enriched mixtures) of the azulenyl nitrones of formula I are included within the scope of this invention. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

Additionally, all geometric isomers of the nitrone compounds of formula I are included within the scope of this invention including, for example, all isomers (i.e. E and Z isomers) of the carbon-nitrogen double bond of the nitrone functionality.

As used herein, the term "about" refers to a range of tolerance above or below a quantitative amount known to be acceptable to those of skill in the art. For instance, a dose of about 1000 mg indicates a dose typically administered under the guidance of a practitioner when a dose of 1000 mg is indicated. In certain embodiments, the term "about" refers to ±10% or ±5%.

Pharmaceutical Compositions

When employed as pharmaceuticals, the azulenyl nitrones of this invention are typically administered in the form of a pharmaceutical composition. Such compositions can be prepared in a manner well known in the pharmaceutical art and comprise at least one active compound. In preferred embodiments, the active compound is in purified form.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the active agent is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in Remington's Pharmaceutical Sciences.

In another embodiment, the pharmaceutical compositions can be in unit dose or unit of use forms or packages. As is known to those of skill in the art, a unit dose form or package is a convenient, prescription size, patient ready unit labeled for direct distribution by health care providers. A unit of use form contains a pharmaceutical composition in an amount necessary for a typical treatment interval and duration for a given indication.

A unit dosage form contains a pharmaceutical composition in an amount necessary for administration of a single dose of the composition. The present invention provides unit dosage forms of pharmaceutical compositions in an amount for delivery of a dose of about 0.1 to 125 mg/kg of the azulenyl nitrone to a subject. The subject can be, for example, a human subject with an average weight of about 80 kg. In certain embodiments, the present invention provides a unit dosage form that comprises about 10, 25, 50, 100, 500, 1000, 2000 or 2500 mg of the azulenyl nitrone. In certain embodiments, the unit dosage form consists essentially of these amounts of the azulenyl nitrone; in other words, the unit dosage form can additionally comprise other ingredients for administration of the azulenyl nitrone such as pharmaceutically acceptable carrier, excipient or diluent, a vial, syringe, or patch or other ingredients known to those of skill in the art for administering the azulenyl nitrone.

Typical unit dosage forms include prefilled, premeasured ampoules or syringes of the injectable compositions or unit dose wrapped tablets or capsules in the case of solid, oral compositions. The unit dosage form can be, for example, a single use vial, a pre-filled syringe, a single transdermal patch and the like.

As is known to those of skill in the art, a unit of use form or package is a convenient, prescription size, patient ready unit labeled for direct distribution by health care providers. A unit of use form contains a pharmaceutical composition in an amount necessary for a typical treatment interval and duration for a given indication. The methods of the invention provide for a unit-of-use package of a pharmaceutical composition comprising, for example, an azulenyl nitrone in an amount sufficient to treat an average sized adult male or female with about 10, 25, 50, 100, 500, 1000, 2000 or 2500 mg orally or 10, 25, 50, 500, 1000, 2000 or 2500 mg subcutaneously three times weekly for one month. Thus a unit of use package as described above would have twelve (three times per week injections for four weeks) prefilled syringes each containing 10, 25, 50, 500, 1000, 2000 or 2500 mg of azulenyl nitrone pharmaceutical composition.

The pharmaceutical compositions can be labeled and have accompanying labeling to identify the composition contained therein and other information useful to health care providers and subjects in the treatment of the diseases and/or disorders described above, including, but not limited to, instructions for use, dose, dosing interval, duration, indication, contraindications, warnings, precautions, handling and storage instructions and the like.

Role of Free Radicals in Various Diseases

Oxidative stresses due to free radicals have been implicated in various pathological conditions. The involvement of free radicals in disease is triggered by various factors such as genetic, environmental and disturbance of metabolic systems. Free radicals produced in mitochondria are widely believed to be the major cause of manifestation of a pro-oxidative shift in the plasma thiol/disulfide redox state which impairs glucose tolerance. These conditions are generally observed in cancer[119] and diabetes.[120] As in the other cases, the enhanced activity of NAD(P)H oxidase and xanthine-oxidase are the major cause of ROS generation derived from superoxide anion. These conditions are normally observed in chronic inflammation[121] and ischemia/reperfusion injury respectively.

An alteration of cellular thiol/disulfide redox state as a result of oxidative stress has been found in many cancer cells. Damage to DNA, occurs due to free radical-induced permanent modification of genetic materials, thereby leading to cell mutagenesis and carcinogenesis. An increased level of DNA damage has also been found in tumors which suggests the involvement of oxidative stress in the etiology of cancer. If DNA is severely damaged, then affected cells are selectively eliminated by the process called apoptosis. Apoptosis, a normal biological process, is a programmed cell death that destroys the damaged cells that could otherwise cause a threat to the integrity of organisms by leading to many morphological changes.[122] However, uncontrolled apoptosis can lead to the destruction of healthy cells.[123] The consequences of DNA damage are arrest or induction of transcription, induction of signal transcription pathways, genomic instability, and replication error; all of them are associated with carcinogenesis.[124,125] The formation of the DNA oxidation product, 8-oxo-7-hydro-29-deoxyguanosine (8-oxo-dG), has been studied most extensively as a potential biomarker of carcinogenesis because it is easily detectable. 8-oxo-dG was first detected in urine by Shigenaga et al[126] Tobacco smoking is one of the sources of carcinogenic reactive oxygen species.[127]

Free radicals are also involved in diabetes mellitus.[29,128] Hyperglycemia is the common characteristic of both type-1 diabetes mellitus (insulin-dependent) and type-2 diabetes mellitus (non-insulin-dependent). Hyperglycemia is the condition in which an excessive amount of glucose is circulated in the blood plasma. Increased glucose levels are shown to increase the production of free radicals from various sources. The major site of superoxide anion formation in diabetes is mitochondrial complex II[129] which is different from the sites mitochondrial complex I and the ubiquinone-complex III that generate superoxide anion under normal conditions. Glucose auto-oxidation has been shown to produce superoxide anion in diabetic patients[130,131] The advanced glycation end (AGE) products are the result of glucose oxidation which interact with specific cell surface binding proteins with subsequent generation of ROS.[132] The increased level of ROS may cause the development of diabetic complications such as accelerated atherosclerosis[133] and other vascular pathologies.[134]

Various inflammatory diseases are associated with the elevated production of ROS.[135] Atherosclerosis is one of the chronic inflammatory diseases that is characterized by hardening and thickening of the arterial walls that develop in the inner coat.[136] In the presence of hyperlipidemia, oxidative stress may activate the genes that induce an inflammatory response to the vascular endothelium. The injured endothelial cells then stimulate the recruitment of mononuclear cells into the arterial walls which bind oxidized low-density lipoprotein (LDL) resulting in abnormal macrophages, that subsequently undergo apoptosis. The massive apoptosis of macrophages causes the formation of atherosclerotic plaque.[137] Moreover, experimental data shows that hypertension may cause an intensification of atherosclerosis.[138]

A role for oxidative stress in hypertension has been supported by the study of an animal model by Vaziri et al[139] via in vivo glutathione depletion. Similarly, a potential causative role for oxidative stress is also found in patients with essential hypertension.[140,141] The mechanism that seems to contribute to hypertension is increased generation of superoxide anion in the vessel wall followed by the formation of peroxinitrite anion,[142] which in turn, increases vasoconstriction.[143] In vivo studies in animals demonstrated that angiotensin II is the main factor that is involved in the oxidative stress that leads to a chronic high blood pressure.[144,145]

It is suggested that oxidative stress is also involved in several neurodegenerative diseases. Among the other organs, brain and nervous tissue suffer more oxidative damages. The reason for this is the large amount of oxygen consumption in a relatively small tissue mass (brain) and a high content of oxidizable polyunsaturated fatty acids. Brain has a high iron content[146] that can be released as ions during brain injury, and these ions are capable of catalyzing free radical reactions resulting in HO. formation which thereby accelerates lipid peroxidation and autoxidation of neurotransmitters.

Alzheimer's disease (AD) is a neurodegenerative disease characterized by impairment of higher cognitive functions and extensive neuronal loss. Two pathological features found in AD patients are the accumulation of amyloid plagues (amyloid-β peptide) in the brain and the presence of neurofibrillary tangles and neuropil threads.[147] A progressive cerebral accumulation of amyloid-β peptide is the major event in the development of Alzheimer's disease. This accumulation causes neurofibrillary damage in neurons, neurotransmitter defects and neuronal death. These phenomena are the major cause of loss of cognitive functions.[111] The evidence of increased lipid peroxidation and decreased polyunsaturated fatty acids content, increased protein and DNA oxidation, increased formation of 4-hydroxynonenal (product of lipid peroxidaiton) in AD ventricular fluids, the presence of advanced glycation end products, malondialdehyde, nitrotyrosine, and peroxynitrite in neurofibrillary tangles supports the involvement of oxidative stress in the brains of Alzheimer's disease brain victims.[147,148] The significant amount of lipid peroxidation has been implicated by the increased level of 4-hydroxynonenal in the postmortem cerebrospinal fluid of Alzheimer's disease patients.[149] Individuals with Down's syndrome have been shown to develop Alzheimer's disease as they get older.[150] Down's syndrome is a genetic disease due to the presence of three copies of chromosome 21 that leads to mental retardation. There is evidence of overexpression of Cu/ZnSOD in Down's syndrome that may result in increased production of hydrogen peroxide.[28] Overproduction of Cu/ZnSOD in transfected cells appears to promote increased lipid peroxidation.[151]

Parkinson's disease (PD) is characterized by a problem in controlling movement that includes slow movement of foot and hand when they are at rest and muscle rigidity. PD is associated with a selective loss of neurons in a part of the midbrain called the substantia nigra.[93] The cells of the substantia nigra produce dopamine, a neurotransmitter-chemical messenger between brain and nerve cells, which communicates with cells in another region of the brain. It is believed that oxidative stress is an initiator of dopaminergic cell degeneration which is also associated with the presence of Lewy bodies in the substantia nigra and elsewhere based on the postmortem.[60,152] Lewy bodies are small spherical proteins which affect the brain's normal functions and interrupt the action of important chemical messengers.

Similarly, in Amyotrophic lateral sclerosis (ALS), motor neurons are the main targets affected in the motor cortex, spinal cord and brain stem[153] which leads to muscle tone impairment, respiratory failure, paralysis, and often death. Multiple mutations are associated with familial ALS. Studies show that 20% of familial ALS patients carry mutations in the Cu/ZnSOD gene, suggesting the involvement of free radicals.[154] One hypothesis concerning the etiology of ALS is that metals at the active sites of mutant Cu/ZnSODs allow these enzymes to catalyse oxidation reactions via peroxynitrite-generated nitrating species.[155] Several lines of transgenic mice overexpressing mutant Cu/ZnSOD have shown to develop a motor neuron disease, whose pathology and mode of progression resemble familial ALS patients. Gurney, Becker et al. used azulenyl nitrone (AZN) to suggest oxidative stress in SOD mutant transgenic mice.[156] Recently, Siddque's team discovered mutation in ubiquilin 2 gene in the brains and in the spinal cords of ALS victims.[157] The mutant ubiquilin 2 gene causes the accumulation of damaged protein contributing several forms of ALS.

Other neurodegenerative diseases contributed to oxidative stress may include, Huntington's disease,[158] multiple sclerosis,[159] neuronal ceroid lipofuscinoses[160] and Friedreich's ataxia.[161]

Injury to heart, brain, lungs, intestine, liver, kidney and skeletal muscle resulting from ischemic/reperfusion may present in a variety of clinical conditions such as organ transplantation, stroke, myocardial infractions, and many other situations.[162-164] On the basis of hospital discharge records, 5 million patients (16.2%) were diagnosed with ischemic cardiovascular events and such events were the major cause of death (38.7%) in the United States.[165] Occurrence of tissue damage is attributed to the large amount of ROS production during ischemia/reperfusion.[166] Under the ischemic condition (oxygen deprivation), xanthine dehydrogenase is converted into xanthine oxidase that utilizes oxygen, which in turn, depletes ATP leading to the accumulation of the purine catabolite hypoxanthine. Upon subsequent reperfusion (reoxygenation), xanthine oxidase uses the influx of oxygen to oxidize hypoxanthine into xanthine with rapid generation of superoxide anion and hydrogen peroxide.[167] Treatment with a synthetic SOD mimetic has been shown to attenuate tissue damage in a rat model of ischemia/reperfusion injury.[168]

Obstructive sleep apnea is a breathing disorder among adults, characterized by an abnormal pause in breathing during sleep.[169] The resulting repeated hypoxia and reoxygenation is similar event to the conditions of ischemia/reperfusion. Untreated and severely affected individuals often develop cardiovascular diseases such as coronary artery disease, arterial hypertension and cerebrovascular disease[170] that are associated with increased mortality.[171] The involvement of free radicals in obstructive sleep apnea, which could be the cause of the associated cardiovascular events, has been implicated by the detection of increased production of superoxide anion from polymorphonuclear neutrophils in affected patients after exposure to various stumuli.[172]

Most of the free radical mediated diseases, such as neurodegenerative, cardiovascular and some common forms of cancer, increase with age. Aging is a process of progressive loss in the efficiency of physical and cognitive functions of an organism after the reproductive phase of life. The fact that free radicals cause deleterious damage to cells over time which results in aging was proposed by Harman et al.[11] Several studies also support his theory by showing progressive generation of free radicals and almost exponential increases in accumulation of oxidatively damage proteins, lipids and DNAs during aging.[173-175] Mitochondria are the primary sites of generation of oxidants during the aging process. Much of the oxidized DNAs, especially the nuclear DNA, are repaired by the cell but the mitochondrial DNA receives only low repair activity.[176] Over time, the damaged mitochondrial DNA accumulates and slowly shuts down mitochondria causing cell to age and eventually die.

Methods of Treatment and Prevention

The present azulenyl nitrones are used as therapeutic agents for the treatment of conditions in mammals. Accordingly, the compounds and pharmaceutical compositions of this invention find use as therapeutics for preventing and/or treating oxidative, ischemic, and ischemia/reperfusion-related and chemokine-mediated conditions in mammals including humans. Ischemia and ischemia/reperfusion-related conditions include neurological conditions and cardiovascular conditions as described below.

In a method of treatment or prophylaxis aspect, this invention provides a method of treating or prohpylaxing a mammal susceptible to or afflicted with a neurological condition such as stroke, multi-infarct dementia, traumatic brain injury, spinal cord injury, diabetic neuropathy or neurological sequelae of surgical procedures, which method comprises administering an effective amount of one or more of the pharmaceutical compositions just described. Neurological sequelae of surgical procedures include those sequelae of surgical procedures known to those of skill in the art such as neurological sequelae following procedures using a heart or a lung machine. In particular embodiments, the present invention provides methods of treating or preventing stroke with any compound of the invention.

In yet another method of treatment or prophylaxis aspect, this invention provides a method of treating or prophylaxing a mammal susceptible to or afflicted with a cardiovascular condition such as myocardial infarction, angina or a non-neurological organ or tissue injury following ischemia, which method comprises administering an effective amount of one or more of the pharmaceutical compositions just described. Non-neurological organ or tissue injury following ischemia include those conditions known to those of skill in the art to follow decreased blood flow or reperfusion following ischemia such as kidney ischemia, muscle ischemia, and the like.

In a further method of treatment or prophylaxis aspect, this invention provides a method of treating or prophylaxing a mammal susceptible to or afflicted with a condition related to chemokine function such as a neurodegenerative disease, a peripheral neuropathy, an infection, a sequela of an infection, or an autoimmune disease, which method comprises administering an effective amount of one or more of the pharmaceutical compositions just described.

Compounds that inhibit chemokine activity or function may be used for the treatment of diseases that are associated with inflammation, including but not limited to, inflammatory or allergic diseases such as asthma, allergic rhinitis, hypersensitivity lung diseases, hypersensitivity pneumonitis, eosinophilic pneumonias, delayed-type hypersensitivity, interstitial lung disease (ILD) (e.g., idiopathic pulmonary fibrosis, or ILD associated with rheumatoid arthritis, systemic lupus erythematosus, ankylosing spondylitis, systemic sclerosis, Sjögren's syndrome, polymyositis or dermatomyositis); systemic anaphylaxis or hypersensitivity responses, drug allergies, insect sting allergies; autoimmune diseases, such as rheumatoid arthritis, psoriatic arthritis, systemic lupus erythematosus, myastenia gravis, juvenile onset diabetes; glomerulonephritis, autoimmune throiditis, Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Cicatricial Pemphigoid, CREST Syndrome, Cold Agglutinin Disease, Crohn's Disease, Discoid Lupus, Essential Mixed Cryoglobulinemia, Fibromyalgia-Fibromyositis, Graves' Disease, Guillain-Barre, Hashimoto's Thyroiditis, Idiopathic Pulmonary Fibrosis, Idiopathic Thrombocytopenia Purpura, IgA Nephropathy, Insulin-dependent Diabetes, Juvenile Arthritis, Lichen Planus, Lupus, Ménière's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjögren's Syndrome, Stiff-Man Syndrome, Takayasu Arteritis, Temporal Arteritis/Giant Cell Arteritis, Ulcerative Colitis, Uveitis, Vasculitis, Vitiligo, Wegener's Granulomatosis, Churg-Strauss Syndrome, Atopic Allergy, Autoimmune Atrophic Gastritis, Achlorhydra Autoimmune, Cushings Syndrome, Dermatomyositis, Erythematosis, Goodpasture's Syndrome, Idiopathic Adrenal Atrophy, Lambert-Eaton Syndrome, Lupoid Hepatitis, Lymphopenia, Phacogenic Uveitis, Primary Sclerosing Cholangitis, Schmidt's Syndrome, Sympathetic Ophthalmia, Systemic Lupus Erythematosis, Thyrotoxicosis, Type B Insulin Resistance, Autoimmune ureitis, Autoimmune oophoritis and orchitis, Dermatitis herpetiformis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

In addition compounds that activate or promote chemokine receptor function can be used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to helminth infections, such as nematodes (round worms); Trichuriasis, Enterobiasis, *Ascariasis*, Hookworm, Strongyloidiasis, Trichinosis, filariasis; trematodes; visceral worms, visceral larva migtrans (e.g., Toxocara), eosinophilic gastroenteritis (e.g., *Anisaki* spp., *Phocanema* ssp.), cutaneous larva migrans (*Ancylostona braziliense, Ancylostoma caninum*); the malanra-causing protozoan *Plasmodium vivax*, Human cytomegalovirus, Herpesvirus saimiri, and Kaposi's sarcoma herpesvirus, also known as human herpesvirus 8, and poxvirus *Moluscum contagiosum*.

In certain embodiments, the present invention provides any compound of the invention for use in the manufacture of a medicament. In further embodiments, the present invention provides any compound of the invention for use in the manufacture of a medicament for the treatment or prevention of any condition identified herein. For instance, the present invention provides any compound of the invention for use in the manufacture of a medicament for the treatment and/or prevention of oxidative, ischemic, and ischemia/reperfusion-related and chemokine-mediated conditions in mammals including humans. Such conditions are described in detail herein.

Compounds of the present invention may be used in combination with any other active agents or pharmaceutical compositions where such combined therapy is useful to modulate chemokine receptor activity and thereby prevent and treat inflammatory and immunoregulatory diseases.

Injection dose levels range from about 0.1 mg/kg/hour to at least 15 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 25 g/day for a 40 to 80 kg human patient. The present invention provides doses from about 0.1 mg to about 25 g per day for an 80 kg human patient. In particular embodiments, the present invention provides doses from about 0.1 mg to about 20 g per day, from about 0.1 mg to about 10 g per day, from about 0.1 mg to about 5 g per day, from about 0.1 mg to about 1 g per day, and from about 0.1 mg to about 0.5 g per day. Preferred doses for ischemic conditions include from about 0.1 mg to about 10 g per day, from about 50 mg to about 10 g per day, from about 100 mg to about 10 g per day, and from about 100 mg to about 1 g per day. Preferred doses for chemokine mediated disorders include from about 0.1 mg to about 10 g per day, from about 10 mg to about 1000 mg per day, and from about 100 mg to about 1000 mg per day.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 65 mg/kg of the azulenyl nitrone, with preferred doses each providing from about 0.1 to about 20 mg/kg, about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the azulenyl nitrones of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other active azulenyl nitrones.

Silylated Azulenyl Nitrones

The objectives of this research are to design and synthesize various novel silylated azulenyl nitrones as spin traps for chromotropic detection of superoxide anion radical, to study their chemical properties and to study their reaction with superoxide anion. Towards this aim, the following nitrones were pursued.

Nitrones are known as good candidates to react with superoxide anion by spin trapping yielding detectable diamagnetic spin adducts. A silyl substituent, a non-polar, oxophilic, electropositive group, has a strong propensity to react with an oxygen anion such as that which is present in a superoxide spin adduct. Hence, the presence of a nearby silyl group in nitrone molecules is expected to confer distinctive reaction pathways with superoxide that are not available in traditional nitrones. Moreover, due to colorimetric properties of azulene compounds, the end products of the spin trapping would likely yield characteristically colored molecules. Hence, the following silylated azulenyl nitrones 22, 23 and 24 are putatively equipped specifically for superoxide anion detection by likely yielding characteristically colored end products with a characteristic UV-VIS spectral profile upon reaction with superoxide anion.

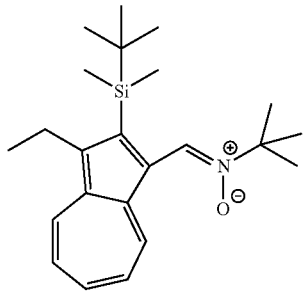

Compound 22

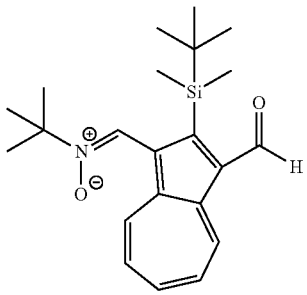

Compound 23

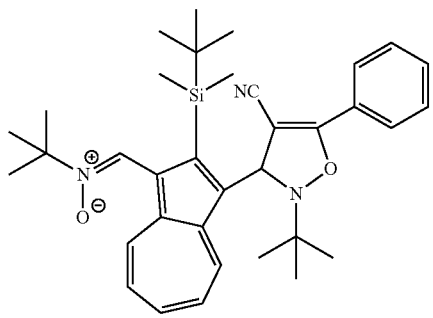

Compound 24

Mitochondria-Targeted Silylated Azulenyl Nitrones:

Mitochondria are the major sites of superoxide production. To detect mitochondrial superoxide, the chemical structure of compound 24 was modified by incorporation of a guanylhydrazone moiety. Since guanylhydrazones are protonated at physiological pH, the attachment of this moiety to compound 24 is expected to increase the permeability of compound 25 into the mitochondrial membrane to reach sites of superoxide anion generation. The structure of compound 25 is given below:

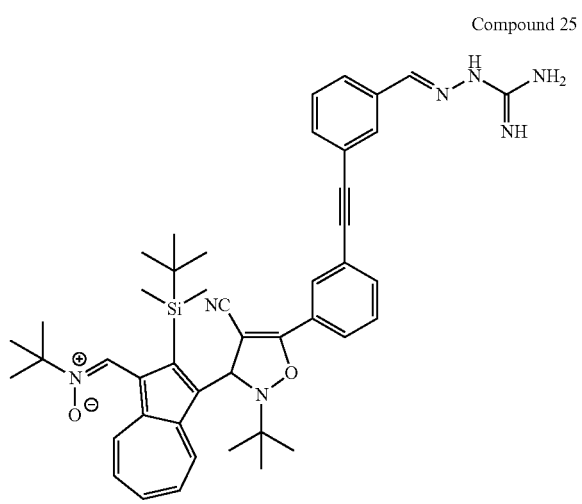 [SMILES: CC(C)(C)N1OC(c2cccc(C#Cc3cccc(/C=N/NC(=N)N)c3)c2)=C(C#N)C1c1c2cccccc-2c(/C=[N+](\[O-])C(C)(C)C)c1[Si](C)(C)C(C)(C)C]

Compound 25

Synthesis of Azulenylsilane Nitrones:

Nitrones have been shown to exhibit an efficient antioxidant activity in vitro and likely in vivo by trapping reactive free radicals.[207,271] Due to their spin trapping properties, numerous nitrones have been developed for detecting superoxide anion in biological systems in assays that require ESR spectroscopy. Superoxide adducts thereby formed were found to be very unstable and this reduced persistence complicates their detection by ESR. The research project described here was to synthesize silylated azulenyl nitrones for superoxide detection that could selectively yield a characteristic product after the oxidation reaction with superoxide anion, which could be detected by UV-VIS and simple colorimetric techniques without using ESR spectroscopy.

Synthesis of Ethylated Azulenylsilane Mononitrone 22:

The first synthetic effort in the preparation of ethylated azulenylsilane nitrone (22) involved four efficient steps starting from commercially available 3-hexyne as illustrated in scheme 1. Allenylsilane (27) was prepared in one step employing a metalation reaction according to the method reported in the literature.[272] The metalation reaction was carried out by the addition of 3-hexyne to a cooled sec-BuLi solution in THF and left for 3 hr which formed the monolithiated product. The metalation mixture was then silylated by treatment with excess tert-butyldimethylsilylchloride at −70° C. and then left overnight at room temperature (10%). Danheiser and Becker reported the preparation of several azulenylsilanes via cyclization reaction between allenylsilanes and tropylium cations.[273] Following the same protocol, azulenylsilane (28) was synthesized by addition of 2.2 equiv. of tropylium tetrafluoroborate and 3.3 equiv. of poly-4-vinylpyridine in acetonitrile (53%) which underwent (3+2) annulation involving rearrangement and cyclization. Attempted oxidation of the 1-ethyl and 3-methy group of azulene (28) by treatment with 4 equiv. of 2,3-dichloro-5,6-dicyanobenzoquinone (DDQ)[274] failed to give the expected ketoaldehyde (29). Instead the unexpected product ethyl aldehyde (30) in 53% yield and the by product alcohol (31) were obtained based on NMR data. It is obvious from the product that partial oxidation might have taken place due to steric hindrance of the silyl group and its substituents. It was possible to optimize the yield of ethylaldehyde (30) from 53% to 70% using only 2 equiv. of DDQ for oxidation reaction. In one attempt, during the preparation of aldehyde (30), approximately 2.5% of bisaldehyde (32) was also recovered. Condensation of ethylaldehyde (30) with N-tert-butylhydroxylamine hydrochloride in pyridine at 45° C. ethylated azulenylsilane nitrone (22) in 47% yield.

Scheme 1. Synthesis of azulenylsilane ethylnitrone 22

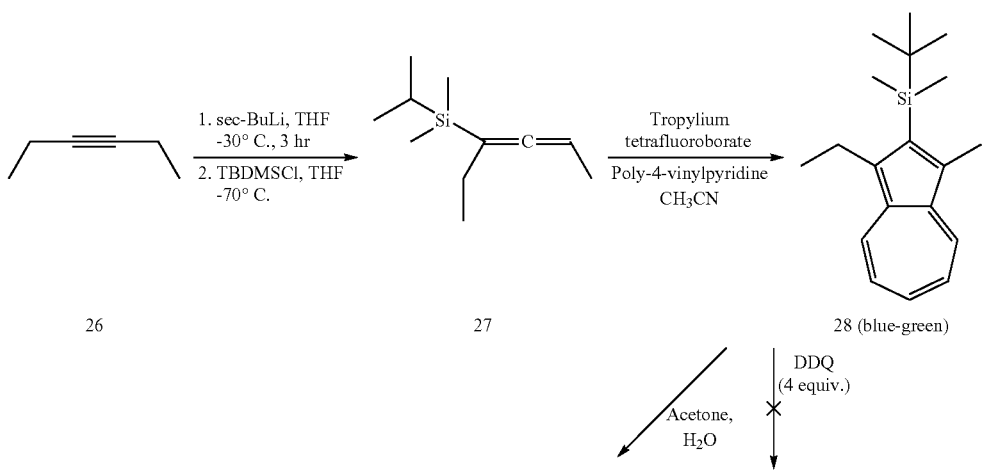

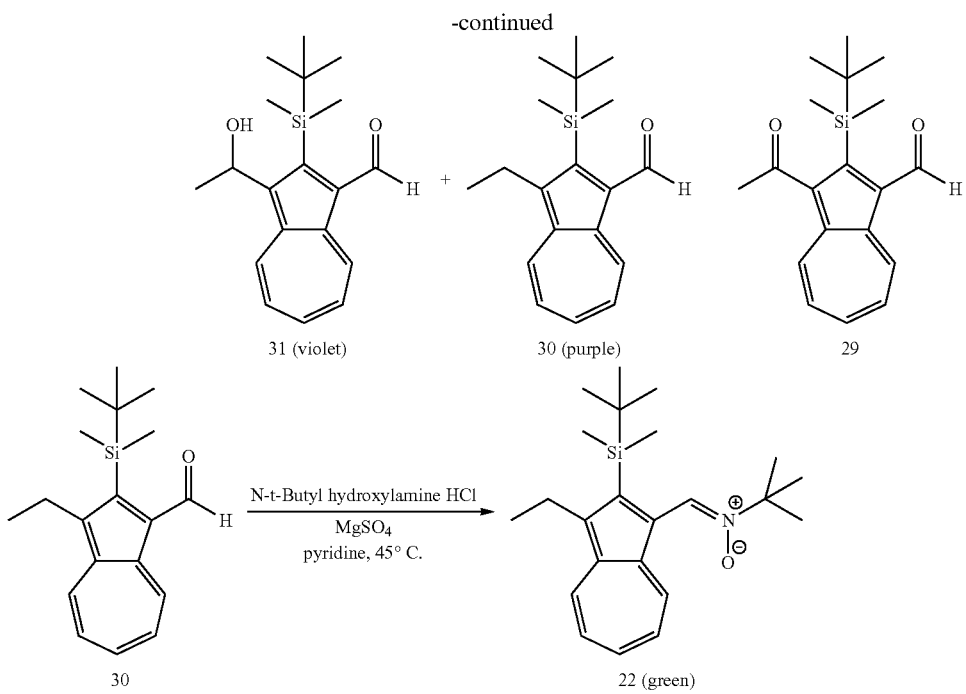

Synthetically, bis-aldehyde 32 was a desirable intermediate for the synthesis of other compounds. For example, compound 32 would prove to be a useful precursor for the preparation of other nitrones that might have significance in trapping superoxide anion (vide infra). Keeping this in mind, efforts were made to synthesize 32 efficiently.

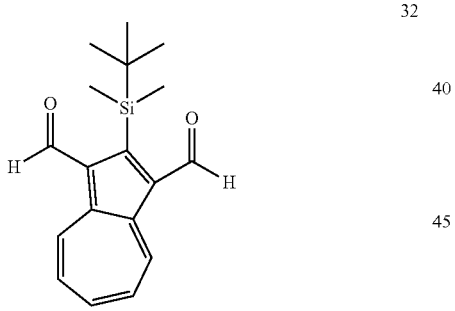

Synthesis of Azulenylsilane Carboxaldehyde Nitrone:

In an attempt to synthesize mononitrone (23) from the red aldehyde 32, readily available acetaldehyde (33) was used as the starting material. N-tert-butylimine (35) was prepared from addition of acetaldehyde to tert-butylimine (34) at 0° C. (without any solvent) followed by distillation according to the modified method of Chancel[275,276] as illustrated in scheme 2. The N-tert-butylimine (35) was then deprotonated with LDA and silyated by using TBDMSCl followed by repeated deprotonation with BuLi, and methylation with iodomethane which afforded mono methylated α-silylimine (36) in a one-pot process reported by Tietze.[277] The methylated silyimine (36) is quite unstable and was easily hydrolyzed by washing through a silica gel column using petroleum ether and ethylacetate which gave aldehyde (37). A Corey-Fuchs reaction involving the treatment of aldehyde (37) with a mixture of triphenylphosphine and tetrabromomethane in $CH_2Cl_2$ at 0° C. provided dibromoalkene (38) via a Wittig-like reaction.

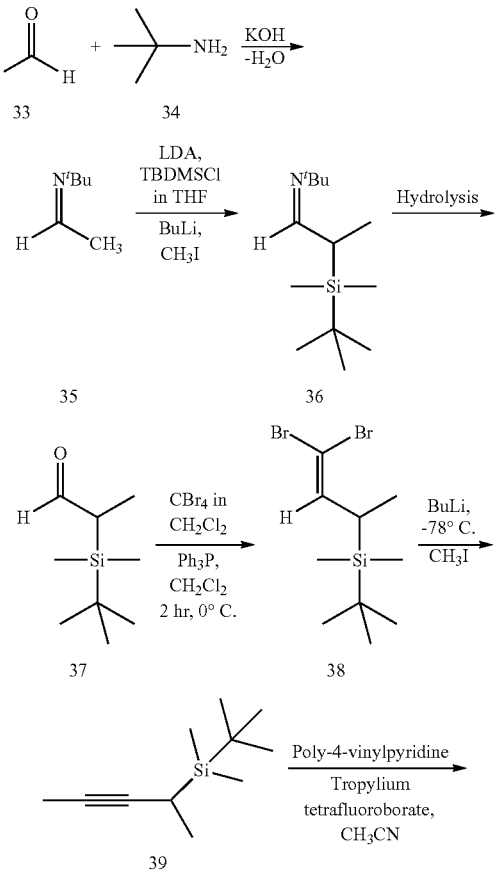

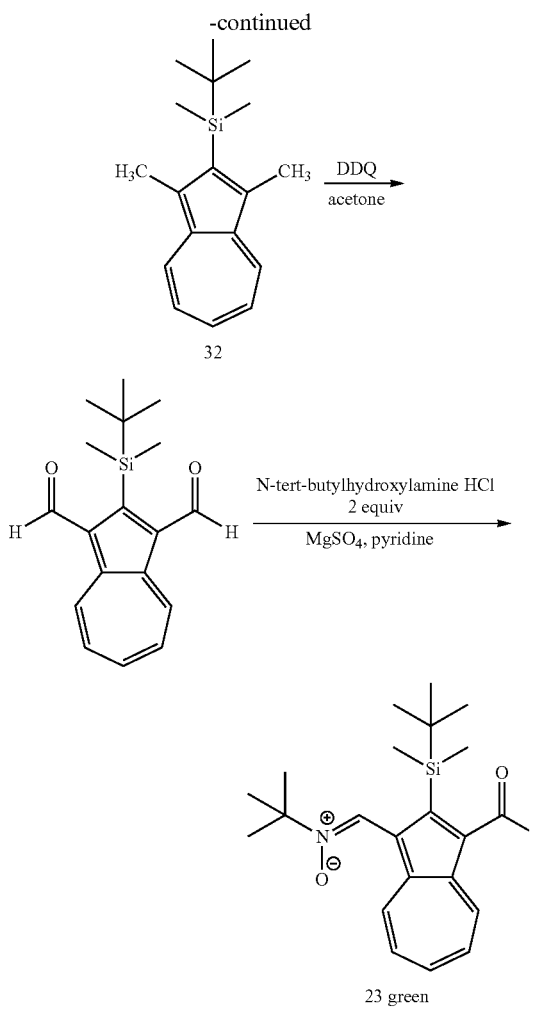

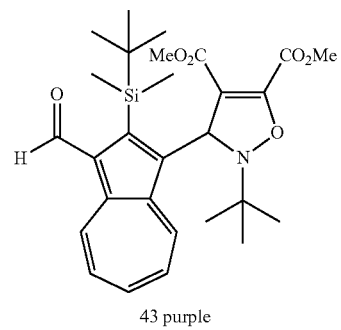

Subsequently, treatment of dibromoalkene (38) with BuLi followed by exposure to iodomethane yielded alkynylsilane (39) via the generation of a bromoalkyne intermediate that formed in a process consisting of dehydrohalogenation and metal-halogen exchange. A (3+2) annulation reaction between alkyneylsilane (39) and tropylium tetrafluoroborate in acetonitrile in the presence of excess poly-4-vinylpyridine resulted in formation of blue azulenylsilane (40).[273] Oxidation of two methyl groups of azulenylsilane (40) with four equivalents of DDQ[274] in the presence of acetone afforded bis-aldehyde (32) which was converted into the ethylated azulenylsilane mononitrone (23) by reaction with two equivalents of N-tert-butylhydroxylamine hydrochloride in pyridine at 45° C.

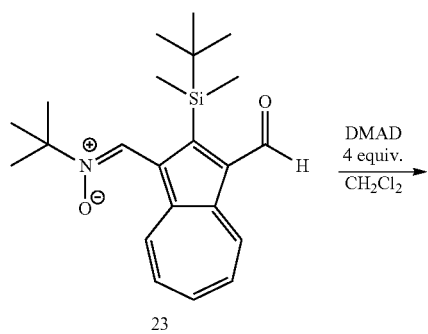

Unfortunately, the reaction failed to give the expected product when nitrone 23 was treated with 4 equivalent of DMAD. Instead, the intermediate product 43 was obtained, illustrated in scheme 4, which was identified by NMR data. Failure to achieve the formation of triester 43 suggests that only one equivalent of DMAD had been consumed in a 1,3-dipolar cycloaddition reaction to afford cyaloaddition adduct 43, which thereafter failed to open the isoxazoline ring to rearrange to azomethine ylide before a second cycloaddition reaction with another equivalent of DMAD could occur.

The condensation reaction between aminofuran derivative 50 and N-tert-butylhydroxylamine hydrochloride in pyridine at 45° C. afforded aminofuran nitrone 49.

With the successful synthesis of aminofuran nitrone, an attempt was made to improve hydrophilicity by modifying compound 49 in order to detect superoxide generated in mitochondria. The incorporation of a guanylhydrazone moiety was sought as a means of increasing hydrophilicity. Since a guanylhydrazone is positively charged at physiological pH, it may traverse across cellular membranes and therefore aid in the accumulation of nitrone into mitochondria.

Scheme 6. Synthesis of aminofuran nitrone 49

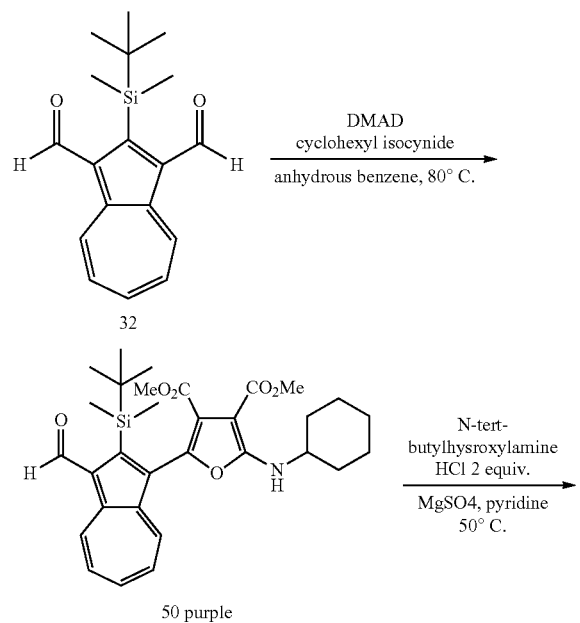

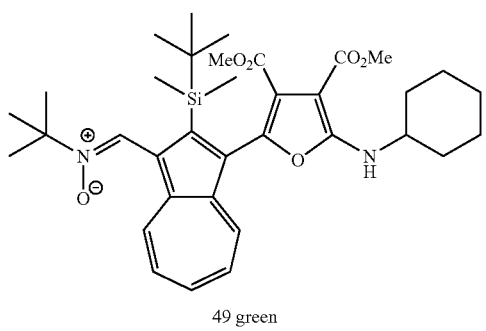

49 green

Azulenylsilane dinitrone 55 was found to be a useful precursor for the synthesis of other nitrones which allowed incorporation of other substituents on either the 1 or 3 position via a cycloaddition approach (vide infra). A simple condensation reaction between mononitrone 23 and three equivalents of N-tert-butylhydroxylamine hydrochloride in pyridine at 45° C. yielded azulenylsilane dinitrone 55. It was also possible to prepare this dinitrone in 33% yield from bis-aldehyde 32 by using five equivalent of N-tert-butylhydroxylamine hydrochloride as outlined in the scheme 8.

One of the possibilities to introduce an electron withdrawing cyano moiety to the azulenylsilane nitrone is a 1,3-dipolar cycloaddition approach using dinitrone 55. Coates, who has studied the regioselective cycloaddition between and cyclic nitrones with various alkene nitriles and alkyne nitriles, demonstrated successful formation of cycloadducts using phenylpropiolonitrile.[288] Using the same protocol, isoxazoline nitrone, 24 was prepared regio specifically from dinitrone 55 and phenylpropiolonitrile in benzene at 50° C. for 6 days (scheme 9).

Initially, the product nitrone 24 was thought to undergo ring opening of the isoxazoline system to produce enamine derivative 56 on basis of an the earlier study.[289] But such rearrangement was not observed in this case (figure 14).

Scheme 9. Synthesis of isoxazoline nitrone 24

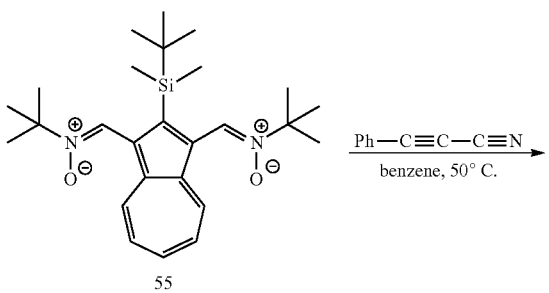

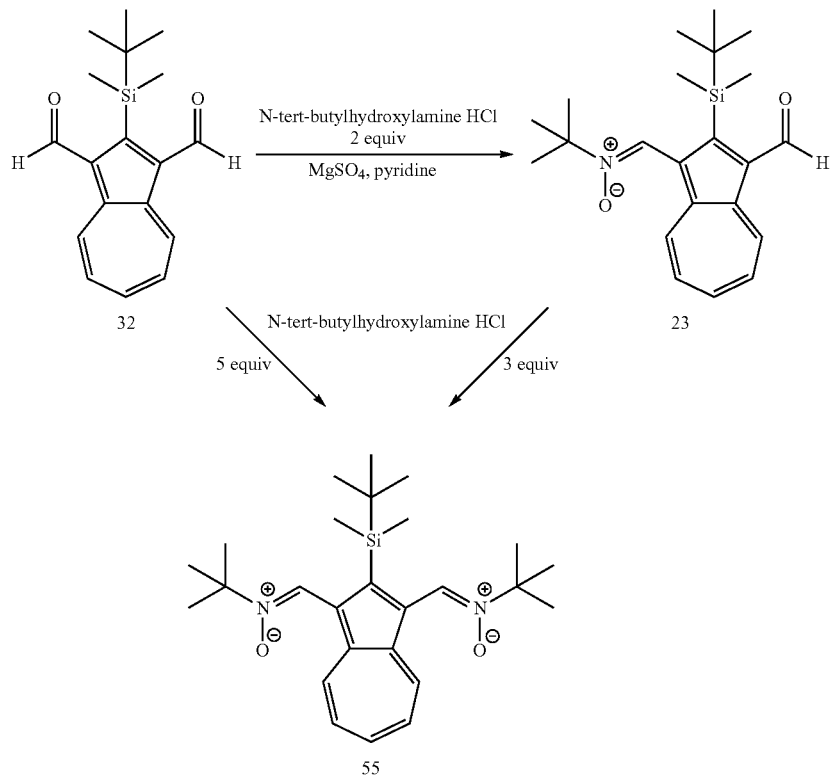

-continued

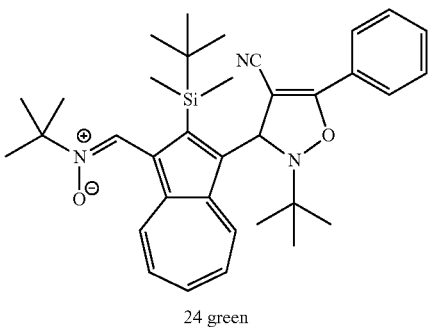

24 green

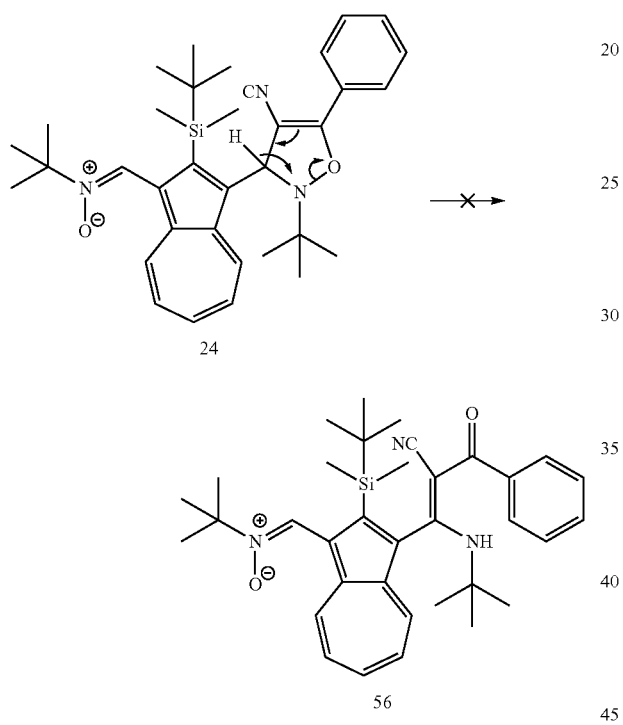

24

56

Figure 14. Expected Product 56 Via Ring Opening

Isoxazoline nitrone 24 seemed to be a promising agent for in vitro superoxide detection. However, the drawback to this compound is that it is not a lipophilic cation Scheme 11. Synthesis of [3-(3-Formyl-phenylethynyl)-phenyl]-propyne nitrile 61

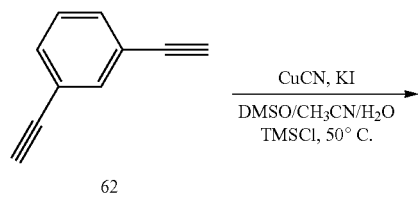

62

-continued

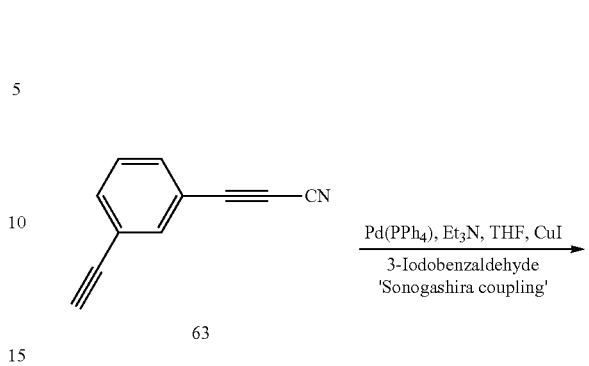

63

61 which limits towards its accumulation in mitochondria. Therefore, effort has been made to enhance its mitochondriotropic activity by incorporating a guanylhydrazone moiety. This plan resulted in the preparation of guanylhydrazone nitrone 25 from [3-(3-Formyl-phenylethynyl)-phenyl]-propyne nitrile 61.

Aldehyde 61 was prepared in two steps as shown in scheme 11. According to the method reported by Wang,[294,295] cyanation of one terminal acetylene of 1,3-diethynylbenzene 62, using two equivalents of cuprous cyanide in the presence of TMSCl, water and a catalytic amount of sodium iodide at 50° C. afforded nitrile derivative 63. The crucial factor in this cyanation process was the composition of solvent. Thus, DMSO and a co-solvent ($CH_3CN$) should be in the ratio of 3:1. Sonogashira coupling of compound 63 with 3-iodobenzaldehde[296] in THF using tetrakistriphenylphosphine palladium at room temperature for 24 hour provided [3-(3-Formyl-phenylethynyl)-phenyl]-propyne nitrile 61. Treatment of one equivalent of nitrile 61 with dinitrone 55 in benzene at 50° C. engendered 1,3-dipolar cycloaddition that provided adduct 64. A condensation reaction between compound 64 with aminoguanidine hydrochloride in the presence of triethylamine in pyridine at 45° C. afforded guanylhydrazone nitrone 25 (scheme 12).

Scheme 12. Synthesis of guanylhydrazone nitrone 25
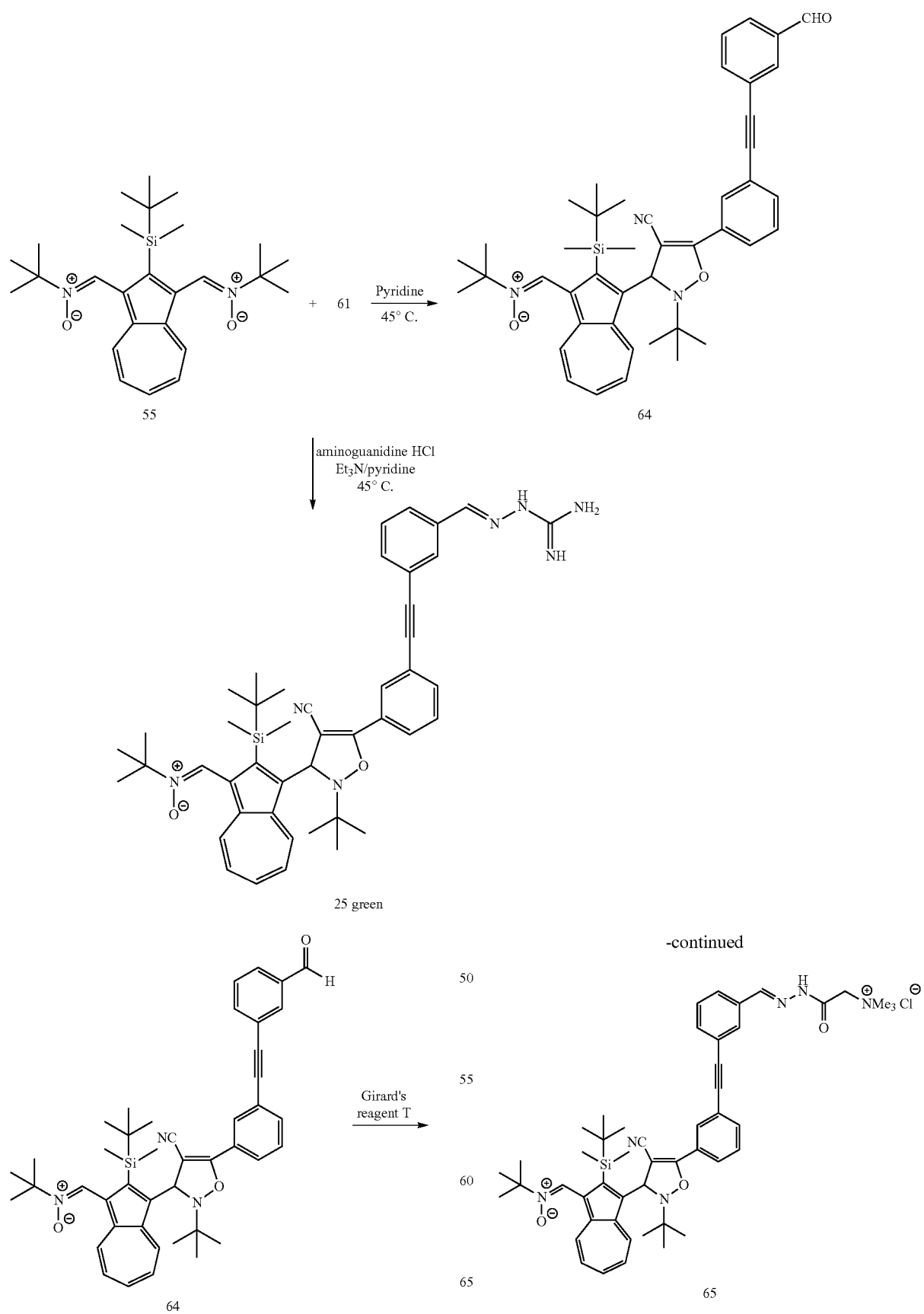

Figure 15. Synthetic Scheme of Compound 65

Unfortunately, nitrone 25, despite the presence of the polar guanylhydrazone, is found to be poorly water soluble (but could still be mitochondriotropic). Another possibility of making mitochondria-targeted compounds involves the synthesis of salts of nitrones 65 and 66. The presence of the aldehyde group in compound 64 is ideal for such a purpose. Nitrone 65 could theoretically be prepared by treatment of aldehyde 64 with Girard's reagent as shown in figure 15. Alternatively, transformation of aldehyde 64 into salt 66 could proceed in several steps as illustrated in figure 16. First, a reduction reaction converts aldehyde 64 into the alcohol derivative which upon treatment with tosylchloride would give the corresponding tosylate congener. Subsequently, $S_N{}^2$ reaction of the tosylate with triphenylphosphine would afford the potential mitochondriotropic phosphonium salt 66.

The first attempt to detect superoxide involved reaction of nitrone 22 with potassium superoxide in the presence of 18-crown-6 in benzene at room temperature[297] No reaction was observed when nitrone 22 was treated with a solution of one to five equivalents of potassium superoxide and one equivalent of crown ether dissolved in benzene. Thus, the amounts of potassium superoxide and crown ether were increased to 5 equivalents. Still no product was observed. The result could be due to the fact that not enough superoxide radical anion was present because of poor solubility of potassium superoxide. Therefore, 20 equivalents of potassium superoxide and crown ether were directly treated with nitrone 22. These conditions gave a product in very low yield which was impossible to identify. Finally, nitrone 22 was directly treated using 6 equivalents of potassium superoxide. In this case, oxidation reaction was conveniently followed by TLC

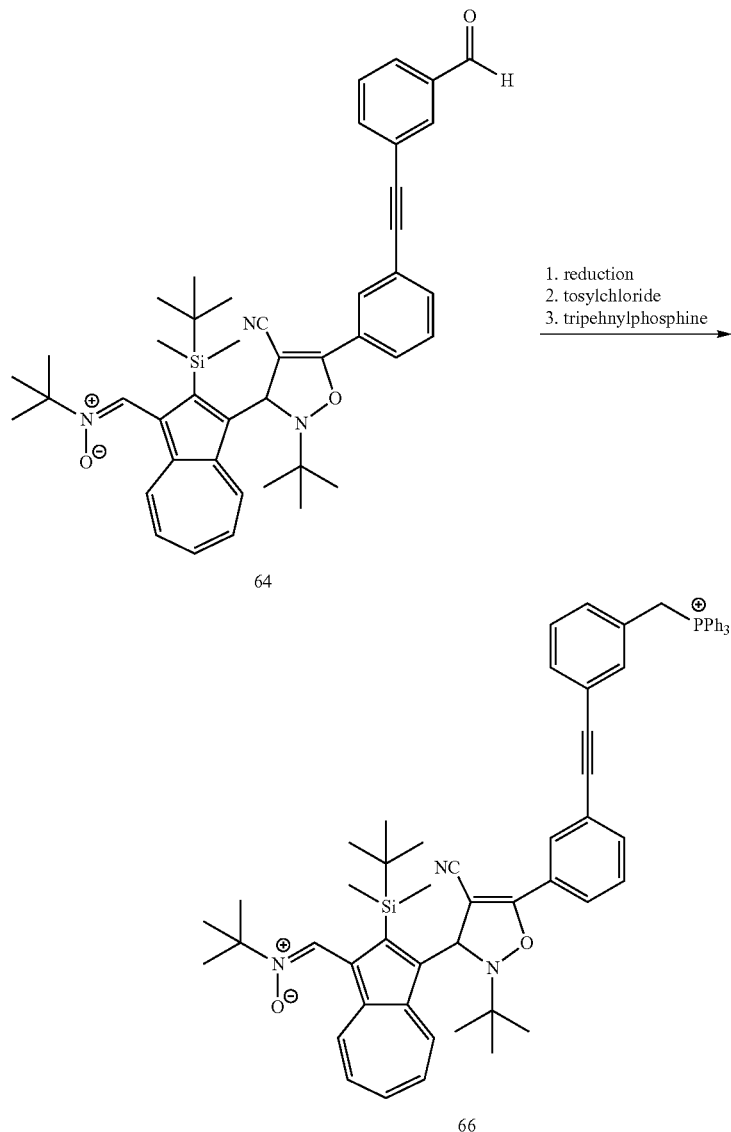

Figure 16. Synthetic Scheme of Compound 66

After the successful synthesis and characterization of several nitrones, experiments were conducted to test the properties and potential diagnostic application of these novel nitrones for detecting superoxide radical anion.

by monitoring the appearance of a less polar orange product which was analyzed by $^1$H NMR spectroscopy. The product was identified as aldehyde 67 by observing the aldehyde-proton signal and the up-field shifting of the ethyl signal of the azulene ring.

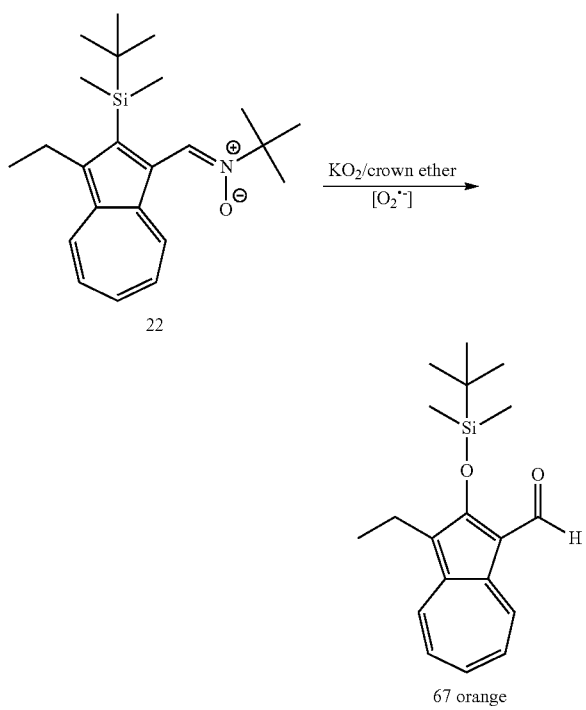

Figure 17. Formation of Aldehyde End Product 67

Formation of a ketone from analogous reaction between a ketonitrones and potassium superoxide has been previously reported.[297] Thus, α-diphenylene-N-phenylnitrone 68 was treated with superoxide and ketone 69 was found as a major product as shown in figure 18. Interestingly, aldehyde 67 was found to be very unstable because it decomposed while another orange product was started to appear as the reaction proceeded. Due to difficulty in purification, identification of the second orange product was not possible. The $^1$H NMR data showed no aldehyde-proton, and a low resolution mass peak at MH$^+$ of 663 was observed for this second orange product. The possible explanation could be that the aldehyde product is very liable to oxidation with superoxide anion and oxidized faster than nitrone 22 to form the second product.

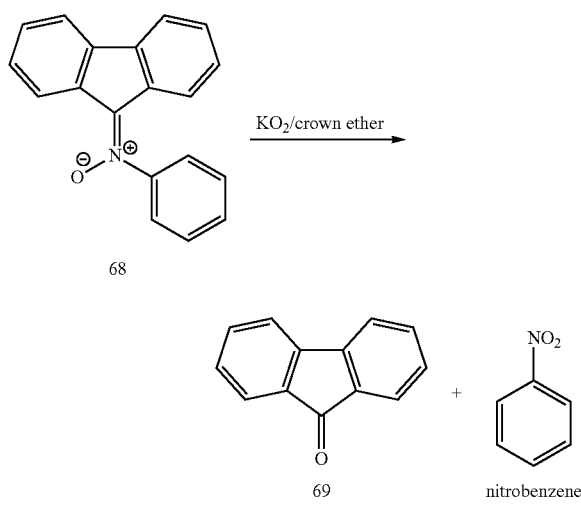

Formation of Ketone from α-Diphenylene-N-Phenylnitrone with KO$_2$

On the basis of the above result, expected aldehyde 67 was observed as an initial orange product which is supported by the proposed mechanism of oxidation of nitrone with superoxide (figure 19). Superoxide radical adds to nitrone 22 by radical addition to form intermediate nitroxide anion 70. Since silicon has high affinity towards oxygen, intramolecular nucleophilic attack of the anionic oxygen on silicon gives rise to an unstable pentavalent intermediate[298] 71 which subsequently undergoes rearrangement by migrating the azulenyl group to the adjacent oxygen as an alkoxide ion departs. Finally, collapse of the tetrahedral intermediate provides aldehyde 67. Such an oxidative desilylation process was initially described by Tamao and Kumada[299,300].

Information regarding the paramagnetic superoxide spin adduct, an intermediate presumed to be formed from the reaction of nitrone 22 with superoxide anion, remained unknown since ESR measurement was not available. However, similar to the superoxide spin adducts of the conventional acyclic nitrones, such a superoxide spin adduct would be expected to be highly unstable at room temperature. Grulke et al, in his ESR spin trapping study of DMPO with metmyoglobin and hydrogen peroxide at varying temperature, has found the nitrone peroxyl spin adduct unstable even at 0° C.[301]

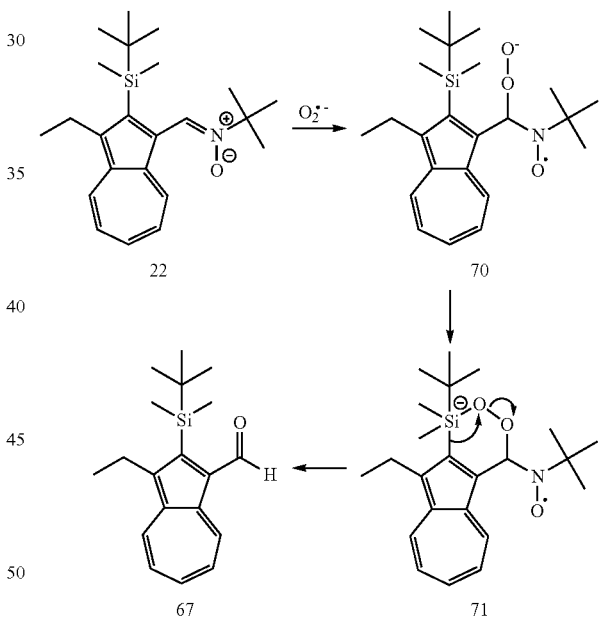

Proposed Mechanism of the Reaction of Nitrone 22 with Superoxide Radical

The detection of superoxide with azulenysilane mononitrone 23 was based on the previous method as described (vida supra). Six equivalents of potassium superoxide were used as before. As mentioned earlier, the previous reaction was monitored by observing an orange product on TLC. In this case, the reaction mixture turned completely from green to orange in 90 min. Based on the previous mechanism, it was expected to obtain the end product bis-aldehyde 72. However, $^1$H NMR spectral information of the orange end product indicated the loss of the silyl group, and presence of only the mono-aldehyde. The low resolution mass spectrum detected a MH$^+$ of 448. Unfortunately, it was not possible to purify enough for the NMR characterization. Hence, the structure identification of end product remained unsolved. It is believed that the superoxide spin adduct that formed was unstable and fragmented into another compound rather than the expected one. The loss of the silyl group could result after rearrangement via a nucleophilic attack on silicon by a second superoxide anion since an excess of superoxide anion was used and due to the high affinity of silicon towards oxygen.

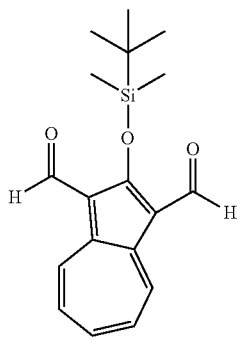

72

Expected Product from the Reaction of Nitrone 23 with Superoxide Radical

The unidentified end product from superoxide radical anion with nitrone 23 led us to synthesize an analogue, the isoxazoline azulenylsilanenitrone 24, and test it for its possible utility in superoxide detection. Using the same method as described earlier, superoxide was solubilized in benzene by employing in acrown ether. The only difference in this case was the use of three equivalents of potassium superoxide instead of six equivalents. The green reaction mixture was completely turned into orange solution. As in the previous case, aldehyde product 73 was expected to be formed. But surprisingly, NMR analysis showed the absence of an aldehydic proton, and a molecular mass of 469 was detected, which did not match with the aldehyde product. A high resolution mass spectrum of the major product was obtained and it was found to possess a molecular formula of $C_{29}H_{31}N_3O_3$. With HRMS and NMR spectral analyses, the orange product was identified as amide 74.

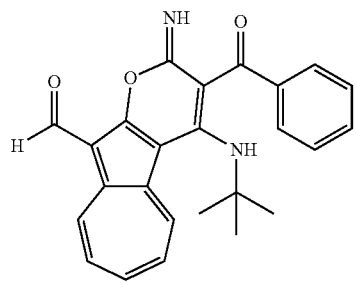

73

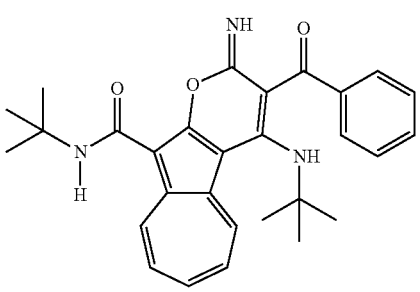

74 orange

The proposed mechanism for the formation of amide 74 from the spin trapping of superoxide radical anion by nitrone 24 is shown below. The addition of superoxide radical to the double bond of nitrone 24 leads to radical anion 75, which then suffers nucleophilic attack by the negatively charged oxygen on the silicon to give an intermediate with a six-membered ring (compound 76).[302] Then subsequent desilylation by migrating the azulenyl group to the adjacent oxygen atom transforms 76 into anion 77 in analogy to the work of Tamao and Kumada.[299] Rearrangement involving a nucleophilic attack of the anionic oxygen on silicon leaves the negative charge on oxygen at the 2-position, which in turn, undergoes a nucleophilic attack on the nitrile moiety thus resulting in the six-membered ring in compound 78. This step might also result in the rapid opening of the isoxazoline ring. Meanwhile, oxygen radical may be reduced by disproportionation (or reduced by ascorbic acid in a biological system) to form the corresponding hydroxylamine. Dehydration followed by desilylation affords amide 74. In

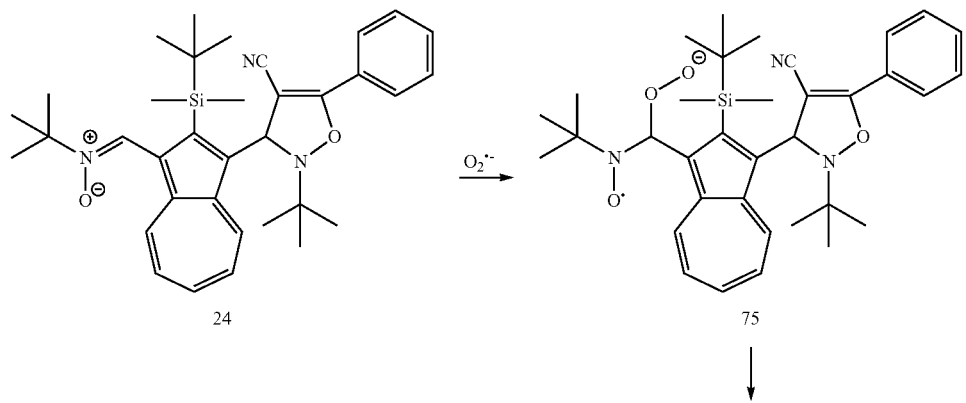

-continued

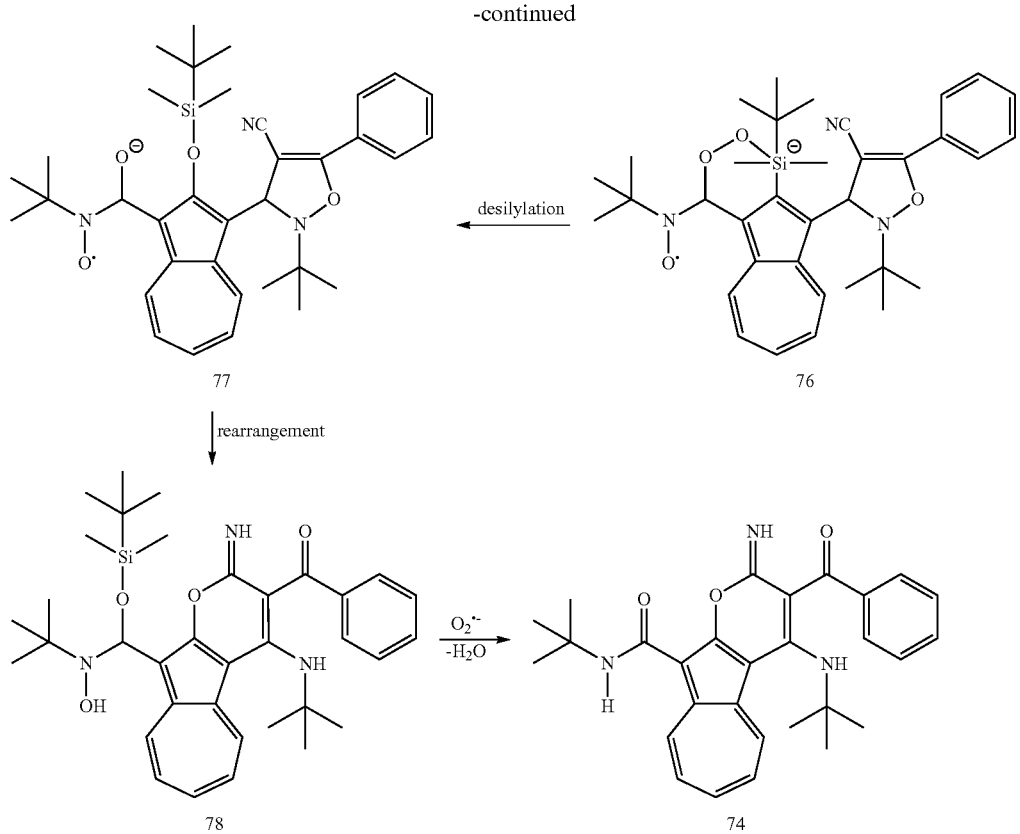

Hypothetical Mechanism of the Reaction of Nitrone 24 with Superoxide Anion addition to amide 74, a trace of orange compound 79 was also obtained which is identified by MS data 584 (MH+). The formation of 79 suggests a divergent mechanism that might have taken place in the reaction. Contrary to the first mechanism, the second mechanism pathway might have involved addition of one molecule of superoxide anion followed by dehydration to give 79.

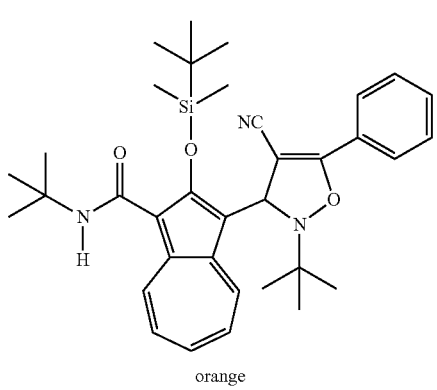

orange

The UV-vis (ultra visible) absorption spectrum and fluorescence of chromotropic amide 74 was measured in ethanol. As shown in figure 24, the UV-vis is indicated by the blue signal which consists of two strong absorbances in the range of 250-400 nm and one weak absorbance in the range of 400-500 nm. The fluorescence signal, indicated by red signal, was obtained by irradiating at the excitation wavelength 390 nm as shown in the spectrum. The wavelength dependence of the intensity of emitted light has been recorded at ~490 nm (emission). The quantum yield of amide was measured at 2.7%. These results suggest that compound 74 has fluorescence, and this probe may possibly be employed to detect superoxide anion in biological system by identifying its orange fluorescence. This, in addition to its chromotropic behavior, may bring an advantage over conventional cyclic nitrones which require ESR for superoxide detection.

One of the advantages of fluorescence detection is the possibility of real time monitoring of the oxidation process.

Guanylhydrazone nitrone 25 is a congener of nitrone 24. Incorporation of guanylhydrazone moiety may make it mitochondriotropic, and thereby render it useful to detect superoxide anion present in the mitochondria. As expected, nitrone 25 has also shown to trap superoxide efficiently in analogy to the other aforementioned nitrones. Using the same method as described for the other nitrones, nitrone 40 turned into brownish orange upon reaction with potassium superoxide. The brownish orange end product was isolated and identified as amide 80 using low resolution mass spectrum (MH+=654) which is analogous to the end product 74. In addition to amide 80, a trace of another orange product was also observed which is identified as amide 81 (MH+=768) analogous to amide 79.

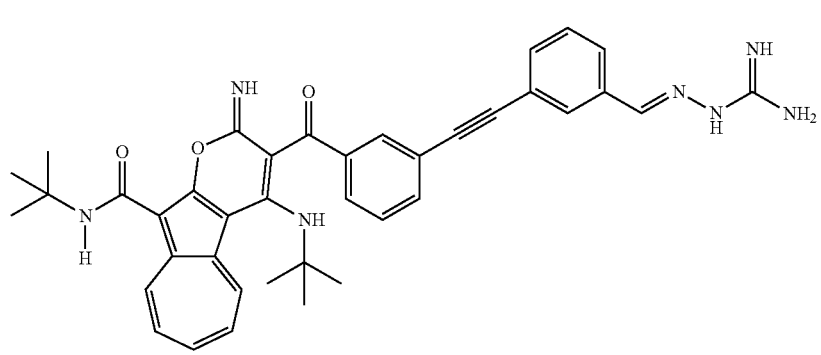

brownish orange 80

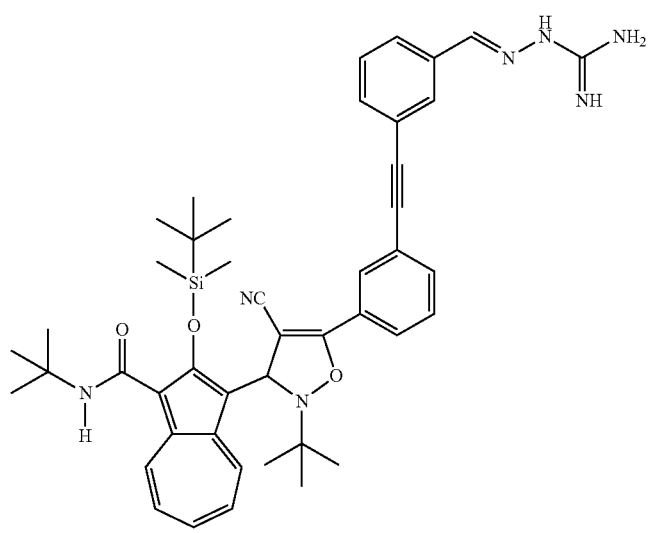

brownish orange (minor product) 81

Since nitrone 25 was poorly water soluble, its solubility in an aqueous systems was examined using solutol HS 15. Solutol HS 15 is a non-ionic solubilizer and emulsifying agent produced from 1 mole of 12-hydroxystearic acids and 15 moles of ethylene oxide. It provides excellent solubility to poorly soluble (lipophilic) molecules in water, and hence, it is used for formulation of drugs in the pharmaceuticals industry.

In this experiment, as expected, solutol HS 15 was found to increase the solubility of nitrone 25 in water. To prepare the concentration of 0.64 mg/ml of nitrone 25 in 3:7 solutol HS 15:1% saline solution, 1 ml of solutol HS 15 was heated until it turned into a clear liquid and cooled to room temperature. Meanwhile, 2.1 mg of nitrone 25 was crushed to a fine powder and dissolved in 1 ml of clear solutol HS 15. It was then diluted with 2.3 ml of 1% saline solution in water with frequent shaking and warming. It was then cool to room temperature to obtained green solution. The green solution was kept in a freezer, and found to be stable. The aqueous formulation of nitrone 25 with solutol HS 15 is believed to be amenable for mitochondrial superoxide detection and other biological studies.

Superoxide radical anion generation and its reactions in biological systems have received considerable attention because of the involvement of superoxide in physiological process as well as in the pathogenesis of various diseases. In biomedical research, it is important to characterize the specific free radical and its exact role in diseases which will allow investigators to design molecular or pharmacological approaches to prevent or ameliorate free radical-mediated maladies. But the direct detection of biologically generated superoxide radical anion, the identification of its sites of production, and its quantification are of the major challenges. By their nature, the inherent reactivity of most free radicals makes their direct in vivo detection impossible. Because of this difficulty, various techniques based on an indirect detection of superoxide have been developed with some degree of success.

Thus, techniques such as ESR (with cyclic nitrone spin traps), fluorescence, chemiluminescence and cytochrome c reduction have been used to study in vitro and in vivo detection of superoxide radicals in hopes of gaining insight with regard to cellular metabolism and pathogenesis of diverse cytotoxic events but each exhibits potential pitfalls as well as advantages. The Fluoresence-based technique using MitoSox red is considered as a simple and accurate method for estimation of biological superoxide, and hence it has been widely used for this purpose. However, it was found unreliable for intracellular detection because it does not detect superoxide specifically.

In a search for a more reliable, selective, and convenient method, this research developed structurally diverse novel azulenylsilane nitrones. Structurally, these novel nitrones are set up in such a way that they are specific for superoxide detection. For example, a nitrone moiety and an adjacent silyl group react readily with radicals and oxygen anion respectively. Such nitrones can trap superoxide efficiently because superoxide is both radical and an oxygen anion. Moreover, such nitrones allow chromotropic detection of superoxide by the virtue of their azulene core. Synthesis of dinitrone 55 has made it possible to design and synthesize other nitrone congeners with the incorporation of the electron-withdrawing cyano group, which yields a stable, characteristically colored, end product from its spin trapping reaction with superoxide. As expected, 2-terbutyldimethylsilyl-1 ethyl-3-azulenylnitrone (22), 2-tert-butyldimethylsilyl-3-azulenecarboxaldehyde 1-1nitrone (23), 2-tert-butyldimethylsilyl-3-tert-butylnitrone-1-(2-tert-butyl-4-cyano-5-phenyl)-azulenylisoxazoline (24) and mitochondria-targeted 2-tert-butyldimethylsilyl-1-[5-(3-aminoguanidinyl-phenylethynyl)-phenyl) 2-tert-butyl-4-cyano-5-phenyl isoxazole]-3-tert-butylazulenylnitrone (25) have been shown to trap superoxide radical anion efficiently yielding UV-VIS identifiable and even potentially fluorescence-detectable orange products. The in vitro results suggest that the chromotropic detection of superoxide using these nitrones can be a promising method in contrast to other available methods. Further work involves synthesis of mitochondria-targeted nitrones 65 and 66. Examination of superoxide reaction with nitrone 25 in biological systems encountered is underway. The in vivo detection of superoxide radical anion may provide additional information. Thus, nitrone 25 may be mitochondriotropic, and may have significant potential as a diagnostic tool for biological superoxide detection.

EXAMPLES

All of the moisture sensitive reactions have been carried out using syringe septum rubber cap technique under $N_2$ or Ar atmosphere or in a vial by flushing $N_2$ or Ar gas into it. The reactions at −78° C. have been performed employing compressed $CO_2$ and acetone bath. All of the reactions were monitored by TLC analysis (Whatman pre-coated silica gel $F_{254}$ plates, 250 μm layer thickness), and visualization was achieved by 254 nm UV light. The crude reaction mixtures have been purified by column chromatography using 60 A (200-300 mess) on silica gel. $^1H$ and $^{13}C$ NMR spectra were recorded on Bruker AVANCE-400 spectrometer in $CDCl_3$. Chemical shifts were measured in parts per million with residual solvent peak used as an internal standard. $^1H$ NMR spectra were run at 400 MHz and $^{13}C$ NMR spectra were recorder at 400 MHz with proton decoupled sequence. All low resolution mass spectra were obtained on Finnigan Navigator LC/MS instrument and DECA LC/MS by direct injection into the mass spectrometer and detecting molecular ion with ESI, and GC/MS. UV-vis spectrum was recorded using a Varian Cary 50 Bio spectrophotometer. Fluorescence (FL) spectrum was obtained using a Fluoromax-3 spectrofluorometer (JobinYvon/Habira). For determination of quantum yield (QY), 9,10-bis(phenylethynyl)anthracene (QY=1.0) in cyclohexane was used as a fluorescence standard.

Synthesis of
1-tert-Butyldimethylsilyl-1-ethyl-3-methylallene
(27)

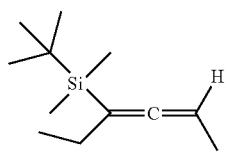

In a 150 ml three-necked round bottom flask 12.57 ml (17.6 mmol) of sec-butyllithium was cooled to −30° C. under argon and stirred with magnetic stirrer. To this was added 0.723 g (8.8 mmol) of 3-hexyne via a syringe and stirred for 3 hours. The reaction mixture was then cooled to −78° C. and, 2.6 gm (17.6 mmol) of TBDMSCl in THF was added with a syringe and left the mixture overnight. Subsequently, the reaction mixture was poured on ice and aqueous layer was extracted with ether (3×20 ml). The combined ether layers were then washed with 15 ml of saturated sodium chloride, dried over $MgSO_4$ and, concentrated in rotavap. The resulting residue was distilled (b.p. 90-95° C.) and column chromatographed using pentane to yield 172 mg of solution colorless oil containing allenylsilane (27). The crude solution was used to prepare compound 28 without further purification.

Synthesis of
2-tert-Butyldimethylsilyl-1-ethyl-3-methylazulene
(28)

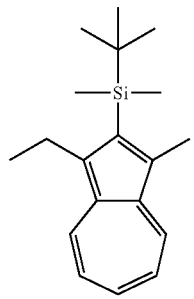 [SMILES: CCc1c2cccccc-2c(C)c1[Si](C)(C)C(C)(C)C]

In a 250 ml three-necked round bottom flask, fitted with an argon inlet adapter and a magnetic stirring bar, allenylsilane (232 mg, 1.18 mmol) was treated with 10 ml of acetonitrile, and 0.415 g of poly-4-vinylpyridine (3.94 mmol) and stirred for a minute. Trophylium tetrafluoroborate (0.470 g, 2.63 mmol) was then added to the resulting suspension in one portion. The reaction mixture turned blue in one minute, which was then stirred in the dark for 24 h at the room temperature. The dark blue reaction mixture was filtered, and the solid residue was washed with hexane 100 ml of hexane followed by 10 ml of acetonitrile until washing were clear. The filtrate was transferred into a separatory funnel and the top hexane layer was separated from the bottom acetonitrile layer. The separated acetonitrile layer was further extracted from hexane (3×20 ml) until the extract was clear. The combined hexane layers were then washed with 15 ml of saturated sodium chloride, dried over anhydrous magnesium sulfate, filtered, and evaporated in a rotavap. The blue green solid was then purified by chromatography on silica gel (eluent hexane) to give 0.1678 g of azulenylsilane as blue-green crystals. $^1H$ NMR δ 8.11 (d, 1H, J=9.4), 8.09 (d, 1H, J=9.5), 7.39 (t, 1H, J=9.7), 6.87 (t, 2H, J=9.8), 3.17 (q, 2H, J=7.5), 2.70 (s, 3H), 1.26 (t, 3H, J=7.5), 0.91 (s, 9H), 0.5 (s, 6H); $^{13}C$ NMR δ 147.7, 140.9, 139.3, 138.1, 137.6, 134.2, 134.0, 133.4, 121.9, 121.8, 28.4, 23.0, 20.5, 19.0, 15.8, 0.00. LRMS (LC/MS-ESI, MeOH) m/e 285 (MH⁺)

Synthesis of 2-tert-Butyldimethylsilyl-1ethyl-3-azulenecarboxaldehyde (30)

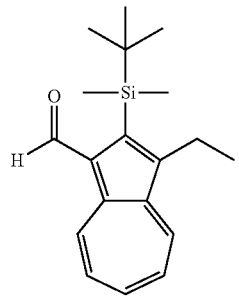

In a 250 ml round bottom flask, azulenyl silane (290 mg, 1.021 mmol) was dissolved in 2 ml of acetone and was added 2,3-dichloro-5,6-dicyano-1-benzoquinone (463.5 mg, 2.042 mmol) and stirred at room temperature for 30 minutes in the dark. The reaction mixture immediately turned from blue to violet color. When all the reactant was gone, 15 ml of saturated sodium thiosulfate was added and stirred for 5 min to remove unreacted DDQ. To this reaction mixture, 15 ml of sodium carbonate was added and stirred for 5 minutes to remove acidic $DDQH_2$. The resulting reaction mixture was then poured into 250 ml of chloroform and transferred into separatory funnel. The separation of two layers was very hard to visualize. The bottom chloroform layer was separated from the top aqueous layer then the aqueous layer was extracted with chloroform (2×25 ml). The combined chloroform layers were washed with 15 ml of saturated sodium chloride, dried over anhydrous magnesium sulfate, and concentrated in rotavap. The residue violet solid was then purified by column chromatography with eluent 2:8 ethyl acetate:hexane to provide 228 mg of azulenylsilane aldehyde (30) in 75% yield. $^1$H NMR δ 10.54 (s, 1H), 9.85 (d, 1H, J=9.85), 8.44 (d, 1H, J=9.80), 7.79 (t, 1H, J=9.77), 7.55 (t, 1H, J=9.86), 7.47 (t, 1H, J=9.76), 3.18 (q, 2H J=7.54), 1.30 (t, 3H, J=7.53), 0.97 (s, 9H) 0.56 (s, 6H); $^{13}$C NMR δ 190.16, 153.14, 142.63, 142.42, 142.11, 140.4, 138.69, 135.74, 130.85, 130.15, 127.61, 127.49, 21.64, 18.72, 17.23, 0.00; LRMS (LC/MS-ESI, MeOH) m/e 299 (MH$^+$). Elution with 3:7 ethylacetate:hexane gave 32 mg of azulenysilane alcohol-aldehyde (31) in 10% yield. $^1$H NMR δ 10.52 (s, 1H), 9.92 (dd, 1H), 9.36 (dd, 1H), 7.86 (tm, 1H), 7.62 (t, 1H), 7.54 (t, 1H), 5.72 (q, 1H), 1.95 (s, 1H), 1.77 (d, 3H, J=6.64) 1.1 (s, 9H), 0.55 (s, 3H)). 50 (s, 3H); $^{13}$C NMR δ 189.82, 152.25, 142.83, 141.82, 141.77, 140.76, 139.02, 138.84, 130.36, 130.18, 127.97, 67.81, 27.01, 24.29, 18.16, 0.25, 0.10; LRMS (LC/MS-ESI, MeOH) m/e 315 (MH$^+$)

Synthesis of 2-terbutyldimethylsilyl-1ethyl-3-azulenylnitrone (22)

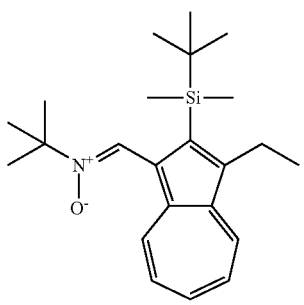 [SMILES: CCc1c2cccccc-2c(/C=[N+](\[O-])C(C)(C)C)c1[Si](C)(C)C(C)(C)C]

According to Becker et. al protocol, 101 mg (0.34 mmol) of compound 30 was treated with N-tert-butyl hydroxylamine (212.84 mg, 1.69 mmol) and anhydrous magnesium sulfate (204 mg, 1.69 mmol) in 2 ml of anhydrous pyridine under argon. The reaction mixture was stirred at 40° C. for 21 days. The TLC showed the product as well as some starting material. The reaction mixture was then poured into 20 ml of water and extracted with ether (3×25 ml). The ether layer was washed with 10 ml of saturated sodium chloride, dried over magnesium sulfate and concentrated in a rotavap. The residue product was then purified by column chromatography using 7:3 ethylacetate:hexane to provide 58.6 m of nitrone (22) in 47% yield. $^1$H NMR δ 8.25 (d, 2H J=9.75), 8.11 (s, 1H), 7.60 (t, 1H), 7.22 (t, 1H), 7.18 (t, 1H), 3.16 (q, 2H), 1.7 (s, 9H), 1.26 (t, 3H), 0.94 (s, 9H), 0.49 (s, 6H); $^{13}$C NMR δ 146.71, 141.68, 140.04, 138.54, 137.88, 135.03, 133.63, 129.53, 124.12, 123.93, 123.31, 69.81, 28.46, 26.87, 21.65, 18.77, 17.43, −1.56; LRMS (LC/MS-ESI, MeOH) m/e 369 (MH$^+$)

Synthesis of Acetaldehyde tert-butylimine (35)

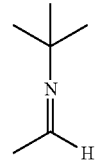

Based on the literature, in a three-necked round bottom flask, fitted with a dropping funnel and a magnetic stir bar, was placed 16.5 g of tert-butylamine (226 mmol) under argon and kept on ice bath. To this 10 g of acetaldehyde (226 mmol) was introduced dropwise at 0° C. The mixture was stirred at this temperature for 3 hr, then 600 mg of solid KOH (10.7 mmol) was added and kept in a refrigerator at 4° C. for 12 hr to allow the separation of two layers to complete. The bottom aqueous layer was removed using a separatory funnel and the top organic layer was transferred into a flask which was then distilled (bp 66-70° C.) to provide 19.9 g of aldiimine (35) in 88% yield as a colorless oil. The product was found identical to an authentic sample by using $^1$H NMR. $^1$H NMR δ 7.61 (q, 1H J=4.8 Hz), 1.90 (dd, 3H, J=4.8 Hz), 1.10 (s, 9H)

Synthesis of 2-tert-butyldimethylsilyl-propylimine (36)

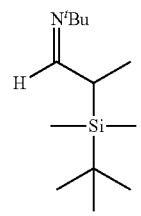

Applying the literature procedure[277], in a three-necked round bottom flask containing 13.4 ml of 1.5 M LDA in THF (20.20 mmol) was added 2 g of acetaldehyde aldimine 35 in THF (20.20 mmol) at 0° C. and the reaction mixture was stirred at this temperature for 30 min under argon. Initially the reaction mixture turned into yellow, and later it turned into red. To this mixture, 3.05 g of TBDMSCl in THF (20.20 mmol) was added followed by the addition 0.373 g of Bu$_4$NI (1.01 mmol) at 0° C. The reaction mixture was then stirred at room temperature for 3 hr. The resulting yellow color solution was then treated with 8.08 ml of BuLi in hexane (20.20 mmol) at 0° C. and stirred for 1 hr at this temperature. Subsequently, 2.86 g of iodomethane (20.20 mmol) was added at this temperature and then allow the mixture to warm up to room temperature over 12 hr. The reaction mixture was then diluted with 40 ml of diethyl ether and poured onto ice-water. The organic layer was separated and the aqueous layer was extracted with diethyl ether (2×40 ml). The combined organic layers were washed with saturated NaCl, dried over MgSO₄ and concentrated in a vacuo to provide 6.5 g of crude 36 which has been used to prepare compound 37 without further purification.

Synthesis of 2-tert-butyldimethylsilyl-propylaldehyde (37)

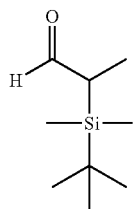

The crude product 36 was hydrolysed by dissolving in 2 ml of petroleum ether/EtOAc (7:1) and filtered through a column of silica gel using petroleum ether/EtOAc (7:1) as eluent to furnish 2.82 g of silylaldehyde (81%) as an orange oil. The product is identical to the authentic sample. $^1$H NMR δ 9.72 (d, 1H, J=1.6), 2.49 (dq, 1H J=6.7, 1.6), 1.16 (d, 3H, J=6.7), 0.92 (s, 9H), 0.03 (s, 3H), 0.01 (s, 3H); $^{13}$C NMR δ 203.22, 40.95, 26.69, 17.50, 8.95, −6.71, −6.88; LRMS (GC-MS) m/e 172 (M⁺)

Synthesis of 1-dibromo-3-tert-butyldimethylsilyl-1-butene (38)

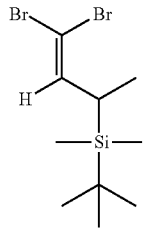

2.7 g of tetrabromomethane (8.14 mmol) was stirred in CH₂Cl₂ (1M) and kept at 0° C. To this solution was added 4.35 g triphenylphosphine (16.6 mmol) in CH₂Cl₂ (2M) and stirred at this temperature for 30 min. Then the solution of 500 mg of aldehyde 37 (2.90 mmol) in CH₂Cl₂ (0.5M) was added and stirred at 0° C. for 2 hr. The reaction mixture was then treated with 42 ml of ether and the resulting white precipitates were filtered off. The filtrate was then washed with 9 ml of H₂O, 9 ml of saturated NaHCO₃, 9 ml of saturated NH₄Cl, 9 ml of saturated NaCl, and dried over MgSO₄. The solvent was then evaporated in vacuo and the residue was eluted with 30:1 petroleum ether:ethylacetate in a column chromatography to furnish 733 mg of dibromo compound 38 in 77% yield as a colorless oil. $^1$H NMR δ 6.25 (d, 1H, J=11.5), 2.08 (dq, 1H, J=11.5, 7.2), 1.10 (d, 3H, J=7.2), 0.94 (s, 9H), 0.00 (s, 3H), −0.01 (s, 3H); $^{13}$C NMR δ 142.82, 84.41, 27.04, 26.52, 17.37, 14.79, −7.28, −7.34; LRMS (GC-MS) m/e 328 (M⁺)

Synthesis of 4-tert-butyldimethylsilyl-1-pentyne (39)

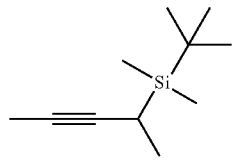

340 mg of 38 (1.07 mmol) was dissolved in THF (0.25M) and kept in dry ice/acetone water bath. To this solution 1 ml of BuLi (2.28 mmol) was added at −78° C. under argon and stirred for 30 min. The reaction mixture was then quenched with 0.08 ml (182 mg) of iodomethane (1.28 mmol) and heated at 40° C. for 2 hr. After 2 hr stirring, the reaction mixture was brought to room temperature and stirred for another 18 hr. To this reaction mixture 10 ml of 1:1 ether/water was added and then aqueous layer was separated and washed with ether (3×20 ml). The organic layers were combined and washed with 20 ml of saturated NaCl, drie over MgSO₄ and concentrated in rota vap. The residue was then purified by column chromatography using petroleum ether to furnish 160 mg of 39 as pale yellow oil (82%). $^1$H NMR δ 1.78 (s, 3H), 1.75-1.79 (m, 1H), 1.17 (d, 3H, J=7.2), 0.95 (s, 9H), −0.02 (s, 3H), 0.04 (s, 3H); $^{13}$C NMR δ 83.20, 74.89, 27.12, 17.40, 16.29, 10.29, 3.61, −7.42, −7.82; LSMS (GC-MS) m/e 182 (M⁺)

Synthesis of 2-tert-butyldimethylsilyl-1,3-dimethylazulene (40)

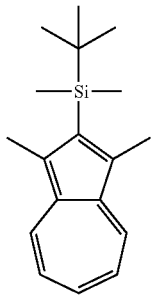

In a three necked round bottomed flask, containing magnetic stirring bar, 2.13 mg of 38 (11.69 mmol) was treated with 85 ml of acetonitrile and 4.06 g of poly(4-vinylpyridine (38.57 mmol) and stirred under argon at room temperature. To the resulting suspension was added 4.58 g of trophylium tetrafluoroborate (25.72 mmol) in one portion. The reaction mixture was turned into blue in 60 seconds and stirred at room temperature in the dark for 24 h. The dark blue reaction mixture was then filtered, and the solid residue was washed with 300 ml of hexane and 20 ml of acetonitrile until the washing became clear. The filtrate was transferred into a separatory funnel, shaken vigorously, and the top blue hexane layer was separated from the bottom brown acetonitrile layer. The acetonitrile layer was extracted with hexane (4×40 ml). The combined hexane layers were washed with 15 ml of saturated sodium chloride, dried over anhydrous MgSO4, filtered, and evaporated the solvent to obtain blue-green solid. The blue green residue was then purified by column chromatography using hexane to furnish 687 mg of azulene 40 as blue-green crystals in 22% yield. $^1$H NMR δ 8.18 (d, 2H, J=9.8), 7.46 (t, 1H, J=9.8), 6.96 (t, 2H, J=9.8), 2.81 (s, 6H), 1.05 (s, 9H), 0.6 (s, 6H); $^{13}$C NMR δ 147.12, 137.87, 136.89, 132.68, 132.28, 120.38, 26.99, 19.33, 14.38, −1.46; LRMS (LC/MS-ESI, MeOH) m/e 271 (MH$^+$)

Synthesis of 2-tert-butyldimethylsilyl-1,3-azulenedicarboxaldehyde (32)

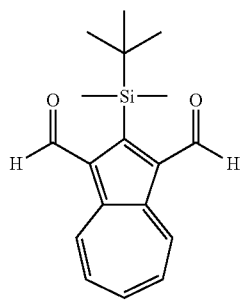

90 mg of 40 (0.33 mmol) was dissolved in 5 ml of acetone at room temperature. To this solution was added 359 mg of DDQ (2,3-dichloro-5,6-dicyano-1,4-benzoquinone) (1.58 mmol) in one portion. The reaction mixture immediately turned color from blue to red as it was stirred in the dark for 1 hour. When all reactant was gone the reaction mixture was stirred with 15 ml of saturated sodium thiosulfate solution to remove unreacted DDQ for 2 min and then 15 ml of saturated sodium bicarbonate was added, and then it was stirred for 2 min to remove acidic DDQH$_2$. The reaction mixture was then extracted with chloroform (5×40 ml). The combined bottom red organic phases were subsequently washed with 15 ml of saturated NaCl solution, dried over anhydrous MgSO4, filtered and evaporated. The red residue was then purified by column chromatography using 7:3 hexane:ethylacetate to provide 88.4 mg of bis-aldehyde 32 in 89% yield as red crystals. $^1$H NMR δ 10.59 (s, 2H), 10.12 (dd, 2H, J=10), 8.11 (tt, 1H, J=10), 7.94 (t, 1H, J=10), 1.05 (s, 9H), 0.61 (s, 6H); $^{13}$C NMR δ 190.28, 162.4, 144.9, 142.75, 140.94, 134.14, 132.73, 27.06, 17.99, 0.98; LRMS (LC/MS-ESI, MeOH) m/e 299 (MH$^+$)

Synthesis of 2-tert-butyldimethylsilyl-3-formyl-azulene-1-nitrone (23)

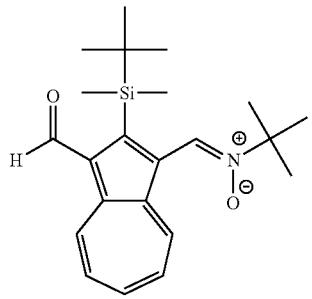 [SMILES: CC(C)(C)/[N+]([O-])=C/c1c2cccccc-2c(C=O)c1[Si](C)(C)C(C)(C)C]

To the mixture of 50 mg of bis-aldehyde 32 (0.167 mmol), 42.2 mg of tert-butylhydroxylamine hydrochloride (0.335 mmol) and 40.4 mg of anhydrous magnesium sulfate (0.335 mmol) was added 1.4 ml of pyridine to dissolve. The reaction mixture was then stirred and heated to 40° C. for 1 week under argon. The color of the reaction solution changed from red into green. The crude product was then poured into 5 ml of water and extracted with 5 ml of ether. Then aqueous layer was separated from ether layer. The aqueous layer was further extracted with ether (2×5 ml). The combined ether layer was washed with saturated sodium chloride, dried over magnesium sulfate, filtered and, evaporated in vacuo. The residue was then purified by silica gel column chromatography using 5:5 hexane:ethylacetate to produce 20.3 mg of mononitrone 23 in 33% yield as green crystals. $^1$H NMR δ 10.51 (s, 1H), 9.95 (d, 1H, J=9.9), 8.27 (d, 1H, J=9.9), 8.10 (s, 1H), 7.94 (t, 1H, J=9.9), 7.74 (t, 1H, J=9.9), 7.69 (t, 1H, J=9.9), 1.71 (s, 9H), 0.99 (s, 9H), 0.53 (s, 6H); $^{13}$C NMR δ 189.25, 156.37, 143.34, 140.97, 140.49, 139.84, 139.52, 132.35, 131.69, 129.2, 128.19, 127.83, 70.46, 28.35, 26.81, 18.35, −0.65; LRMS (LC/MS-ESI, MeOH) m/e 370 (MH$^+$)

Synthesis of 2-tert-butyldimethylsilyl-1,3-azulenyldinitrone (55)

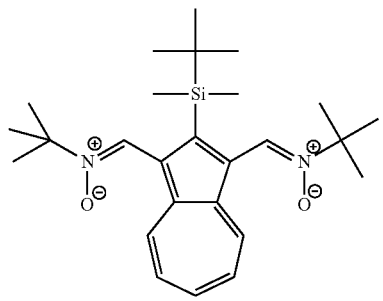 [SMILES: CC(C)(C)/[N+]([O-])=C/c1c2cccccc-2c(/C=[N+](\[O-])C(C)(C)C)c1[Si](C)(C)C(C)(C)C]

A solution of 77 mg of dialdehyde 32 (0.26 mmol), 162 mg of tert-butylhydroxylamine hydrochloride (1.3 mmol), 155 mg of anhydrous magnesium sulfate, and 1 ml of pyridine was stirred at 45° C. for 2 weeks under argon. The resulting mixture was then pour into 5 ml of water and extracted with 5 ml of ether. The aqueous layer was extracted with (2×5 ml) ether. The combined ether layers were washed with saturated sodium chloride, dried over MgSO4, filtered and concentrated in vacuo. The resulting residue was then purified by column chromatography using 100:1 chloroform:methanol as eluenting solvent to furnish 35.4 mg of 55 in 31% yield as green crystals. 55 was also prepared in 35% yield by heating 66 mg of mononitrone 23 (0.18 mmol), 67.4 mg of tert-butylhydroxylamine hydrochloride (0.54 mmol), 64.6 mg of anhydrous MgSO$_4$ (0.54 mmol) and 1 ml of pyridine at 45° C. for 10 days. $^1$H NMR δ 8.35 (d, 2H, J=9.5), 8.07 (s, 2H), 7.76 (t, 1H, J=9.7), 7.48 (t, 2H, J=9.9), 1.70 (s, 18H), 0.95 (s, 9H), 0.48 (s, 6H); $^{13}$C NMR δ 149.62, 139.58, 138.71, 138.04 128.74, 126.86, 126.11, 70.08, 28.44, 26.53, 18.70, −2.05; LRMS (LC/MS-ESI, MeOH) m/e 441 (MH$^+$)

Synthesis of 2-[2-(tert-butyldimethyl-silanyl)-3-formyl-azulen-1-yl]-5-cyclohexylamino-furan-3,4-dicarboxylic acid dimethyl ester (50)

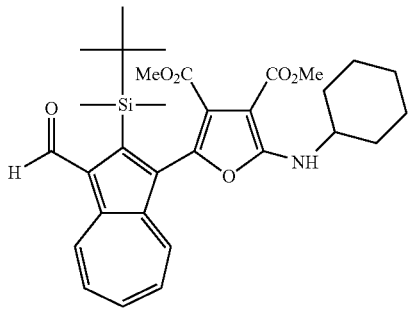 [SMILES: COC(=O)c1c(NC2CCCCC2)oc(-c2c3cccccc-3c(C=O)c2[Si](C)(C)C(C)(C)C)c1C(=O)OC]

According to the literature procedure, a mixture of 250 mg of bis-dialdehyde 32 (0.84 mmol) and 92 mg of DMAD (dimethyl acetylenedicarboxylate) (0.84 mmol) was dissolved in 8.5 ml of anhydrous benzene and heated at 80° C. under argon. To this solution was added 119 mg of cyclohexylisocyanide (0.84 mmol) by syringe, and the heating was continued at 80° C. for further 5 days. The color of the reaction changed from red into brown. The solvent was then evaporated in vacuo, and the crude residue was purified on column chromatography using 8:2 hexane:ethylacetate to obtain first starting material, and then polarity was increased to 7:3 hexane:ethylacetate to furnish 117 mg of 50 as wine red solid in 25% yield. $^1$H NMR δ 10.59 (s, 1H), 9.99 (dd, 1H, J=9.9, 0.8), 8.40 (dd, 1H, J=9.9, 0.8), 7.90 (t, 1H, J=9.8), 7.71 (t, 1H, J=9.8), 7.40 (t, 1H, J=9.7), 6.72 (d, 1H, J=8.9), 3.82 (s, 3H), 3.52-3.365 (m, 1H), 3.49 (s, 3H), 1.20-2.05 (m, 10H), 0.95 (s, 9H), 0.34 (s, 3H), 0.23 (s, 3H); $^{13}$C NMR δ 189.84, 165.34, 164.39, 162.04, 157.31, 146.20, 141.70, 141.15, 139.83, 139.73, 138.19, 131.24, 130.20, 129.45, 125.96, 118.56, 86.09, 51.74, 51.35, 51.03, 34.01, 33.89, 27.34, 25.27, 24.69, 24.60, 17.95, −1.86, −3.42; LRMS (LC/MS-ESI, MeOH) m/e 550 (MH$^+$)

Synthesis of 2-[2-(tert-butyldimethyl-silanyl)-3-tert-butylnitrone-azulen-1-yl]-5-cyclohexylamino-furan-3,4-dicarboxylic acid dimethyl ester (49)

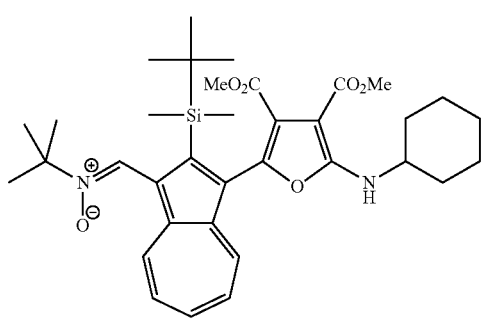 [SMILES: COC(=O)c1c(NC2CCCCC2)oc(-c2c3cccccc-3c(/C=[N+](\[O-])C(C)(C)C)c2[Si](C)(C)C(C)(C)C)c1C(=O)OC]

A solution of 13.5 mg of aminofuran adduct 50 (0.025 mmol), 9.3 mg of tert-butylhydroxylamine hydrochloride (0.074 mmol), 8.9 mg of magnesium sulfate (0.074 mmol), and 0.3 ml of pyridine was purged with argon and stirred at 50° C. for 7 days. The reaction mixture was then poured into 5 ml of water and extracted with ether (3×5 ml). The combined ether layers were then washed with 10 ml of saturated sodium chloride, dried over anhydrous magnesium sulfate, filtered, and evaporated in vacuo. The resulting green residue was then purified by column chromatography using 5:5 ethylacetate/hexane to produce 3 mg of nitrone 49 in 20% yield. $^1$H NMR δ 8.48 (d, 1H, d=9.9), 8.25 (d, 1H, d=9.2), 8.2 (s, 1H), 7.74 (t, 1H, d=9.8), 7.44 (t, 1H, d=9.9), 7.37 (t, 1H, d=9.8), 6.68 (d, 1H, d=8.8), 3.81 (s, 3H), 3.50-3.57 (m, 1H), 3.49 (s, 3H), 1.85-2.00 (m, 2H), 1.7 (s, 9H), 1.10-1.40 (m, 8H), 0.28 (s, 3H), 0.2 (s, 3H); $^{13}$C NMR δ 165.47, 164.61, 161.99, 151.19, 144.02, 140.27, 139.60, 139.55, 136.68, 136.10, 129.02, 126.50, 125.40, 125.33, 125.22, 118.07, 86.11, 70.15, 51.11, 51.37, 51.00, 33.97, 28.47, 27.17, 25.36, 24.79, 24.63, 18.48, 0.00, −3.20, −4.15; LRMS (LC/MS-ESI, MeOH) m/e 621 (MH$^+$)

Synthesis of p-formylphenyl isocyanate (53)

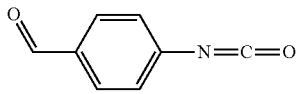 [SMILES: O=C=Nc1ccc(C=O)cc1]

According to the modified method of Yamada, 1 gm of 4-carboxybenxzaldehyde (6.67 mmol) was suspended in 16 ml of anhydrous methylene chloride and added 0.9 ml (0.66 g) of triethylamine (6.67 mmol). After all the solid had dissolved, 1.44 ml of diphenylphosphoryl azide (6.67 mmol) was added dropwise through a syringe. The content was then refluxed for 6 hr. The reaction mixture changed the color from colorless to pale yellow. The solvent was then evaporated in vacuo. The resulting yellow solid was then dissolved in 40 ml of ether and washed with aqueous sodium bicarbonate at PH 9 (2×25 ml). The ether layer was dried over anhydrous magnesium sulfate, filtered, and evaporated ether to provide 1 gm of 53 as a pale yellow solid in 100% yield. $^1$H NMR δ 10.12 (s, 1H), 8.20 (d, 2H, J=8.3), 7.80 (d, 2H, J=8.3); $^{13}$C NMR δ 191.33, 171.73, 140.03, 135.34, 130.05, 129.70; LRMS (GC-MS, CH$_2$Cl$_2$) m/e 147 (M$^+$), 146, 118, 90, 63, 51; IR (NaCl) 2136 cm$^{-1}$ for isocyanate group.

Synthesis of 2-tert-butyl-3-[2-(tert-butyldimethyl-silanyl)-3-nitrone-azulen-1-yl]-5-phenyl-2,3-dihydro-isoxazole-4-carbonitrile (24)

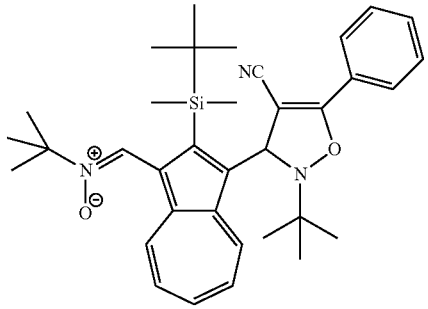 [SMILES: CC(C)(C)N1OC(c2ccccc2)=C(C#N)C1c1c2cccccc-2c(/C=[N+](\[O-])C(C)(C)C)c1[Si](C)(C)C(C)(C)C]

According to the literature procedure, the mixture of 26 mg of dinitrone 55 (0.06 mmol) and 7.5 mg of phenylpropiolonitrile (0.06 mmol) was dissolved in 1 ml of anhydrous benzene and heated at 50° C. for 6 days. The solvent was then dried in vacuo to provide green solid. The resulting green residue was then purified by column chromatography on silica gel using 7:3 hexane:ethylacetate which afforded 25 mg of 24 as green crystals in 75% yield and 19% of starting materials. $^1$H NMR δ 9.22 (d, 1H, J=9.5), 8.21 (d, 1H, J=9.5), 8.19 (s, 1H), 7.92 (dd, 2H, J=8, 1.3), 7.65 (t, 1H, J=9.7), 7.47 (m, 3H), 7.32 (t, 1H, J=9.7), 7.25 (t, 1H, J=9.7), 6.33 (s, 1H), 1.70 (s, 9H), 1.25 (s, 9H), 1.00 (s, 9H), 0.73 (s, 3H), 0.40 (s, 3H); $^{13}$C NMR δ 161.62, 146.75, 140.63, 139.34, 138.55, 137.21, 136.95, 135.44, 131.68, 129.30, 128.86, 127.12, 125.87, 125.66, 124.90, 124.63, 116.20, 85.80, 70.06, 65.28, 61.87, 28.38, 28.03, 25.39, 19.18, 0.27, −1.26; LRMS (LC/MS-ESI, MeOH) m/e 568 (MH$^+$)

Synthesis of (3-ethynyl-phenyl)-1-propyne nitrile (63)

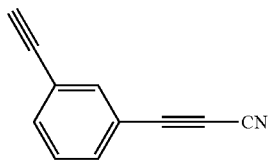

According to a literature procedure, three-necked round bottom flask, fitted with argon inlet and containing a magnetic stirring bar, is charged with 11.3 ml of DMSO, (dimethyl sulfoxide), 3.75 ml of acetonitrile and 0.2 ml of water, and stirred the solution rapidly. To this rapidly stirring solution, 1.35 g of cuprous cyanide (15 mmol) was added very slowly to avoid formation of lumps. 113 mg of sodium iodide (0.752 mmol) was then added to the reaction mixture, and was stirred for 1 min. Then 1 ml (0.940 g) of 1,3-diethynylbenzene (7.53 mmol) was added slowly via syringe. Subsequently, 2.9 ml (2.45 g) of chlorotrimethylsilane (22.56 mmol) was added dropwise via syringe over 20 min and stirred the reaction mixture at 50° C. for 24 hr. The reaction mixture was then cooled to room temperature then 5 ml of water was added, and it is extracted with ether (5×10 ml). The combined ether layers were then washed with 25 ml of saturated sodium bicarbonate, 25 ml of saturated sodium chloride, dried over anhydrous magnesium sulfate, filtered and evaporated the solvent by rotatory evaporation to give crude yellow oil. The crude residue was then purified by silica gel column chromatography using pentane as eluenting solvent to afford 147 mg of (3-ethynyl-phenyl)-1-propyne nitrile as white crystals in 13% yield. $^1$H NMR δ 7.72 (sm, 1H), 7.63 (dt, 1H, J=0.02), 7.58 (dt, 1H, J=0.02), 7.39 (t, 1H, J=0.02), 3.16 (s, 1H); $^{13}$C NMR δ 136.74, 135.26, 133.39, 129.03, 123.44, 118.06, 105.19, 81.67, 81.49, 79.26, 63.59; LRMS (GC/MS, CH$_2$Cl$_2$) m/e 151 (M$^+$)

Synthesis of [3-(3-Formyl-phenylethynyl)-phenyl]-propyne nitrile (61)

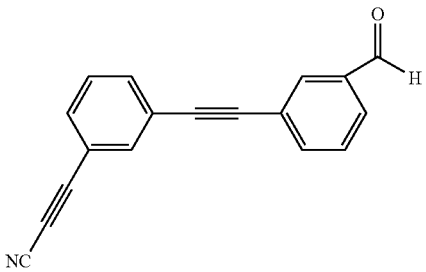 [SMILES: N#CC#Cc1cccc(C#Cc2cccc(C=O)c2)c1]

87 mg of (3-ethynyl-phenyl)-1-propyne nitrile 63 (0.576 mmol), 120.3 mg of 3-iodobenzaldehyde, and 0.8 ml triethylamine (58.5 mg, 0.576 mmol) were dissolved in 1.5 ml of anhydrous THF, and the solution was deoxygenated by purging argon in it. To this solution was added 22 mg of tetrakistriphenylphosphine palladium (0.019 mmol) then the reaction was allowed to stir for 20 min at room temperature. To this stirring mixture was added 0.9 mg of cuprous iodide (4.5×10$^{−3}$) then stirred at room temperature for 2 hr, followed by heating further at 50° C. for 2 hr. The solvent was then evaporated in rotatory evaporation to give brown solid. The residue was then purified by silica gel column chromatography using 1:9 dichloromethane:hexane to collect starting material. The polarity was increased to 2:8 dichloromethane:hexane to afford 80 mg of 61 as a golden solid in 55% yield. $^1$H NMR δ 10.2 (s, 1H), 8.04 (sm, 1H), 7.89 (dm, 1H, J=7.7), 7.78 (m, 2H), 7.69 (dm, 1H, 7.8), 7.60 (dm, 1H, J=7.8), 7.56 (t, 1H, J=7.7), 7.44 (t, 1H, J=7.8); $^{13}$C NMR δ 191.30, 137.13, 136.59, 136.27, 134.81, 133.21, 132.90, 129.61, 129.26, 123.99, 123.69, 118.16, 105.22, 89.72, 88.64, 81.77, 63.62; LRMS (GC/MS, CH$_2$Cl$_2$) m/e 255 (M$^+$)

Synthesis of 2-tert-butyl-3-[2-(tert-butyldimethyl-silanyl)-3-nitrone-azulen-1-yl]-5-[3-(3-formyl-phenylethynyl)-phenyl]-2,3-dihydro-isoxazole-4-carbonitrile (64)

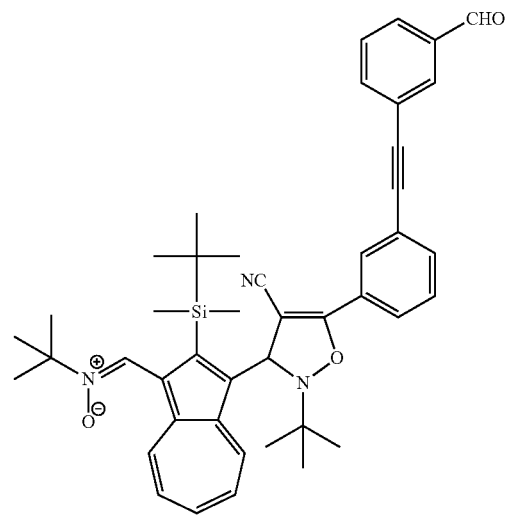 [SMILES: CC(C)(C)N1OC(c2cccc(C#Cc3cccc(C=O)c3)c2)=C(C#N)C1c1c2cccccc-2c(/C=[N+](\[O-])C(C)(C)C)c1[Si](C)(C)C(C)(C)C]

According to the literature procedure, 288 mg of dinitrone 55 (0.65 mmol) was mixed with 17.4 mg of [3-(3-Formyl-phenylethynyl)-phenyl]-propyne nitrile 63 (0.65 mmol), and dissolved in 8 ml of anhydrous benzene. The reaction mixture was then heated at 50° C. for 1 week. The solvent was then dried in vacuo to afford a green solid which was purified by column chromatography on silica gel. The column was washed with 7:3 hexane:ethylacetate to elute 380 mg of aldehyde 64 as green crystals in 84% yield with 16% of starting materials 55. $^1$H NMR δ 10.02 (s, 1H), 9.23 (d, 1H, J=9.8), 8.21 (d, 1H, J=10.1), 8.19, (s, 1H), 8.06 (s, 1H,), 8.04 (s, 1H), 7.94 (dm, 1H, J=8.1), 7.87 (dm, 1H, J=7.7), 7.80 (dm, 1H, J=7.7), 7.68 (m, 2H), 7.54 (t, 1H, J=7.7), 7.47 (t, 1H, J=7.8), 7.34 (t, 1H, J=9.8), 7.28 (t, 1H, J=10.1), 6.36 (s, 1H), 1.71 (s, 9H), 1.27 (s, 9H), 1.00 (s, 9H); $^{13}$C NMR δ 191.43, 160.59, 146.86, 140.65, 139.46, 138.62, 137.19, 137.17, 137.02, 136.57, 135.05, 134.61, 133.13, 130.03, 129.37, 129.25, 129.20, 129.12, 127.20, 126.33, 125.72, 124.98, 124.77, 124.02, 123.70, 115.89, 89.64, 89.19, 86.61, 70.12, 65.39, 61.96, 28.39, 28.03, 25.43, 19.20, 0.27, −1.25; LRMS (LC/MS-ESI, MeOH) m/e 696 (MH$^+$)

Synthesis of 2-tert-butyl-3-[2-(tert-butyldimethyl-silanyl)-3-nitrone-azulen-1-yl]-5-[3-(3-guanylhydra-zone-phenylethynyl)-phenyl]-2,3-dihydro-isoxazole-4-carbonitrile (25)

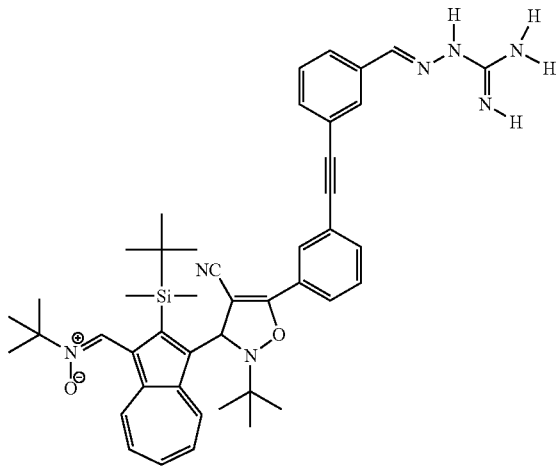 [SMILES: [H]/N=C(\N)N/N=C/c1cccc(C#Cc2cccc(C3=C(C#N)C(c4c5cccccc-5c(/C=[N+](\[O-])C(C)(C)C)c4[Si](C)(C)C(C)(C)C)N(C(C)(C)C)O3)c2)c1]

554 mg of 64 (0.797 mmol) was mixed with 88.2 mg of aminoguanidine hydrochloride (0.797 mmol) and 0.33 ml of triethylamine (2.39 mmol). To this mixture was added 1.5 ml of pyridine to dissolve. The reaction mixture was then stirred for 7 days at 45° C. The resulting green reaction solution was then treated with 5 ml of water and extracted with dichloromethane (6×10 ml). The combined organic phases were then washed with 10 ml of saturated sodium chloride, dried over anhydrous magnesium sulfate, filtered, and evaporated in vacuo to obtain green solid. The green residue was then purified by column chromatography on silica gel. The column was first washed with 60:40 hexane:ethylacetate to collect 10 mg of starting material 64. The polarity of solvent was then increased to 95:5 chloroform:methanol to wash the column to afford 570 mg of nitrone 25 in 95% yield as a green crystal. $^1$H NMR δ 9.43 (d, 1H, J=9.88), 8.33 (s, 1H), 8.01 (s, 1H), 8.00 (d, 1H, J=9.50), 7.90 (s, 1H), 7.70-7.80 (m, 4H), 7.39 (d, 1H, J=7.80) 7.58 (d, 1H, J=8.29), 7.20-7.44 (m, 5H), 6.30 (s, 1H), 1.7 (s, 9H), 1.25 (s, 9H), 1.04 (s, 9H), 0.7 (s, 3H), 0.5 (s, 3H); $^{13}$C NMR δ 160.71, 155.80, 147.18, 146.03, 140.26, 140.10, 137.81, 137.75, 136.79, 134.90, 134.26, 133.40, 132.76, 131.74, 130.58, 130.17, 128.97, 128.75, 127.63, 126.47, 126.22, 125.87, 125.39, 124.06, 123.79, 123.02, 116.18, 90.66, 88.85, 86.22, 70.20, 65.40, 61.77, 28.26, 28.01, 25.36, 19.17, −0.08, −1.17; LRMS (LC/MS-ESI, MeOH) m/e 752 (MH$^+$)

Synthesis of 2-tert-butyldimethylsilyl-1,3-azulenyldioxime (48)

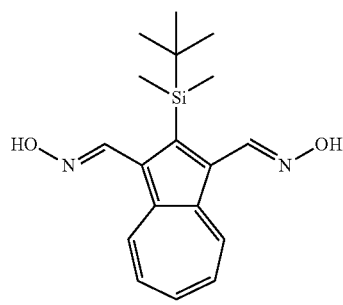 [SMILES: CC(C)(C)[Si](C)(C)c1c(/C=N/O)c2cccccc-2c1/C=N/O]

In an attempt to synthesize nitrone oxime 46, 13 mg of mononitrone 23 (0.0352 mmol) was mixed with 2.5 mg of hydroxylamine hydrochloride (0.0352 mmol) and dissolved in 1 ml of pyridine in a small vial under argon. The reaction mixture was heated at 40° C. After 2 hr of stirring, no product has been observed by TLC so 1 more equivalent of hydroxylamine hydrochloride was added and stirred the reaction mixture for further 24 hr. When TLC showed no more reactant, 8 ml of water was added to the resulting reaction mixture and extracted with ethylacetate (3×10 ml). The combined organic layer was washed with 10 ml saturated sodium chloride solution, dried over anhydrous magnesium sulfate, filtered and concentrated in vacuo. Purification of the resulting green solid by column chromatography on silica gel using 7:3 hexane:ethylacetate failed to provide nitrone oxime 46 indicated by NMR and LRMS. Instead 10 mg of dioxime 48 as green crystals in 87% yield was obtained confirmed by NMR and LRMS. $^1$H NMR δ 9.22 (d, 2H, J=9.6), 8.80 (s, 2H), 7.70 (t, 1H, J=9.8), 7.5 (br s, 2H), 7.39 (t, 1H, J=10) 0.99 (s, 9H), 0.52 (s, 6H); $^{13}$C NMR δ 150.80, 150.05, 140.67, 139.87, 138.51, 127.38, 127.08, 26.98, 18.46, −0.74; LRMS (LC/MS-ESI, MeOH) m/e 329 (MH$^+$)

Attempted Synthesis of 2-Tert-Butyldimethylsilyl-3-Nitrone-1-Azulenemalonolitrile (41)

According to the literature procedure, to a mixture of 15 mg of mononitrone 23 (0.041 mmol) and 2.7 mg of malononitrile (0.041 mmol) in 0.5 ml of dimethylformamide (DMF), 1.7 mg of LiCl (0.0041 mmol) was added and stirred either at room temperature or at 0° C. for 24 hour. TLC showed one reactant spot and another orange spot. The reaction mixture was then treated with 2 ml of water and extracted with 5 ml ethylacetate several times. The combined ethylacetate layers were dried over magnesium sulfate and concentrated in vacuo. The resulting residue was purified by column chromatography. The column was washed first with 5:5 ethylacetate/hexane to collect 3.6 mg of starting material then polarity was increased to 80% to collect 7.3 mg of an orange product. An unidentified orange product has been observed by $^1$H NMR that contained no tert-butyl and methyl groups attached to silyl group. The compound has not been identified yet.

Attempted Synthesis of Isoxazole Tricarboxylic Acid Trimethylester (44)

Based on the reported procedure, 10 mg of mononitrone 23 (0.0271 mmol) was treated with 13.3 μl dimethyl acetylenedicarboxylate (0.108 mmol, 4 equiv.) and dissolved in 0.2 ml of dichloromethane. The reaction mixture was stirred at room temperature for 11 hr. Evaporation followed by purification on column chromatography using 7:3 hexane:ethylacetate gave 5 mg of purple product. However, the purple compound is identified as an intermediate 43 based on $^1$H NMR and MS. Therefore, the reaction is further stirred for 7 days at 35° C. but only the intermediate compound was recovered.

Attempted Synthesis of 54 from p-Formyl Isocyanate and Aminofuran Adduct (50)

According to a modified method from Fowler given in the literature, treatment of 3.4 mg of p-formyl isocyanate 53 (0.022 mmol) with 12 mg of aminofuran adduct 50 (0.022 mmol) dissolved either 0.2 ml of benzene or toluene and heated at 90° C. for 7 days failed to show any product by TLC. The solvent was then removed by rotator evaporation. Recrystallized from ether gave 12 mg of wine red solid (89%) which is identical to the starting material 50 confirmed by TLC and $^1$H NMR.

Attempted Synthesis of α,β-Unsaturated Ketone Derivative of Isoxazoline (57)

7.2 mg of carboxynitrile compound 24 (0.0127 mmol) was treated with 0.04 ml of iodomethane (0.609 mmol) and 64 mg of poly-4 vilylpyridine (0.609 mmol) and dissolved in 0.5 ml of THF. The reaction was stirred 40° C. for 36 hour. After three product were observed by TLC, the reaction mixture was filtered and washed with 15 ml of hexane:ethylacetate and concentrated in vacuo. The resulting residue was then chromatographed on silica gel by washing the column with 8:2 hexane:ethylacetate to collect the first two purple products 1.5 mg and 3 mg respectively and then polarity was increased to 5:5 ethylacetate:hexane to collect 1 gm of green product and 0.8 mg of starting material. However, the mixture of products failed to indicate the presence of 57 by $^1$H NMR and LRMS. Three products were presumed to be 58, 59 and 60 based on their LRMS data.

Aldehyde Product (67) of Superoxide Trapping with Nitrone 22

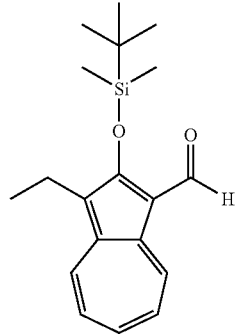 [SMILES: CCc1c2cccccc-2c(C=O)c1O[Si](C)(C)C(C)(C)C]

6 mg of nitrone 22 (0.0163 mmol) was mixed with 6.9 mg of potassium superoxide (0.097 mmol, 6 equiv.) and 8.6 mg of crown ether (0.032 mmol, 2 equiv.) and dissolved the mixture in 1 ml of benzene. The reaction was stirred for 3 hr at room temperature. The product was washed with 10 ml of saturated sodium chloride several times, dried over magnesium sulfate and concentrated. The mixture was purified by column chromatography using 5:5 hexane:ethylacetate to give 2.2 mg of crude 67 (43%). It was not possible to obtain 67 pure enough for definitive NMR characterization. Nevertheless, the presence of aldehyde-proton and up-field shifting of ethyl-proton in $^1$H NMR data suggested the compound 67. When the same reaction was stirred for three days, another orange product was observed. The $^1$H NMR was observed with no aldehyde-proton signal and LRMS detected MH$^+$ of 663. Impossible to isolate this product in pure form, the structure was not identified.

Amide Products 74 and 79 of Superoxide Trapping with Nitrone 24

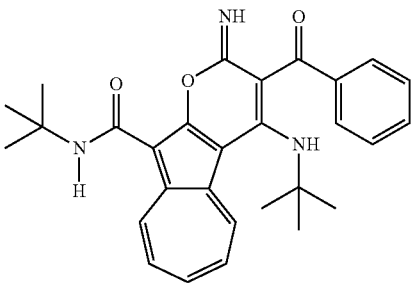

74

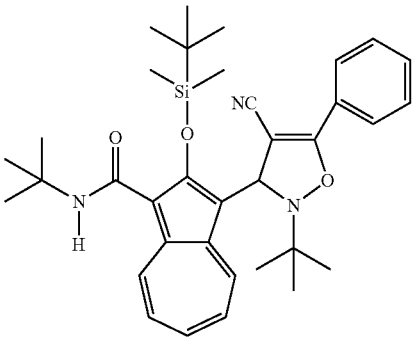

79

20 mg of nitrone 24 was treated with 7.5 mg of potassium superoxide and 18.6 mg of crown ether in 1 ml of benzene. The reaction was stirred for 16 hr at room temperature. The mixture was then washed with 10 ml of saturated sodium chloride several times, dried and concentrated. Purification of the mixture product by column chromatography using 5:5 ethylacetate:hexane afforded 7.2 mg of orange amide 74 in 44% yield. $^1$H NMR δ 8.8 (s, 1H), 7.7 (d, 1H J=10.3), 7.63 (m, 2H), 7.56 (m, 1H), 7.40 (t, 1H J=7.3), 7.7.33-7.22 (m, 4H), 7.0 (m, 1H), 6.24 (s, 1H), 1.57 (s, 9H), 1.48 (s, 9H); $^{13}$C NMR δ 190.81, 172.62, 168.62, 157.58, 138.93, 138.43, 135.46, 133.20, 131.36, 128.35, 127.83, 127.12, 125.92, 125.11, 124.81, 122.05, 116.53, 115.0, 83.68, 63.42, 52.90, 29.90, 28.99; LRMS (LC/MS-ESI, MeOH) m/e 470 (MH$^+$); HRMS calculated for $C_{29}H_{31}O_3N_3$ 470. In addition to compound 74, trace of amide 79 was also recovered which was not enough for NMR characterization. However, it was possible to obtain consistent MS data: LRMS (LC/MS-ESI, MeOH) m/e 584 (MH$^+$).

Amide Products 80 and 81 of Superoxide Trapping by Nitrone 25

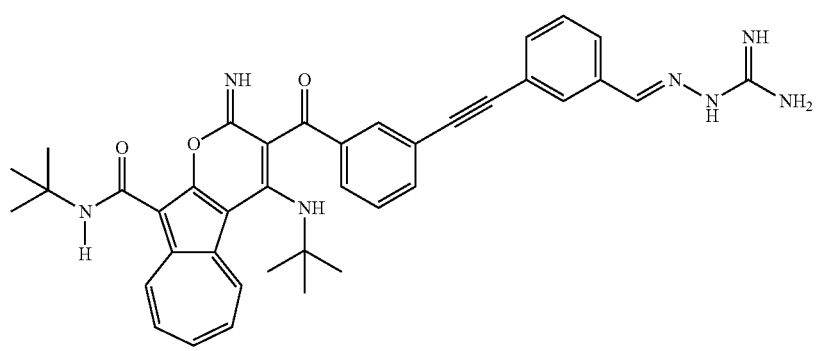

80

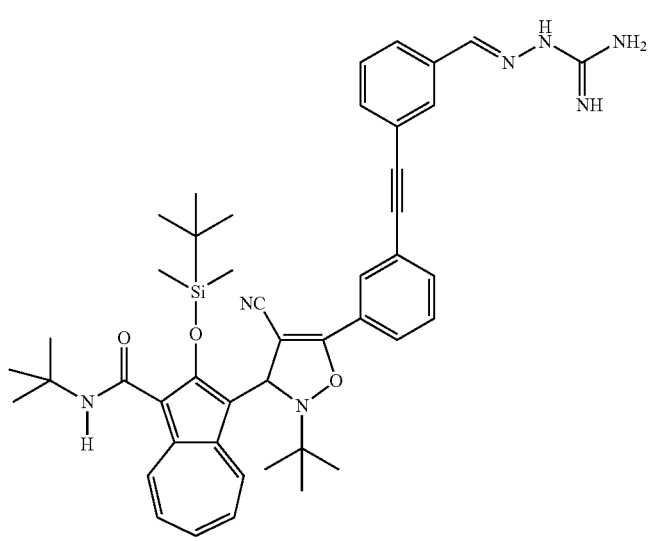

81

15 mg of nitrone 25 (0.021 mmol) was treated with 4.4 mg (3 equiv.) of potassium superoxide and 11.1 mg (2 equiv.) of crown ether in 1 ml of benzene and stirred for 19 hr. Work up was done as aforementioned method. The mixture product was separated by column chromatography beginning with 98:2 dichloromethane:methanol and increasing the polarity to 94:6 dichloromethane:methanol to provide crude brownish orange product. LRMS analysis indicated the compound 80 with 654 ($MH^+$) as a major product and the compound 81 with 768 ($MH^+$) as a minor product along with some starting material. It was not possible to separate the mixture pure enough for NMR characterization.

UV-Vis and Fluorescence Analysis

UV-vis and Fluorescence experiments were performed with assistance of Dr. Moon's students. The orange product 74 from the reaction of 2-tert-butyldimethylsilyl-3-tert-butylnitrone-1-(2-tert-butyl-4-cyano-5-phenyl)-azulenylisoxazoline (24) with superoxide was tested. Compound 74 was dissolved in ethanol for UV-vis absorbance measurement in scan range of 200-400 nm with scan rate of 600 nm/min at average time 0.1 s and data interval of 1.00 nm. Fluorescence signal was obtained in scan range of 400-700 nm using 0.1 s integration time with an increment of 0.1 nm. Both the excitation slit wide and the emission slit wide were selected 1.5 nm with the excitation wavelength fixed at 390 nm.

LIST OF REFERENCES (1) Fridovich, I.: Superoxide radical: an endogenous toxicant. Annu. Rev. Pharmacol. Toxicol. 1983, 23, 239-57.
(2) Droge, W.: Free radicals in the physiological control of cell function. Physiol. Rev. 2002, 82, 47-95.
(3) Valko, M.; Leibfritz, D.; Moncol, J.; Cronin Mark, T. D.; Mazur, M.; Telser, J.: Free radicals and antioxidants in normal physiological functions and human disease. Int J Biochem Cell Biol 2007, 39, 44-84.
(4) Liochev, S. I.; Fridovich, I.: Lucigenin (bis-N-methylacridinium) as a mediator of superoxide anion production. Arch. Biochem. Biophys. 1997, 337, 115-120.
(5) Vasquez-Vivar, J.; Hogg, N.; Pritchard, K. A., Jr.; Martasek, P.; Kalyanaraman, B.: Superoxide anion formation from lucigenin: an electron spin resonance spin-trapping study. FEBS Lett. 1997, 403, 127-130.
(6) Benov, L.; Sztejnberg, L.; Fridovich, I.: Critical evaluation of the use of hydroethidine as a measure of superoxide anion radical. Free Radical Biol. Med. 1998, 25, 826-831.
(7) Frey, C.; Narayanan, K.; McMillan, K.; Spack, L.; Gross, S. S.; Masters, B. S.; Griffith, O. W.: L-Thiocitrulline. A stereospecific, heme-binding inhibitor of nitric-oxide synthases. J. Biol. Chem. 1994, 269, 26083-91.
(8) Gomberg, M.: An instance of trivalent carbon: triphenylmethyl. J. Am. Chem. Soc. 1900, 22, 757-71.
(9) Gerschman, R.; Gilbert, D. L.; Nye, S. W.; Dwyer, P.; Fenn, W. O.: Oxygen poisoning and x-irradiation: mechanism in common. Science (Washington, D.C., U.S.) 1954, 119, 623-6.
(10) Commoner, B.; Townsend, J.; Pake, G. E.: Free radicals in biological materials. Nature (London, U. K.) 1954, 174, 689-91.
(11) Harman, D.: Aging: a theory based on free radical and radiation chemistry. J Gerontol 1956, 11, 298-300.
(12) McCord, J. M.; Fridovich, I.: Superoxide dismutase. Enzymic function for erythrocuprein (hemocuprein). J. Biol. Chem. 1969, 244, 6049-55.
(13) Mittal, C. K.; Murad, F.: Activation of guanylate cyclase by superoxide dismutase and hydroxyl radical: A physiological regulator of guanosine 3',5'-monophosphate formation. Proc. Natl. Acad. Sci. U.S.A. 1977, 74, 4360-4.
(14) Babior, B. M.: Oxygen-dependent microbial killing by phagocytes. Part 1. N. Engl. J. Med. 1978, 298, 659-68.
(15) Babior, B. M.: Phagocytes and oxidative stress. Am. J. Med. 2000, 109, 33-44.
(16) Griendling, K. K.; Sorescu, D.; Lassegue, B.; Ushio-Fukai, M.: Modulation of protein kinase activity and gene expression by reactive oxygen species and their role in vascular physiology and pathophysiology. Arterioscler., Thromb., Vasc. Biol. 2000, 20, 2175-2183.
(17) Roth, S.; Droege, W.: Regulation of T-cell activation and T-cell growth factor (TCGF) production by hydrogen peroxide. Cell. Immunol. 1987, 108, 417-24.
(18) Pratico, D.; Lee, V. M. Y.; Trojanowski, J. Q.; Rokach, J.; Fitzgerald, G. A.: Increased F2-isoprostanes in Alzheimer's disease: evidence for enhanced lipid peroxidation in vivo. Faseb J. 1998, 12, 1777-1783.
(19) Zweier, J. L.; Talukder, M. A. H.: The role of oxidants and free radicals in reperfusion injury. Cardiovasc. Res. 2006, 70, 181-190.

(20) Hussain, S. P.; Aguilar, F.; Amstad, P.; Cerutti, P.: Oxyradical induced mutagenesis of hotspot codons 248 and 249 of the human p53 gene. Oncogene 1994, 9, 2277-81.

(21) Nakamura, Y.; Colburn, N. H.; Gindhart, T. D.: Role of reactive oxygen in tumor promotion: implication of superoxide anion in promotion of neoplastic transformation in JB-6 cells by TPA. Carcinogenesis (London) 1985, 6, 229-35.

(22) Alexandrova, M. L.; Bochev, P. G.: Oxidative stress during the chronic phase after stroke. Free Radical Biol. Med. 2005, 39, 297-316.

(23) Sayre, L. M.; Zelasko, D. A.; Harris, P. L. R.; Perry, G.; Salomon, R. G.; Smith, M. A.: 4-Hydroxynonenal-derived advanced lipid peroxidation end products are increased in Alzheimer's disease. J. Neurochem. 1997, 68, 2092-2097.

(24) Pratico, D.; V, M. Y. L.; Trojanowski, J. Q.; Rokach, J.; Fitzgerald, G. A.: Increased F2-isoprostanes in Alzheimer's disease: evidence for enhanced lipid peroxidation in vivo. Faseb J 1998, 12, 1777-83.

(25) Tsutsui, H.; Kinugawa, S.; Matsushima, S.: Mitochondrial oxidative stress and dysfunction in myocardial remodelling. Cardiovasc. Res. 2009, 81, 449-456.

(26) Sayre, L. M.; Perry, G.; Smith, M. A.: Oxidative Stress and Neurotoxicity. Chem. Res. Toxicol. 2008, 21, 172-188.

(27) Busciglio, J.; Yankner, B. A.: Apoptosis and increased generation of reactive oxygen species in Down's syndrome neurons in vitro. Nature (London) 1995, 378, 776-9.

(28) de Haan, J. B.; Cristiano, F.; Iannello, R.; Bladier, C.; Kelner, M. J.; Kola, I.: Elevation in the ratio of Cu/Zn-superoxide dismutase to glutathione peroxidase activity induces features of cellular senescence and this effect is mediated by hydrogen peroxide. Hum. Mol. Genet. 1996, 5, 283-92.

(29) Baynes, J. W.: Role of oxidative stress in development of complications in diabetes. Diabetes 1991, 40, 405-12.

(30) Merritt, M. V.; Sawyer, D. T.: Electrochemical studies of the reactivity of superoxide ion with several alkyl halides in dimethyl sulfoxide. J. Org. Chem. 1970, 35, 2157-9.

(31) Sugimoto, H.; Matsumoto, S.; Sawyer, D. T.: Degradation and dehalogenation of polychlorobiphenyls and halogenated aromatic molecules by superoxide ion and by electrolytic reduction. Environ. Sci. Technol. 1988, 22, 1182-6.

(32) Arditti, J.; Pridgeonm, A. M.; Editors: Orchid Biology: Reviews and Perspectives, VII, 1997.

(33) Gruenwedel, D. W.; Whitaker, J. R.; Editors: Food Analysis: Principles and Techniques, Vol. 4: Separation Techniques, 1987.

(34) Bergendi, L.; Benes, L.; Durackova, Z.; Ferencik, M.: Chemistry, physiology and pathology of free radicals. Life Sci. 1999, 65, 1865-1874.

(35) Li, J.; Hou, H.; Wang, B.: Ab Initio Molecular Dynamics Study of the Electronic Structure of Superoxide Radical Anion in Solution. J. Phys. Chem. A 2009, 113, 800-804.

(36) Friestad, G. K.: Ion-Radical Organic Chemistry: Principles and Applications, 2nd ed. by Zory Vlad Todres, 2009; Vol. 131.

(37) Klotz, L.-O.: Oxidant-induced signaling: effects of peroxynitrite and singlet oxygen. Biol. Chem. 2002, 383, 443-456.

(38) Mikkelsen, R. B.; Wardman, P.: Biological chemistry of reactive oxygen and nitrogen and radiation-induced signal transduction mechanisms. Oncogene 2003, 22, 5734-5754.

(39) Ferrari, R.; Ceconi, C.; Curello, S.; Cargnoni, A.; Pasini, E.; De Giuli, F.; Albertini, A.: Role of oxygen free radicals in ischemic and reperfused myocardium. Am. J. Clin. Nutr. 1991, 53, 215S-222S.

(40) Wood, P. M.: The potential diagram for oxygen at pH 7. Biochem. J. 1988, 253, 287-9.

(41) Tarr, M.; Samson, F.: Oxygen Free Radicals in Tissue Damage, 1993.

(42) Rosen, G. M.; Britigan, B. E.; Halpern, H. J.; Pou, S.: Free Radicals: Biology and Detection by Spin Trapping, 1999.

(43) Boveris, A.; Chance, B.: Mitochondrial generation of hydrogen peroxide. General properties and effect of hyperbaric oxygen. Biochem. J. 1973, 134, 707-16.

(44) Floyd, R. A.; West, M.; Hensley, K.: Oxidative biochemical markers; clues to understanding aging in long-lived species. Exp. Gerontol. 2001, 36, 619-640.

(45) Babior, B. M.: NADPH oxidase: an update. Blood 1999, 93, 1464-1476.

(46) Vignais, P. V.: The superoxide-generating NADPH oxidase: structural aspects and activation mechanism. Cell. Mol. Life. Sci. 2002, 59, 1428-1459.

(47) Babior, B. M.: The NADPH oxidase of endothelial cells. IUBMB Life 2000, 50, 267-269.

(48) Moriwaki, Y.; Yamamoto, T.; Higashino, K.: Enzymes involved in purine metabolism—a review of histochemical localization and functional implications. Histol. Histopathol. 1999, 14, 1321-1340.

(49) Harrison, R.: Structure and function of xanthine oxidoreductase: where are we now? Free Radical Biology and Medicine 2002, 33, 774-797.

(50) Pandey, N. R.; Kaur, G.; Chandra, M.; Sanwal, G. G.; Misra, M. K.: Enzymatic oxidant and antioxidants of human blood platelets in unstable angina and myocardial infarction. International Journal of Cardiology 2000, 76, 33-38.

(51) Parks, D. A.; Granger, D. N.: Xanthine oxidase: biochemistry, distribution and physiology. Acta Physiol. Scand., Suppl. 1986, 548, 87-99.

(52) Yamazaki, I.; Yokota, K.: Oxidation states of peroxidase. Mol. Cell. Biochem. 1973, 2, 39-52.

(53) Halliwell, B.: Lignin synthesis: the generation of hydrogen peroxide and superoxide by horseradish peroxidase and its stimulation by manganese(II) and phenols. Planta 1978, 140, 81-8.

(54) De Sandro, V.; Dupuy, C.; Kaniewski, J.; Ohayon, R.; Deme, D.; Virion, A.; Pommier, J.: Mechanism of NADPH oxidation catalyzed by horse-radish peroxidase and 2,4-diacetyl-[2H]heme-substituted horse-radish peroxidase. Eur J Biochem 1991, 201, 507-13.

(55) Halliwell, B.: Generation of the superoxide radical during the peroxidatic oxidation of NADH by catalase at acid pH values. FEBS Lett. 1977, 80, 291-3.

(56) Lynch, D. V.; Thompson, J. E.: Lipoxygenase-mediated production of superoxide anion in senescing plant tissue. FEBS Letters 1984, 173, 251-254.

(57) Roy, P.; Roy, S. K.; Mitra, A.; Kulkarni, A. P.: Superoxide generation by lipoxygenase in the presence of NADH and NADPH. Biochimica et Biophysica Acta (BBA)-Lipids and Lipid Metabolism 1994, 1214, 171-179.

(58) Kukreja, R. C.; Kontos, H. A.; Hess, M. L.; Ellis, E. F.: PGH synthase and lipoxygenase generate superoxide in the presence of NADH or NADPH. Circ. Res. 1986, 59, 612-19.

(59) Kulkarni, M.; Armstead, W. M.: Superoxide generation links nociceptin/orphanin FQ (NOC/oFQ) release to impaired N-methyl-D-aspartate cerebrovasodilation after brain injury. Stroke 2000, 31, 1990-1996.

(60) Jenner, P.: Oxidative stress and Parkinson's disease. In Handbook of Clinical Neurology; Michael J. Aminoff, F. B. D. F. S. W. C. K. a. E. M., Ed.; Elsevier, 2007; Vol. Volume 83; pp 507-520.

(61) Misra, H. P.: Generation of superoxide free radical during the autoxidation of thiols. J. Biol. Chem. 1974, 249, 2151-5.

(62) Jones, G. J.; Waite, T. D.; Smith, J. D.: Light-dependent reduction of copper(II) and its effect on cell-mediated, thiol-dependent superoxide production. Biochemical and Biophysical Research Communications 1985, 128, 1031-1036.

(63) Clement, M.-V.; Sivarajah, S.; Pervaiz, S.: Production of Intracellular Superoxide Mediates Dithiothreitol-Dependent Inhibition of Apoptotic Cell Death. Antioxid. Redox Signaling 2005, 7, 456-464.

(64) Morehouse, L. A.; Aust, S. D.: Generation of superoxide by the microsomal mixed-function oxidase system. Basic Life Sci. 1988, 49, 517-21.

(65) Aust, S. D.; Roerig, D. L.; Pederson, T. C.: Evidence for superoxide generation by NADPH-cytochrome c reductase of rat liver microsomes. Biochem. Biophys. Res. Commun. 1972, 47, 1133-7.

(66) Sipowicz, M. A.; Chomarat, P.; Diwan, B. A.; Anver, M. A.; Awasthi, Y. C.; Ward, J. M.; Rice, J. M.; Kasprzak, K. S.; Wild, C. P.; Anderson, L. M.: Increased oxidative DNA damage and hepatocyte overexpression of specific cytochrome P450 isoforms in hepatitis of mice infected with *Helicobacter hepaticus*. Am. J. Pathol. 1997, 151, 933-941

(67) Nelson, D. H.; Ruhmann-Wennhold, A.: Corticosteroids increase superoxide anion production by rat liver microsomes. J. Clin. Invest. 1975, 56, 1062-5.

(68) Barton, G. M.; Galeotti, T.; Azzi, A.: Production of superoxide anions and hydrogen peroxide in Ehrlich ascites tumour cell nuclei. Biochimica et Biophysica Acta (BBA)—General Subjects 1977, 497, 622-626.

(69) Peskin, A. V.; Koen, Y. M.; Zbarskii, I. B.: Superoxide dismutase and glutathione peroxidase activities in tumors. FEBS Lett. 1977, 78, 41-5.

(70) Tarakhovskii, A. M.; Shlyakhovenko, V. A.; Zhmareva, E. N.; Brodskaya, I. A.; Peskin, A. V.; Zbarskii, I. B.: Formation of superoxide radicals by nuclear membranes of human brain tumors. Byull. Eksp Biol. Med. 1985, 99, 88-90.

(71) Vasquez-Vivar, J.; Kalyanaraman, B.; Martasek, P.; Hogg, N.; Masters, B. S. S.; Karoui, H.; Tordo, P.; Pritchard, K. A., Jr.: Superoxide generation by endothelial nitric oxide synthase: the influence of cofactors. Proc. Natl. Acad. Sci. U.S.A. 1998, 95, 9220-9225.

(72) Fridovich, I.: Evidence for the symbiotic origin of mitochondria. Life Sci 1974, 14, 819-26.

(73) Fahl, W. E.; Lalwani, N. D.; Watanabe, T.; Goel, S. K.; Reddy, J. K.: DNA damage related to increased hydrogen peroxide generation by hypolipidemic drug-induced liver peroxisomes. Proc. Natl. Acad. Sci. U.S.A. 1984, 81, 7827-30.

(74) Prütz, W. A.; Butler, J.; Land, E. J.: The glutathione free radical equilibrium, GS.+GS—[right harpoon over left] GSS.-G, mediating electron transfer to FE(III)-cytochrome c. Biophysical Chemistry 1994, 49, 101-111.

(75) Maddipati, K. R.; Gasparski, C.; Marnett, L. J.: Characterization of the hydroperoxide-reducing activity of human plasma. Arch. Biochem. Biophys. 1987, 254, 9-17.

(76) Prousek, J.: Fenton reaction after a century. Chem. Listy 1995, 89, 11-21.

(77) Chance, B.; Sies, H.; Boveris, A.: Hydroperoxide metabolism in mammalian organs. Physiol. Rev. 1979, 59, 527-605.

(78) Koppenol, W. H.: The Haber-Weiss cycle—70 years later. Redox Rep. 2001, 6, 229-234.

(79) Engelmann, M. D.; Bobier, R. T.; Hiatt, T.; Cheng, I. F.: Variability of the Fenton reaction characteristics of the EDTA, DTPA, and citrate complexes of iron. BioMetals 2003, 16, 519-527.

(80) Cairo, G.; Recalcati, S.; Pietrangelo, A.; Minotti, G.: The iron regulatory proteins: targets and modulators of free radical reactions and oxidative damage. Free Radical Biol. Med. 2002, 32, 1237-1243.

(81) Candeias, L. P.; Patel, K. B.; Stratford, M. R. L.; Wardman, P.: Free hydroxyl radicals are formed on reaction between the neutrophil-derived species superoxide anion and hypochlorous acid. FEBS Lett. 1993, 333, 151-3.

(82) Kanofsky, J. R.: Singlet oxygen production by lactoperoxidase. Evidence from 1270 nm chemiluminescence. J. Biol. Chem. 1983, 258, 5991-3.

(83) Kanofsky, J. R.: Singlet oxygen production by chloroperoxidase-hydrogen peroxide-halide systems. J. Biol. Chem. 1984, 259, 5596-600.

(84) McCormick, M. L.; Roeder, T. L.; Railsback, M. A.; Britigan, B. E.: Eosinophil peroxidase-dependent hydroxyl radical generation by human eosinophils. J. Biol. Chem. 1994, 269, 27914-19.

(85) Stuehr, D. J.; Marletta, M. A.: Induction of nitrite/nitrate synthesis in murine macrophages by BCG infection, lymphokines, or interferon-γ. J. Immunol. 1987, 139, 518-25.

(86) Ignarro, L. J.: Nitric oxide: a unique endogenous signaling molecule in vascular biology. Prix Nobel 1999, 252-272.

(87) Radi, R.: Peroxynitrite Reactions and Diffusion in Biology. Chem. Res. Toxicol. 1998, 11, 720-721.

(88) Beckman, J. S.; Beckman, T. W.; Chen, J.; Marshall, P. A.; Freeman, B. A.: Apparent hydroxyl radical production by peroxynitrite: implications for endothelial injury from nitric oxide and superoxide. Proc. Natl. Acad. Sci. U.S.A. 1990, 87, 1620-4.

(89) Beckman, J. S.; Koppenol, W. H.: Nitric oxide, superoxide, and peroxynitrite: the good, the bad, and the ugly. Am. J. Physiol. 1996, 271, C1424-C1437.

(90) Uppu, R. M.; Squadrito, G. L.; Pryor, W. A.: Acceleration of peroxynitrite oxidations by carbon dioxide. Arch. Biochem. Biophys. 1996, 327, 335-43.

(91) Augusto, O.; Bonini, M. G.; Amanso, A. M.; Linares, E.; Santos, C. C. X.; De Menezes, S. L.: Nitrogen dioxide and carbonate radical anion: two emerging radicals in biology. Free Radical Biol. Med. 2002, 32, 841-859.

(92) Esterbauer, H.; Schaur, R. J.; Zollner, H.: Chemistry and biochemistry of 4-hydroxynonenal, malonaldehyde and related aldehydes. Free Radical Biology and Medicine 1991, 11, 81-128.

(93) Sayre, L. M.; Smith, M. A.; Perry, G.: Chemistry and biochemistry of oxidative stress in neurodegenerative disease. Curr. Med. Chem. 2001, 8, 721-738.

(94) Farooqui, A. A.; Horrocks, L. A.: Lipid peroxides in the free radical pathophysiology of brain diseases. Cell. Mol. Neurobiol. 1998, 18, 599-608.

(95) Aikens, J.; Dix, T. A.: Perhydroxyl radical (HOO.bul.) initiated lipid peroxidation. The role of fatty acid hydroperoxides. J. Biol. Chem. 1991, 266, 15091-8.

(96) Breen, A. P.; Murphy, J. A.: Reactions of oxyl radicals with DNA. Free Radical Biology and Medicine 1995, 18, 1033-1077.

(97) Steenken, S.: Purine bases, nucleosides, and nucleotides: aqueous solution redox chemistry and transformation reactions of their radical cations and e- and OH adducts. Chem. Rev. 1989, 89, 503-20.

(98) Vieira, A. J. S. C.; Candeias, L. P.; Steenken, S.: Hydroxyl radical induced damage to the purine bases of DNA: in vitro studies. J. Chim. Phys. Phys.-Chim. Biol. 1993, 90, 881-97.

(99) Grollman, A. P.; Moriya, M.: Mutagenesis by 8-oxoguanine: an enemy within. Trends in Genetics 1993, 9, 246-249.

(100) Cadet, J.; Delatour, T.; Douki, T.; Gasparutto, D.; Pouget, E.-P.; Ravanat, J.-L.; Sauvaigo, S.: Hydroxyl radicals and DNA base damage. Mutat. Res., Fundam. Mol. Mech. Mutagen. 1999, 424, 9-21.

(101) Guyton, K. Z.; Kensler, T. W.: Oxidative mechanisms in carcinogenesis. Br. Med. Bull. 1993, 49, 523-44.

(102) Stadtman, E. R.: Protein oxidation in aging and age-related diseases. Ann. N.Y. Acad. Sci. 2000, 928, 22-38.

(103) Stadtman, E. R.: Metal ion-catalyzed oxidation of proteins: biochemical mechanism and biological consequences. Free Radic Biol Med 1990, 9, 315-25.

(104) Davies, K. J. A.: Protein damage and degradation by oxygen radicals. I. General aspects. J. Biol. Chem. 1987, 262, 9895-901.

(105) Dean, R. T.; Fu, S.; Stocker, R.; Davies, M. J.: Biochemistry and pathology of radical-mediated protein oxidation. Biochem. J. 1997, 324, 1-18.

(106) Levine, R. L.; Stadtman, E. R.: Oxidative modification of proteins during aging. Experimental Gerontology 2001, 36, 1495-1502.

(107) Viner, R. I.; Williams, T. D.; Schoeneich, C.: Peroxynitrite modification of protein thiols: Oxidation, nitrosylation, and S-glutathiolation of functionally important cysteine residue(s) in the sarcoplasmic reticulum Ca-ATPase. Biochemistry 1999, 38, 12408-12415.

(108) Pryor, W. A.; Squadrito, G. L.: The chemistry of peroxynitrite: a product from the reaction of nitric oxide with superoxide. Am. J. Physiol. 1995, 268, L699-L722.

(109) Cadenas, E.: Basic mechanisms of antioxidant activity. BioFactors 1997, 6, 391-397.

(110) Oberley, L. W.; Buettner, G. R.: Role of superoxide dismutase in cancer: a review. Cancer Res 1979, 39, 1141-9.

(111) Halliwell, B.; Gutteridge, J. M. C.: Free Radicals in Biology and Medicine, 1988.

(112) Sies, H.: Strategies of antioxidant defense. Eur. J. Biochem. 1993, 215, 213-19.

(113) Durackova, Z.: Antioxidants as good and bad compounds. Klin. Biochem. Metab. 1997, 5, 194-199.

(114) Schafer, F. Q.; Buettner, G. R.: Redox environment of the cell as viewed through the redox state of the glutathione disulfide/glutathione couple. Free Radical Biol. Med. 2001, 30, 1191-1212.

(115) Akerboom, T. P. M.; Sies, H.: Assay of glutathione, glutathione disulfide, and glutathione mixed disulfides in biological samples. Methods Enzymol. 1981, 77, 373-82.

(116) Black, S.: The biochemistry of sulfur-containing compounds. Annu. Rev. Biochem. 1963, 32, 399-418.

(117) Milne, L.; Nicotera, P.; Orrenius, S.; Burkitt, M. J.: Effects of glutathione and chelating agents on copper-mediated DNA oxidation: pro-oxidant and antioxidant properties of glutathione. Arch Biochem Biophys 1993, 304, 102-9.

(118) Griscavage, J. M.; Fukuto, J. M.; Komori, Y.; Ignarro, L. J.: Nitric oxide inhibits neuronal nitric oxide synthase by interacting with the heme prosthetic group. Role of tetrahydrobiopterin in modulating the inhibitory action of nitric oxide. J. Biol. Chem. 1994, 269, 21644-9.

(119) Hack, V.; Schmid, D.; Breitkreutz, R.; Stahl-Henning, C.; Drings, P.; Kinscherf, R.; Taut, F.; Holm, E.; Droege, W.: Cystine levels, cystine flux, and protein catabolism in cancer cachexia, HIV/SIV infection, and senescence. Faseb J. 1997, 11, 84-92.

(120) De Mattia, G.; Bravi, M. C.; Laurenti, O.; Cassone-Faldetta, M.; Armiento, A.; Ferri, C.; Balsano, F.: Influence of reduced glutathione infusion on glucose metabolism in patients with non-insulin-dependent diabetes mellitus. Metab., Clin. Exp. 1998, 47, 993-997.

(121) Nathan, C.: Points of control in inflammation. Nature (London, U. K.) 2002, 420, 846-852.

(122) Hengartner, M. O.: The biochemistry of apoptosis. Nature (London) 2000, 407, 770-776.

(123) Hussain, S. P.; Hofseth, L. J.; Harris, C. C.: Radical causes of cancer. Nat. Rev. Cancer 2003, 3, 276-285.

(124) Cooke, M. S.; Evans, M. D.; Dizdaroglu, M.; Lunec, J.: Oxidative DNA damage: mechanisms, mutation, and disease. Faseb J. 2003, 17, 1195-1214, 10 1096/fj 02-0752rev.

(125) Marnett, L. J.: Oxyradicals and DNA damage. Carcinogenesis 2000, 21, 361-370.

(126) Shigenaga, M. K.; Gimeno, C. J.; Ames, B. N.: Urinary 8-hydroxy-2'-deoxyguanosine as a biological marker of in vivo oxidative DNA damage. Proc. Natl. Acad. Sci. U.S.A. 1989, 86, 9697-701.

(127) Loft, S.; Poulsen, H. E.: Cancer risk and oxidative DNA damage in man. J. Mol. Med. (Berlin) 1996, 74, 297-312.

(128) Wolff, S. P.: Diabetes mellitus and free radicals. Free radicals, transition metals and oxidative stress in the etiology of diabetes mellitus and complications. Br. Med. Bull. 1993, 49, 642-52.

(129) Nishikawa, T.; Edelstein, D.; Du, X. L.; Yamagishi, S.-I.; Matsumura, T.; Kaneda, Y.; Yorek, M. A.; Beebe, D.; Oates, P. J.; Hammes, H.-P.; Giardino, I.; Brownlee, M.: Normalizing mitochondrial superoxide production blocks three pathways of hyperglycemic damage. Nature (London) 2000, 404, 787-791.

(130) Oberley, L. W.: Free radicals and diabetes. Free Radic Biol Med 1988, 5, 113-24.

(131) van Dam, P. S.; van Asbeck, B. S.; Erkelens, D. W.; Marx, J. J. M.; Gispen, W.-H.; Bravenboer, B.: The role of oxidative stress in neuropathy and other diabetic complications. Diabetes/Metab. Rev. 1995, 11, 181-92.

(132) Yan, S. D.; Schmidt, A. M.; Anderson, G. M.; Zhang, J.; Brett, J.; Zou, Y. S.; Pinsky, D.; Stern, D.: Enhanced cellular oxidant stress by the interaction of advanced glycation end products with their receptors/binding proteins. J. Biol. Chem. 1994, 269, 9889-97.

(133) Aragno, M.; Parola, S.; Tamagno, E.; Brignardello, E.; Manti, R.; Danni, O.; Boccuzzi, G.: Oxidative derangement in rat synaptosomes induced by hyperglycaemia: restorative effect of dehydroepiandrosterone treatment. Biochemical Pharmacology 2000, 60, 389-395.

(134) Reusch, J. E. B.: Diabetes, microvascular complications, and cardiovascular complications: What is it about glucose? J. Clin. Invest. 2003, 112, 986-988.

(135) Halliwell, B.: Free radicals, reactive oxygen species and human disease: a critical evaluation with special reference to atherosclerosis. Br J Exp Pathol 1989, 70, 737-57.

(136) Alexander, R. W.: Hypertension and the pathogenesis of atherosclerosis. Oxidative stress and the mediation of arterial inflammatory response: a new perspective. Hypertension (Dallas) 1995, 25, 155-61.

(137) Kinscherf, R.; Wagner, M.; Kamencic, H.; Bonaterra, G. A.; Hou, D.; Schiele, R. A.; Deigner, H.-P.; Metz, J.: Characterization of apoptotic macrophages in atheromatous tissue of humans and heritable hyperlipidemic rabbits. Atherosclerosis 1999, 144, 33-39.

(138) Chobanian, A. V.; Lichtenstein, A. H.; Nilakhe, V.; Haudenschild, C. C.; Drago, R.; Nickerson, C.: Influence of hypertension on aortic atherosclerosis in the Watanabe rabbit. Hypertension 1989, 14, 203-9.

(139) Vaziri, N. D.; Wang, X. Q.; Oveisi, F.; Rad, B.: Induction of oxidative stress by glutathione depletion causes severe hypertension in normal rats. Hypertension 2000, 36, 142-146.

(140) Russo, C.; Olivieri, O.; Girelli, D.; Faccini, G.; Zenari, M. L.; Lombardi, S.; Corrocher, R.: Anti-oxidant status and lipid peroxidation in patients with essential hypertension. J. Hypertens. 1998, 16, 1267-1271.

(141) Sagar, S.; Kallo, I. J.; Kaul, N.; Ganguly, N. K.; Sharma, B. K.: Oxygen free radicals in essential hypertension. Mol. Cell. Biochem. 1992, 111, 103-8.

(142) Nakazono, K.; Watanabe, N.; Matsuno, K.; Sasaki, J.; Sato, T.; Inoue, M.: Does superoxide underlie the pathogenesis of hypertension? Proc. Natl. Acad. Sci. U.S.A. 1991, 88, 10045-8.

(143) Grunfeld, S.; Hamilton, C. A.; Mesaros, S.; McClain, S. W.; Dominiczak, A. F.; Bohr, D. F.; Malinski, T.: Role of superoxide in the depressed nitric oxide production by the endothelium of genetically hypertensive rats. Hypertension (Dallas) 1995, 26, 854-7.

(144) Laursen, J. B.; Rajagopalan, S.; Galis, Z.; Tarpey, M.; Freeman, B. A.; Harrison, D. G.: Role of superoxide in angiotensin II-induced but not catecholamine-induced hypertension. Circulation 1997, 95, 588-593.

(145) Reckelhoff, J. F.; Zhang, H.; Srivastava, K.; Roberts, L. J., II; Morrow, J. D.; Romero, J. C.: Subpressor doses of angiotensin II increase plasma F2-isoprostanes in rats. Hypertension 2000, 35, 476-479.

(146) Beard, J. L.; Connor, J. R.; Jones, B. C.: Iron in the brain. Nutr Rev 1993, 51, 157-70.

(147) Butterfield, D. A.; Castegna, A.; Lauderback Christopher, M.; Drake, J.: Evidence that amyloid beta-peptide-induced lipid peroxidation and its sequelae in Alzheimer's disease brain contribute to neuronal death. Neurobiol Aging 2002, 23, 655-64.

(148) Lyras, L.; Cairns, N. J.; Jenner, A.; Jenner, P.; Halliwell, B.: An assessment of oxidative damage to proteins, lipids, and DNA in brain from patients with Alzheimer's disease. J. Neurochem. 1997, 68, 2061-2069.

(149) Lovell, M. A.; Ehmann, W. D.; Mattson, M. P.; Markesbery, W. R.: Elevated 4-Hydroxynonenal in ventricular fluid in Alzheimer's disease. Neurobiol. Aging 1997, 18, 457-461.

(150) McCarron, M.; Gill, M.; McCallion, P.; Begley, C.: Health co-morbidities in ageing persons with Down syndrome and Alzheimer's dementia. J Intellect Disabil Res 2005, 49, 560-6.

(151) Elroy-Stein, O.; Bernstein, Y.; Groner, Y.: Overproduction of human copper/zinc-superoxide dismutase in transfected cells: extenuation of paraquat-mediated cytotoxicity and enhancement of lipid peroxidation. Embo J. 1986, 5, 615-22.

(152) Tretter, L.; Sipos, I.; Adam-Vizi, V.: Initiation of neuronal damage by complex I deficiency and oxidative stress in Parkinson's Disease. Neurochem. Res. 2004, 29, 569-577.

(153) Tu, P.-H.; Gurney, M. E.; Julien, J.-P.; Lee, V. M. Y.; Trojanowski, J. Q.: Oxidative stress, mutant SOD1, and neurofilament pathology in transgenic mouse models of human motor neuron disease. Lab. Invest. 1997, 76, 441-456.

(154) Rosen, D. R.; Siddique, T.; Patterson, D.; Figlewicz, D. A.; Sapp, P.; Hentati, A.; Donaldson, D.; Goto, J.; O'Regan, J. P.; et al.: Mutations in copper/zinc superoxide dismutase gene are associated with familial amyotrophic lateral sclerosis. Nature (London) 1993, 362, 59-62.

(155) Beckman, J. S.: Oxidative Damage and Tyrosine Nitration from Peroxynitrite. Chem. Res. Toxicol. 1996, 9, 836-844.

(156) Liu, R.; Althaus, J. S.; Ellerbrock, B. R.; Becker, D. A.; Gurney, M. E.: Enhanced oxygen radical production in a transgenic mouse model of familial amyotrophic lateral sclerosis. Ann. Neurol. 1998, 44, 763-770.

(157) Deng, H.-X.; Chen, W.; Hong, S.-T.; Boycott, K. M.; Gorrie, G. H.; Siddique, N.; Yang, Y.; Fecto, F.; Shi, Y.; Zhai, H.; Jiang, H.; Hirano, M.; Rampersaud, E.; Jansen, G. H.; Donkervoort, S.; Bigio, E. H.; Brooks, B. R.; Ajroud, K.; Sufit, R. L.; Haines, J. L.; Mugnaini, E.; Pericak-Vance, M. A.; Siddique, T.: Mutations in UBQLN2 cause dominant X-linked juvenile and adult-onset ALS and ALS/dementia. Nature (London, U. K.) 2011, 477, 211-215.

(158) Chen, C.-M.; Wu, Y.-R.; Cheng, M.-L.; Liu, J.-L.; Lee, Y.-M.; Lee, P.-W.; Soong, B.-W.; Chiu, D. T.-Y.: Increased oxidative damage and mitochondrial abnormalities in the peripheral blood of Huntington's disease patients. Biochem. Biophys. Res. Commun. 2007, 359, 335-340.

(159) Bagasra, O.; Michaels, F. H.; Zheng, Y. M.; Bobroski, L. E.; Spitsin, S. V.; Fu, Z. F.; Tawadros, R.; Koprowski, H.: Activation of the inducible form of nitric oxide synthase in the brains of patients with multiple sclerosis. Proc. Natl. Acad. Sci. U.S.A. 1995, 92, 12041-5.

(160) Wei, H.; Kim, S.-J.; Zhang, Z.; Tsai, P.-C.; Wisniewski, K. E.; Mukherjee, A. B.: ER and oxidative stresses are common mediators of apoptosis in both neurodegenerative and non-neurodegenerative lysosomal storage disorders and are alleviated by chemical chaperones. Hum. Mol. Genet. 2008, 17, 469-477.

(161) Sparaco, M.; Gaeta, L. M.; Santorelli, F. M.; Passarelli, C.; Tozzi, G.; Bertini, E.; Simonati, A.; Scaravilli, F.; Taroni, F.; Duyckaerts, C.; Feleppa, M.; Piemonte, F.: Friedreich's ataxia: Oxidative stress and cytoskeletal abnormalities. Journal of the Neurological Sciences 2009, 287, 111-118.

(162) Gersh, B. J.: Current issues in reperfusion therapy. Am J Cardiol 1998, 82, 3P-11P.

(163) Katz, A.; Oldham, K. T.; Guice, K. S.; Coran, A. G.: Reperfusion injury following single-lung transplantation: The tissue glutathione response. Journal of Pediatric Surgery 1993, 28, 1301-1306.

(164) Goode, H. F.; Webster, N. R.; Howdle, P. D.; Leek, J. P.; Lodge, J. P.; Sadek, S. A.; Walker, B. E.: Reperfusion injury, antioxidants and hemodynamics during orthotopic liver transplantation. Hepatology 1994, 19, 354-9.

(165) Chamoun, F.; Burne, M.; O'Donnell, M.; Rabb, H.: Pathophysiologic role of selectins and their ligands in ischemia reperfusion injury. Front. Biosci. 2000, 5, E103-E109.

(166) Downey, J. M.: Free radicals and their involvement during long-term myocardial ischemia and reperfusion. Annu. Rev. Physiol. 1990, 52, 487-504.

(167) Granger, D. N.: Role of xanthine oxidase and granulocytes in ischemia-reperfusion injury. Am J Physiol 1988, 255, H1269-75.

(168) Salvemini, D.; Wang, Z.-Q.; Zweier, J. L.; Samouilov, A.; MacArthur, H.; Misko, T. P.; Currie, M. G.; Cuzzocrea, (168) [continued] S.; Sikorski, J. A.; Riley, D. P.: A nonpeptidyl mimic of superoxide dismutase with therapeutic activity in rats. Science (Washington, D.C.) 1999, 286, 304-306.

(169) Young, T.; Palta, M.; Dempsey, J.; Skatrud, J.; Weber, S.; Badr, S.: The occurrence of sleep-disordered breathing among middle-aged adults. N Engl J Med 1993, 328, 1230-5.

(170) Shepard, J. W., Jr.: Hypertension, cardiac arrhythmias, myocardial infarction, and stroke in relation to obstructive sleep apnea. Clin Chest Med 1992, 13, 437-58.

(171) He, J.; Kryger, M. H.; Zorick, F. J.; Conway, W.; Roth, T.: Mortality and apnea index in obstructive sleep apnea. Experience in 385 male patients. Chest 1988, 94, 9-14.

(172) Schulz, R.; Mahmoudi, S.; Hattar, K.; Sibelius, U.; Olschewski, H.; Mayer, K.; Seeger, W.; Grimminger, F.: Enhanced release of superoxide from polymorphonuclear neutrophils in obstructive sleep apnea. Impact of continuous positive airway pressure therapy. Am J Respir Crit. Care Med 2000, 162, 566-70.

(173) Adachi, H.; Fujiwara, Y.; Ishii, N.: Effects of oxygen on protein carbonyl and aging in *Caenorhabditis elegans* mutants with long (age-1) and short (mev-1) life spans. J Gerontol A Biol Sci Med Sci 1998, 53, B240-4.

(174) Dillard, C. J.; Tappel, A. L.: Fluorescent damage products of lipid peroxidation. Methods Enzymol. 1984, 105, 337-41.

(175) Fraga, C. G.; Shigenaga, M. K.; Park, J. W.; Degan, P.; Ames, B. N.: Oxidative damage to DNA during aging: 8-hydroxy-2'-deoxyguanosine in rat organ DNA and urine. Proc. Natl. Acad. Sci. U.S.A. 1990, 87, 4533-7.

(176) Cadenas, E.; Davies, K. J. A.: Mitochondrial free radical generation, oxidative stress, and aging. Free Radical Biol. Med. 2000, 29, 222-230.

(177) Poli, G.; Leonarduzzi, G.; Biasi, F.; Chiarpotto, E.: Oxidative stress and cell signaling. Curr. Med. Chem. 2004, 11, 1163-1182.

(178) Thannickal, V. J.; Fanburg, B. L.: Reactive oxygen species in cell signaling. Am J Physiol Lung Cell Mol Physiol 2000, 279, L1005-28.

(179) Finkel, T.: Oxygen radicals and signaling. Curr. Opin. Cell Biol. 1998, 10, 248-253.

(180) Lowenstein, C. J.; Dinerman, J. L.; Snyder, S. H.: Nitric oxide: a physiologic messenger. Ann Intern Med 1994, 120, 227-37.

(181) Barrett, W. C.; DeGnore, J. P.; Koenig, S.; Fales, H. M.; Keng, Y.-F.; Zhang, Z.-Y.; Yim, M. B.; Chock, P. B.: Regulation of PTP1B via Glutathionylation of the Active Site Cysteine 215. Biochemistry 1999, 38, 6699-6705.

(182) Ignarro, L. J.; Kadowitz, P. J.: The pharmacological and physiological role of cyclic GMP in vascular smooth muscle relaxation. Annu Rev Pharmacol Toxicol 1985, 25, 171-91.

(183) Bunn, H. F.; Poyton, R. O.: Oxygen sensing and molecular adaptation to hypoxia. Physiol. Rev. 1996, 76, 839-885.

(184) Anderson, T.; Vanden Hoek Terry, L.: Preconditioning and the oxidants of sudden death. Curr Opin Crit. Care 2003, 9, 194-8.

(185) Burda, J.; Danielisova, V.; Gottlieb, M.; Nemethova, M.; Matiasova, M.; Kravcukova, P.; Domorakova, I.; Dankova, M.; Mechirova, E.: Mechanisms of ischemic tolerance acquisition: the role of nitric oxide. NO-cGMP Signaling Spinal Cord Brain Stem Circuitry 2009, 1-10.

(186) Chalfont, G. R.; Perkins, M. J.; Horsfield, A.: Probe for homolytic reactions in solution. II. Polymerization of styrene. J. Amer. Chem. Soc. 1968, 90, 7141-2.

(187) Hensley, K.; Robinson, K. A.; Gabbita, S. P.; Salsman, S.; Floyd, R. A.: Reactive oxygen species, cell signaling, and cell injury. Free Radical Biol. Med. 2000, 28, 1456-1462.

(188) Chapter 3 The detection and characterization of free radical species. In Laboratory Techniques in Biochemistry and Molecular Biology; Catherine A. Rice-Evans, A. T. D. a. M. C. R. S., Ed.; Elsevier, 1991; Vol. Volume 22; pp 51-100.

(189) Berliner, L. J.; Eaton, G. R.; Eaton, S. S.; Editors: Distance Measurements in Biological Systems by EPR. [In: Biol. Magn. Reson., 2000; 19], 2000.

(190) Adrian, F. J.; Cochran, E. L.; Bowers, V. A.: Electron spin resonance spectrum of HO2 in argon at 4.2° K. J. Chem. Phys. 1967, 47, 5441-2.

(191) Saito, E.; Bielski, B. H. J.: Electron paramagnetic resonance spectrum of the HO2 radical in aqueous solution. J. Am. Chem. Soc. 1961, 83, 4467-8.

(192) Meisel, D.; Levanon, H.; Czapski, G.: Hydroperoxyl radical reactions. II. Cupric ions in modulated photolysis. Electron paramagnetic resonance experiments. J. Phys. Chem. 1974, 78, 779-82.

(193) Rehorek, D.; Hennig, H.: Spin trapping in photochemistry of coordination compounds. Can. J. Chem. 1982, 60, 1565-73.

(194) Pfeiffer, P.; Braude, S.; Fritsch, R.; Halberstadt, W.; Kirchhoff, G.; Kleber, J.; Wittkop, P.: Photochemical syntheses of indole derivatives. Justus Liebigs Ann. Chem. 1916, 411, 72-158.

(195) Smith, L. I.: Aliphatic diazo compounds, nitrones, and structurally analogous compounds. Systems capable of undergoing 1,3-additions. Chem. Rev. 1938, 23, 193-285.

(196) Hamer, J.; Macaluso, A.: Nitrones. Chem. Rev. 1964, 64, 473-95.

(197) Lombardo, M.; Trombini, C.: Nucleophilic additions to nitrones. Synthesis 2000, 759-774.

(198) Gothelf, K. V.; Jorgensen, K. A.: Catalytic enantioselective 1,3-dipolar cycloaddition reactions of nitrones. Chem. Commun. (Cambridge) 2000, 1449-1458.

(199) Torssell, K. B. G.: Nitrile Oxides, Nitrones, and Nitronates in Organic Synthesis. Novel Strategies in Synthesis, 1988.

(200) Novelli, G. P.; Angiolini, P.; Tani, R.: Spin trap phenyl butyl nitrone prevents lethal shock in the rat. Free Radicals Liver Inj., Proc. Int. Meet., 1st 1985, 225-8.

(201) Becker, D. A.: Diagnostic and therapeutic applications of azulenyl nitrone spin traps. Cell. Mol. Life. Sci. 1999, 56, 626-633.

(202) Janzen, E. G.; Coulter, G. A.: Spin trapping in SDS micelles. J. Am. Chem. Soc. 1984, 106, 1962-8.

(203) Becker, D. A.: Highly sensitive colorimetric detection and facile isolation of diamagnetic free radical adducts of novel chromotropic nitrone spin trapping agents readily derived from guaiazulene. Book of Abstracts, 211th ACS National Meeting, New Orleans, La., Mar. 24-28 1996, ORGN-426.

(204) Klivenyi, P.; Matthews, R. T.; Wermer, M.; Yang, L.; MacGarvey, U.; Becker, D. A.; Natero, R.; Beal, M. F.: Azulenyl nitrone spin traps protect against MPTP neurotoxicity. Exp. Neurol. 1998, 152, 163-166.

(205) Becker, D. A.; Ley, J. J.; Echegoyen, L.; Alvarado, R.: Stilbazulenyl Nitrone (STAZN): A Nitronyl-Substituted Hydrocarbon with the Potency of Classical Phenolic Chain-Breaking Antioxidants. J. Am. Chem. Soc. 2002, 124, 4678-4684.

(206) Lapchak, P. A.; Schubert, D. R.; Maher, P. A.: De-Risking of Stilbazulenyl Nitrone (STAZN), a Lipophilic Nitrone to Treat Stroke Using a Unique Panel of In Vitro Assays. Transl. Stroke Res. 2011, 2, 209-217.
(207) Ley, J. J.; Prado, R.; Wei, J. Q.; Bishopric, N. H.; Becker, D. A.; Ginsberg, M. D.: Neuroprotective antioxidant STAZN protects against myocardial ischemia/reperfusion injury. Biochem. Pharmacol. 2008, 75, 448-456.
(208) Tawadros, P. S.; Powers, K. A.; Yang, I.; Becker, D. A.; Ginsberg, M. D.; Szaszi, K.; Kapus, A.; Rotstein, O. D.: Stilbazulenyl nitrone decreases oxidative stress and reduces lung injury after hemorrhagic shock/resuscitation and LPS. Antioxid Redox Signal 2007, 9, 1971-7.
(209) Belayev, L.; Becker, D. A.; Alonso, O. F.; Liu, Y.; Busto, R.; Ley, J. J.; Ginsberg, M. D.: Stilbazulenyl nitrone, a novel azulenyl nitrone antioxidant: improved neurological deficit and reduced contusion size after traumatic brain injury in rats. J. Neurosurg. 2002, 96, 1077-1083.
(210) Ley James, J.; Vigdorchik, A.; Belayev, L.; Zhao, W.; Busto, R.; Khoutorova, L.; Becker David, A.; Ginsberg Myron, D.: Stilbazulenyl nitrone, a second-generation azulenyl nitrone antioxidant, confers enduring neuroprotection in experimental focal cerebral ischemia in the rat: neurobehavior, histopathology, and pharmacokinetics. J Pharmacol Exp Ther 2005, 313, 1090-100.
(211) Goldstein, S.; Lestage, P.: Chemical and pharmacological aspects of heteroarylnitrones. Curr. Med. Chem. 2000, 7, 1255-1267.
(212) Goto, G.; Kawakita, K.; Okutani, T.; Miki, T.: An improved synthesis of N-hydroxy amino acids and their esters using (Z)-2-furaldehyde oxime. Chem. Pharm. Bull. 1986, 34, 3202-7.
(213) Giner-Sorolla, A.; Zimmerman, I.; Bendich, A.: Synthesis of purine-6-carboxaldehyde and related derivatives. J. Am. Chem. Soc. 1959, 81, 2515-21.
(214) Brown, R. F. C.; Clark, V. M.; Todd, A. R.: Δ1-Pyrroline N-oxides. Proc. Chem. Soc., London 1957, 97-8.
(215) Zhao, H.; Joseph, J.; Zhang, H.; Karoui, H.; Kalyanaraman, B.: Synthesis and biochemical applications of a solid cyclic nitrone spin trap: a relatively superior trap for detecting superoxide anions and glutathiyl radicals. Free Radical Biol. Med. 2001, 31, 599-606.
(216) Zhang, H.; Joseph, J.; Vasquez-Vivar, J.; Karoui, H.; Nsanzumuhire, C.; Martasek, P.; Tordo, P.; Kalyanaraman, B.: Detection of superoxide anion using an isotopically labeled nitrone spin trap: potential biological applications. FEBS Lett. 2000, 473, 58-62.
(217) Chalier, F.; Hardy, M.; Ouari, O.; Rockenbauer, A.; Tordo, P.: Design of New Derivatives of Nitrone DEPMPO Functionalized at C-4 for Further Specific Applications in Superoxide Radical Detection. J. Org. Chem. 2007, 72, 7886-7892.
(218) Bernotas, R. C.; Thomas, C. E.; Carr, A. A.; Nieduzak, T. R.; Adams, G.; Ohlweiler, D. F.; Hay, D. A.: Synthesis and radical scavenging activity of 3,3-dialkyl-3,4-dihydroisoquinoline 2-oxides. Bioorg. Med. Chem. Lett. 1996, 6, 1105-1110.
(219) Bernotas, R. C.; Adams, G.; Carr, A. A.: Synthesis of benzazepine-based nitrones as radical traps. Tetrahedron 1996, 52, 6519-6526.
(220) Dage, J. L.; Ackermann, B. L.; Barbuch, R. J.; Bernotas, R. C.; Ohlweiler, D. F.; Haegele, K. D.; Thomas, C. E.: Evidence for a novel pentyl radical adduct of the cyclic nitrone spin trap MDL 101,002. Free Radical Biol. Med. 1997, 22, 807-812.
(221) Dehnel, A.; Griller, D.; Kanabus-Kaminska, J. M.: Designer spin traps with a cyclic nitrone structure. J. Org. Chem. 1988, 53, 1566-7.
(222) Finkelstein, E.; Rosen, G. M.; Rauckman, E. J.; Paxton, J.: Spin trapping of superoxide. Mol. Pharmacol. 1979, 16, 676-85.
(223) Janzen, E. G.; Nutter, D. E., Jr.; Davis, E. R.; Blackburn, B. J.; Poyer, J. L.; McCay, P. B.: On spin trapping hydroxyl and hydroperoxy radicals. Can. J. Chem. 1978, 56, 2237-42.
(224) Roubaud, V.; Lauricella, R.; Tuccio, B.; Bouteiller, J.-C.; Tordo, P.: Decay of superoxide spin adducts of new PBN-type phosphorylated nitrones. Res. Chem. Intermed. 1996, 22, 405-416.
(225) Karoui, H.; Tordo, P.: ESR-spin trapping in the presence of cyclodextrins. Detection of PBN-superoxide spin adduct. Tetrahedron Letters 2004, 45, 1043-1045.
(226) Rizzi, C.; Marque, S.; Belin, F.; Bouteiller, J.-C.; Lauricella, R.; Tuccio, B.; Cerri, V.; Tordo, P.: PPN-type nitrones: preparation and use of a new series of 13-phosphorylated spin-trapping agents. J. Chem. Soc., Perkin Trans. 2 1997, 2513-2518.
(227) Allouch, A.; Roubaud, V.; Lauricella, R.; Bouteiller, J.-C.; Tuccio, B.: Spin trapping of superoxide by diesternitrones. Org. Biomol. Chem. 2005, 3, 2458-2462.
(228) Lauricella, R.; Allouch, A.; Roubaud, V.; Bouteiller, J.-C.; Tuccio, B.: A new kinetic approach to the evaluation of rate constants for the spin trapping of superoxide/hydroperoxyl radical by nitrones in aqueous media. Org. Biomol. Chem. 2004, 2, 1304-1309.
(229) Bonnett, R.; Brown, R. F. C.; Clark, V. M.; Sutherland, I. O.; Todd, A.: Experiments towards the synthesis of corrins. II. Preparation and reactions of 1-pyrroline 1-oxides. J. Chem. Soc. 1959, 2094-2102.
(230) Iwamura, M.; Inamoto, N.: Novel formation of nitroxide radicals by radical addition to nitrones. Bull. Chem. Soc. Jpn. 1967, 40, 703.
(231) Janzen, E. G.; Evans, C. A.: Rate constants for spin trapping tert-butoxy radicals as studied by electron spin resonance. J. Am. Chem. Soc. 1973, 95, 8205.
(232) Harbour, J. R.; Chow, V.; Bolton, J. R.: Electron spin resonance study of the spin adducts of hydroxy and hydrogen dioxide radicals with nitrones in the ultraviolet photolysis of aqueous hydrogen peroxide solutions. Can. J. Chem. 1974, 52, 3549-53.
(233) Finkelstein, E.; Rosen, G. M.; Rauckman, E. J.: Spin trapping of superoxide and hydroxyl radical: Practical aspects. Archives of Biochemistry and Biophysics 1980, 200, 1-16.
(234) Buettner, G. R.; Oberley, L. M.: Considerations in the spin trapping of superoxide and hydroxyl radical in aqueous systems using 5,5-dimethyl-1-pyrroline-1-oxide. Biochem. Biophys. Res. Commun. 1978, 83, 69-74.
(235) Dupeyre, R. M.; Rassat, A.: Nitroxides. XIX. Norpseudopelletierine-N-oxyl, a new, stable, unhindered free radical. J. Am. Chem. Soc. 1966, 88, 3180-1.
(236) Pou, S.; Hassett, D. J.; Britigan, B. E.; Cohen, M. S.; Rosen, G. M.: Problems associated with spin trapping oxygen-centered free radicals in biological systems. Analytical Biochemistry 1989, 177, 1-6.
(237) Britigan, B. E.; Rosen, G. M.; Chai, Y.; Cohen, M. S.: Do human neutrophils make hydroxyl radical? Determination of free radicals generated by human neutrophils activated with a soluble or particulate stimulus using electron paramagnetic resonance spectrometry. J. Biol. Chem. 1986, 261, 4426-31.
(238) Frejaville, C.; Karoui, H.; Tuccio, B.; Moigne, F. L.; Culcasi, M.; Pietri, S.; Lauricella, R.; Tordo, P.: 5-(Diethoxyphosphoryl)-5-methyl-1-pyrroline N-oxide: A New Efficient Phosphorylated Nitrone for the in Vitro and in Vivo Spin Trapping of Oxygen-Centered Radicals. J. Med. Chem. 1995, 38, 258-65.
(239) Chalier, F.; Tordo, P.: 5-Diisopropoxyphosphoryl-5-methyl-1-pyrroline N-oxide, DIPPMPO, a crystalline analog of the nitrone DEPMPO: synthesis and spin trapping properties. J. Chem. Soc., Perkin Trans. 2 2002, 2110-2117.
(240) Frejaville, C.; Karoui, H.; Tuccio, B.; le Moigne, F.; Culcasi, M.; Pietri, S.; Lauricella, R.; Tordo, P.: 5-Diethoxyphosphoryl-5-methyl-1-pyrroline N-oxide (DEPMPO): a new phosphorylated nitrone for the efficient in vitro and in vivo spin trapping of oxygen-centered radicals. J. Chem. Soc., Chem. Commun. 1994, 1793-4.
(241) Olive, G.; Mercier, A.; Le Moigne, F.; Rockenbauer, A.; Tordo, P.: 2-Ethoxycarbonyl-2-methyl-3,4-dihydro-2H-pyrrole-1-oxide: evaluation of the spin trapping properties. Free Radical Biol. Med. 2000, 28, 403-408.
(242) Hoffmann, A. K.; Henderson, A. T.: A new stable free radical: di-tert-Butylnitroxide. J. Am. Chem. Soc. 1961, 83, 4671.
(243) Keszler, A.; Kalyanaraman, B.; Hogg, N.: Comparative investigation of superoxide trapping by cyclic nitrone spin traps: the use of singular value decomposition and multiple linear regression analysis. Free Radical Biology and Medicine 2003, 35, 1149-1157.
(244) Totter, J. R.; de Dugros, E. C.; Riveiro, C.: Use of chemiluminescent compounds as possible indicators of radical production during xanthine oxidase action. J. Biol. Chem. 1960, 235, 1839-42.
(245) Greenlee, L.; Fridovich, I.; Handler, P.: Chemiluminescence induced by operation of iron-flavo-proteins. Biochemistry 1962, 1, 779-83.
(246) Omar, H. A.; Chemy, P. D.; Mortelliti, M. P.; Burke-Wolin, T.; Wolin, M. S.: Inhibition of coronary artery superoxide dismutase attenuates endothelium-dependent and -independent nitrovasodilator relaxation. Circ. Res. 1991, 69, 601-8.
(247) Gyllenhammar, H.: Lucigenin chemiluminescence in the assessment of neutrophil superoxide production. Journal of Immunological Methods 1987, 97, 209-213.
(248) Morawietz, H.; Weber, M.; Rueckschloss, U.; Lauer, N.; Hacker, A.; Kojda, G.: Upregulation of Vascular NAD (P)H Oxidase Subunit gp91phox and Impairment of the Nitric Oxide Signal Transduction Pathway in Hypertension. Biochemical and Biophysical Research Communications 2001, 285, 1130-1135.
(249) Hink, U.; Mollnau, H.; Oelze, M.; Matheis, E.; Hartmann, M.; Skatchkov, M.; Thaiss, F.; Stahl, R. A. K.; Warnholtz, A.; Meinertz, T.; Griendling, K.; Harrison, D. G.; Forstermann, U.; Munzel, T.; Li, H.: Mechanisms underlying endothelial dysfunction in diabetes mellitus. Circ. Res. 2001, 88, e14-e22.
(250) Ohara, Y.; Peterson, T. E.; Harrison, D. G.: Hypercholesterolemia increases endothelial superoxide anion production. J. Clin. Invest. 1993, 91, 2546-51.
(251) Rembish, S. J.; Trush, M. A.: Further evidence that lucigenin-derived chemiluminescence monitors mitochondrial superoxide generation in rat alveolar macrophages. Free Radical Biology and Medicine 1994, 17, 117-126.
(252) Nakano, M.; Sugioka, K.; Ushijima, Y.; Goto, T.: Chemiluminescence probe with Cypridina luciferin analog, 2-methyl-6-phenyl-3,7-dihydroimidazo[1,2-a]pyrazin-3-one, for estimating the ability of human granulocytes to generate $O_2$. Analytical Biochemistry 1986, 159, 363-369.
(253) Kambayashi, Y.; Ogino, K.: Reestimation of Cypridina luciferin analogs (MCLA) as a chemiluminescence probe to detect active oxygen species: cautionary note for use of MCLA. J. Toxicol. Sci. 2003, 28, 139-148.
(254) Faulkner, K.; Fridovich, I.: Luminol and lucigenin as detectors for O2s[combining dot above]. Free Radical Biology and Medicine 1993, 15, 447-451.
(255) Li, Y.; Zhu, H.; Kuppusamy, P.; Roubaud, V.; Zweier, J. L.; Trush, M. A.: Validation of lucigenin (bis-N-methylacridinium) as a chemilumigenic probe for detecting superoxide anion radical production by enzymic and cellular systems. J. Biol. Chem. 1998, 273, 2015-2023.
(256) Zielonka, J.; Srinivasan, S.; Hardy, M.; Ouari, 0.; Lopez, M.; Vasquez-Vivar, J.; Avadhani, N. G.; Kalyanaraman, B.: Cytochrome c-mediated oxidation of hydroethidine and mito-hydroethidine in mitochondria: Identification of homo- and heterodimers. Free Radical Biol. Med. 2008, 44, 835-846.
(257) Saiki, I.; Bucana, C. D.; Tsao, J. Y.; Fidler, I. J.: Quantitative fluorescent microassay for identification of antiproliferative compounds. JNCI, J. Natl. Cancer Inst. 1986, 77, 1235-40.
(258) Zhao, H.; Kalivendi, S.; Zhang, H.; Joseph, J.; Nithipatikom, K.; Vasquez-Vivar, J.; Kalyanaraman, B.: Superoxide reacts with hydroethidine but forms a fluorescent product that is distinctly different from ethidium: potential implications in intracellular fluorescence detection of superoxide. Free Radical Biology and Medicine 2003, 34, 1359-1368.
(259) Sorescu, D.; Weiss, D.; Lassegue, B.; Clempus, R. E.; Szocs, K.; Sorescu, G. P.; Valppu, L.; Quinn, M. T.; Lambeth, J. D.; Vega, J. D.; Taylor, R.; Griendling, K. K.: Superoxide production and expression of Nox family proteins in human atherosclerosis. Circulation 2002, 105, 1429-1435.
(260) Zielonka, J.; Hardy, M.; Kalyanaraman, B.: HPLC study of oxidation products of hydroethidine in chemical and biological systems: ramifications in superoxide measurements. Free Radical Biology and Medicine 2009, 46, 329-338.
(261) Papapostolou, I.; Patsoukis, N.; Georgiou, C. D.: The fluorescence detection of superoxide radical using hydroethidine could be complicated by the presence of heme proteins. Analytical Biochemistry 2004, 332, 290-298.
(262) Carter, W. O.; Narayanan, P. K.; Robinson, J. P.: Intracellular hydrogen peroxide and superoxide anion detection in endothelial cells. J. Leukocyte Biol. 1994, 55, 253-8.
(263) Bindokas, V. P.; Jordan, J.; Lee, C. C.; Miller, R. J.: Superoxide production in rat hippocampal neurons: selective imaging with hydroethidine. J. Neurosci. 1996, 16, 1324-36.
(264) Palazzolo-Ballance, A. M.; Suquet, C.; Hurst, J. K.: Pathways for Intracellular Generation of Oxidants and Tyrosine Nitration by a Macrophage Cell Line. Biochemistry 2007, 46, 7536-7548.
(265) Fernandes Denise, C.; Wosniak, J., Jr.; Pescatore Luciana, A.; Bertoline Maria, A.; Liberman, M.; Laurindo Francisco, R. M.; Santos Celio, X. C.: Analysis of DHE-derived oxidation products by HPLC in the assessment of superoxide production and NADPH oxidase activity in vascular systems. Am J Physiol Cell Physiol 2007, 292, C413-22.
(266) Vanden Hoek, T. L.; Li, C.; Shao, Z.; Schumacker, P. T.; Becker, L. B.: Significant Levels of Oxidants are Generated by Isolated Cardiomyocytes During Ischemia Prior to Reperfusion. Journal of Molecular and Cellular Cardiology 1997, 29, 2571-2583.

(267) Zielonka, J.; Sarna, T.; Roberts, J. E.; Wishart, J. F.; Kalyanaraman, B.: Pulse radiolysis and steady-state analyses of the reaction between hydroethidine and superoxide and other oxidants. Archives of Biochemistry and Biophysics 2006, 456, 39-47.

(268) Bilski, P. J.; Karriker, B.; Chignell, C. F.: Quenching and generation of singlet oxygen by hydroethidine and related chromophores. Chem. Phys. Lett. 2009, 475, 116-119.

(269) Zielonka, J.; Vasquez-Vivar, J.; Kalyanaraman, B.: The confounding effects of light, sonication, and Mn(III)TBAP on quantitation of superoxide using hydroethidine. Free Radical Biol. Med. 2006, 41, 1050-1057.

(270) Zielonka, J.; Vasquez-Vivar, J.; Kalyanaraman, B.: Detection of 2-hydroxyethidium in cellular systems: a unique marker product of superoxide and hydroethidine. Nat. Protoc. 2008, 3, 8-21.

(271) Fredriksson, A.; Eriksson, P.; Archer, T.: MPTP-induced deficits in motor activity: neuroprotective effects of the spin-trapping agent, α-phenyl-tert-butyl-nitrone (PBN). J. Neural Transm. 1997, 104, 579-592.

(272) Klein, J.; Becker, J. Y.: Metallation reactions. XIV. Generality of the 1,3-sigmatropic shift of hydrogen in allenyllithium compounds. Tetrahedron 1972, 28, 5385-92.

(273) Becker, D. A.; Danheiser, R. L.: A new synthesis of substituted azulenes. J. Am. Chem. Soc. 1989, 111, 389-91.

(274) Okajima, T.; Kurokawa, S.: Facile conversion of 1-methyl group of guaiazulene into 1-formyl group. Chem. Lett. 1997, 69-70.

(275) Chancel, F.: Bull. Soc. Chim 1894, 11.

(276) Campbell, K. N.; Sommers, A. H.; Campbell, B. K.: Preparation of unsymmetrical secondary aliphatic amines. J. Am. Chem. Soc. 1944, 66, 82-4.

(277) Tietze, L. F.; Neumann, T.; Kajino, M.; Pretor, M.: Efficient synthesis of branched propargyl- and allylsilanes. Synthesis 1995, 1003-6.

(278) Sabitha, G.; Reddy, B. V. S.; Babu, R. S.; Yadav, J. S.: LiCl catalyzed Knoevenagel condensation: comparative study of conventional method vs. microwave irradiation. Chem. Lett. 1998, 773-774.

(279) Smith, A. B., III; Kim, W.-S.; Wuest, W. M.: Ortho-TMS benzaldehyde: an effective linchpin for type II anion relay chemistry (ARC). Angew. Chem., Int. Ed. 2008, 47, 7082-7086.

(280) Tufariello, J. J.: Nitrones. 1,3 [One, Three]-Dipolar Cycloaddit. Chem. 1984, 2, 83-168.

(281) Houk, K. N.; Bimanand, A.; Mukherjee, D.; Sims, J.; Chang, Y.-M.; Kaufman, D. C.; Domelsmith, L. N.: Nitrone ionization potentials and cycloaddition regioselectivities. Heterocycles 1977, 7, 293-9.

(282) Huisgen, R.; Niklas, K.: The chemistry of an isolable azomethine ylide. Heterocycles 1984, 22, 21-6.

(283) Stokker, G.: Preparation of 1,2-benzisoxazoles from salicylaldoximes via trichloroacetyl isocyanate. J. Org. Chem. 1983, 48, 2613-15.

(284) Searcey, M.; Grewal, S. S.; Madeo, F.; Tsoungas, P. G.: A mild procedure for the production of secondary amines from oximes and benzisoxazoles. Tetrahedron Lett. 2003, 44, 6745-6747.

(285) Nair, V.; Vinod, A. U.: The reaction of cyclohexyl isocyanide and dimethyl acetylenedicarboxylate with aldehydes: a novel synthesis of 2-aminofuran derivatives. Chem. Commun. (Cambridge) 2000, 1019-1020.

(286) Yamada, S.-i.; Ninomiya, K.; Shioiri, T.: Transfer of the azido function from diphenylphosphoryl azide to malonic acid half esters. Tetrahedron Letters 1973, 14, 2343-2346.

(287) Fowler, J. S.: New synthesis of unsymmetrical azo compounds. J. Org. Chem. 1972, 37, 510-11.

(288) Ashburn, S. P.; Coates, R. M.: Generation and [3+2] cycloaddition reactions of oxazoline N-oxides. J. Org. Chem. 1984, 49, 3127-33.

(289) Huisgen, R.; Seidl, H.; Wulff, J.: 1,3-Dipolar cycloaddition. XLVII. Reactions of heteroaromatic amines oxide with carboxylic esters of the ethylene and acetylene series. Chem. Ber. 1969, 102, 915-25.

(290) Chiacchio, U.; Liguori, A.; Rescifina, A.; Romeo, G.; Rossano, F.; Sindona, G.; Uccella, N.: Novel approach to the ring-opening of 4-isoxazolines: one-pot synthesis of α,β-enones. Tetrahedron 1992, 48, 123-32.

(291) Chiacchio, U.; Casuscelli, F.; Liguori, A.; Rescifina, A.; Romeo, G.; Sindona, G.; Uccella, N.: Ring opening of 4-isoxazolines: competitive formation of enamino derivatives and α,β-enones. Heterocycles 1993, 36, 585-600.

(292) Chiacchio, U.; Rescifina, A.; Chiacchio, M. A.; Romeo, G.; Romeo, R.: New Rearrangement of 4-Isoxazoline System: Conversion of Ketones into α,β-Unsaturated Amides. J. Org. Chem. 2003, 68, 3718-3720.

(293) Anderson, A. G., Jr.; Replogle, L. L.: Electrophilic substitution of some 1,3-disubstituted azulenes. J. Org. Chem. 1963, 28, 2578-81.

(294) Luo, F.-T.; Wang, M.-W.; Wang, R. T.: Preparation of cyanoalkynes: 3-phenyl-2-propynenitrile. Org. Synth. 1998, 75, No pp given.

(295) Luo, F. T.; Wang, R. T.: A novel synthesis of cyanoalkynes via iodide-catalyzed cyanation of terminal acetylenes with cuprous cyanide. Tetrahedron Lett. 1993, 34, 5911-14.

(296) Thorand, S.; Krause, N.: Improved procedures for the palladium-catalyzed coupling of terminal alkynes with aryl bromides (Sonogashira coupling). J. Org. Chem. 1998, 63, 8551-8553.

(297) Ashok, K.; Scaria, P. M.; Kamat, P. V.; George, M. V.: Electron-transfer reactions. Reaction of nitrones with potassium. Can. J. Chem. 1987, 65, 2039-49.

(298) Tamao, K.; Hayashi, T.; Ito, Y.: Silafunctional compounds in organic synthesis. 45. An efficient oxidative cleavage of carbon-silicon bonds by a dioxygen/hydroquinone system. Tetrahedron Lett. 1989, 30, 6533-6.

(299) Tamao, K.; Hayashi, T.; Ito, Y.: Hydrogen peroxide oxidation of the silicon-carbon bond: mechanistic studies. Front. Organosilicon Chem., [Proc. Int. Symp. Organosilicon Chem.], 9th 1991, 197-207.

(300) Tamao, K.; Ishida, N.; Tanaka, T.; Kumada, M.: Silafunctional compounds in organic synthesis. Part 20. Hydrogen peroxide oxidation of the silicon-carbon bond in organoalkoxysilanes. Organometallics 1983, 2, 1694-6.

(301) Xu, Y.; Asghar, A.; Gray, J. I.; Pearson, A. M.; Haug, A.; Grulke, E. A.: ESR spin-trapping studies of free radicals generated by hydrogen peroxide activation of metmyoglobin. J. Agric. Food Chem. 1990, 38, 1494-7.

(302) Tamao, K.; Hayashi, T.; Ito, Y.: Structure and reactivity of hypercoordinate silicon compounds. Mechanism of hydrogen peroxide oxidation of silicon-carbon bonds. Nippon Kagaku Kaishi 1990, 509-15.

What is claimed is:

1. A compound having a structure of formula (I) or (II):

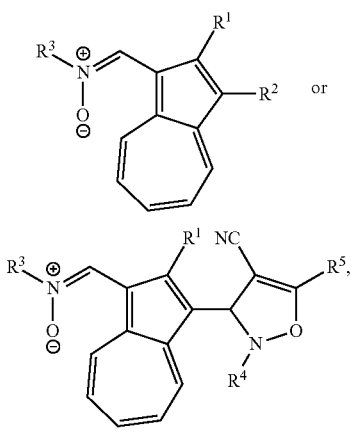

wherein
 R¹ is silyl;
 R² is CHO, alkyl, H, or —CH=N(O)—R⁶;
 R³ is alkyl, aryl, or heteroaryl;
 R⁴ is H or alkyl;
 R⁵ is alkyl, cycloalkyl, aryl, or heteroaryl, and
 R⁶ is alkyl;
or a salt, ester, hydrate or solvate thereof.

2. The compound of claim 1, wherein R¹ is Si(alkyl)₃.

3. The compound of claim 1, wherein R² is CHO or —CH=N(O)—R⁶.

4. The compound of claim 1, wherein R³ is t-butyl, methyl, ethyl, propyl, isopropyl, isobutyl, sec-butyl or n-butyl.

5. The compound of claim 1, wherein R⁴ is t-butyl, methyl, ethyl, propyl, isopropyl, isobutyl, sec-butyl or n-butyl.

6. The compound of claim 1, wherein R⁵ is t-butyl, methyl, ethyl, propyl, isopropyl, isobutyl, sec-butyl or n-butyl.

7. The compound of claim 1, wherein R⁵ is cycloalkyl.

8. The compound of claim 1, wherein R⁵ is

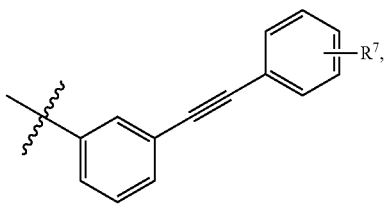

and R⁷ is H, alkyl, nitro, aryl, heteroaryl, -alkyleneP(aryl)₃, alkenylenearyl, —CH=N—NHC(O)alkyleneamino, —CH=N—NHC(O)alkyleneammonium, or —CH=N-guanidinyl.

9. The compound of claim 1 having a structure

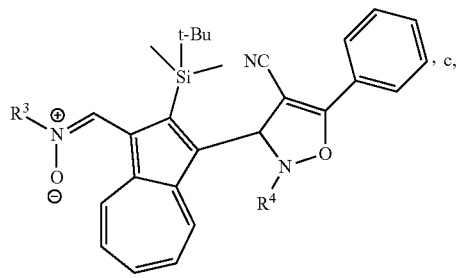

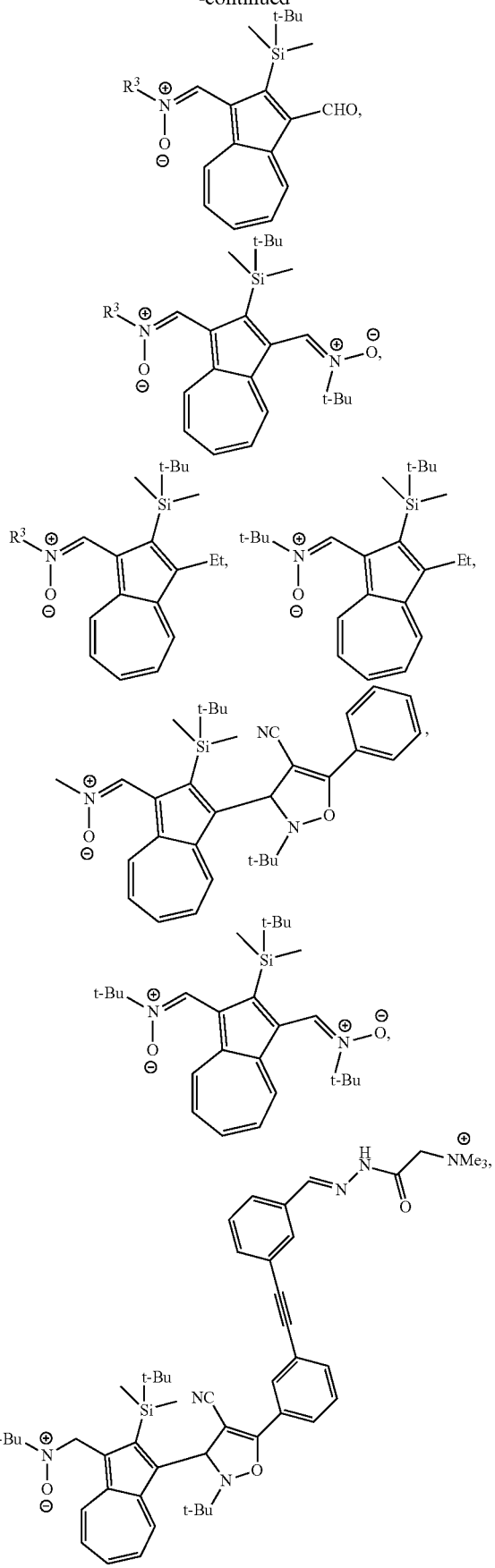

-continued

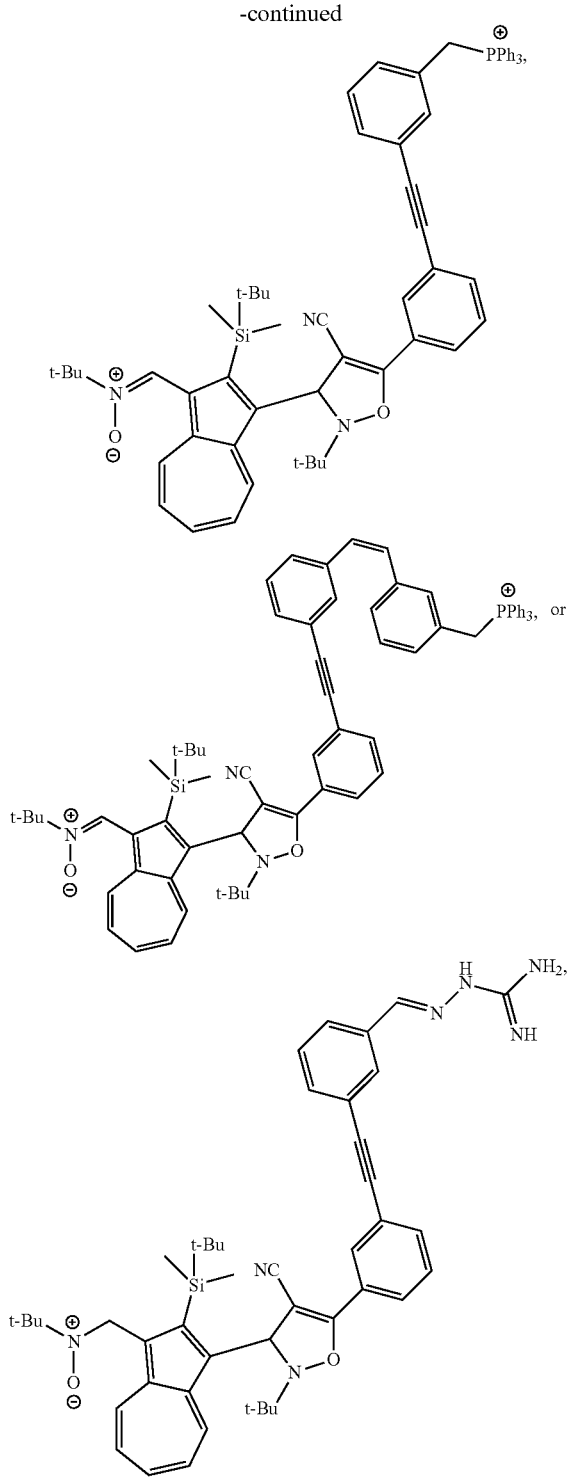

or a salt, ester, hydrate, or solvate thereof.

10. A method comprising contacting the compound of claim 1 with a superoxide ion.

11. The method of claim 10, wherein contacting is in vitro.

12. The method of claim 10, wherein contacting of the compound of claim 1 with the superoxide anion results in a color change, optionally detectable visually, via a change in UV-Vis absorbance, and/or via a change in fluorescence.

13. The method of claim 10, wherein contacting is in vivo.

14. The method of claim 13, further comprising administering the compound of any one of claims 1 to 9 to a subject suffering from a disease characterized by generation of superoxide.

15. The method of claim 14, wherein the disease is selected from pain including acute, inflammatory and neuropathic pain; chronic pain; dental pain; headache including migraine, cluster headache and tension headache; Parkinson's disease; Alzheimer's disease; multiple sclerosis; diseases and disorders mediated by or result in neuroinflammation, traumatic brain injury, stroke, or encephalitis; centrally-mediated neuropsychiatric diseases and disorders including depression, mania, bipolar disease, anxiety, schizophrenia, eating disorders, sleep disorders and cognition disorders; epilepsy and seizure disorders; prostate, bladder and bowel dysfunction, urinary incontinence, urinary hesitancy, rectal hypersensitivity, fecal incontinence, benign prostatic hypertrophy and inflammatory bowel disease; respiratory and airway disease and disorders including allergic rhinitis, asthma and reactive airway disease and chronic obstructive pulmonary disease; diseases and disorders mediated by or result in inflammation including arthritis, rheumatoid arthritis and osteoarthritis; myocardial infarction; autoimmune diseases and disorders; uveitis and atherosclerosis; itch/pruritus, psoriasis; alopecia (hair loss); obesity; lipid disorders; cancer; high blood pressure; spinal cord injury; irritable bowel syndrome; overactive bladder; or renal disorders.

16. A method of assaying a sample to diagnose for a condition associated with superoxide anion production comprising contacting the sample with a compound of claim 1, wherein the contacting produces a color change when the sample comprises a superoxide anion.

17. The method of claim 16, wherein the color change is detectable visually, via a change in absorbance as measured by UV-Vis spectrometry, by liquid chromatography, or via a change in fluorescence.

18. The method of claim 16, wherein the condition is selected from pain including acute, inflammatory and neuropathic pain; chronic pain; dental pain; headache including migraine, cluster headache and tension headache; Parkinson's disease; Alzheimer's disease; multiple sclerosis; diseases and disorders mediated by or result in neuroinflammation, traumatic brain injury, stroke, or encephalitis; centrally-mediated neuropsychiatric diseases and disorders including depression, mania, bipolar disease, anxiety, schizophrenia, eating disorders, sleep disorders and cognition disorders; epilepsy and seizure disorders; prostate, bladder and bowel dysfunction, urinary incontinence, urinary hesitancy, rectal hypersensitivity, fecal incontinence, benign prostatic hypertrophy and inflammatory bowel disease; respiratory and airway disease and disorders including allergic rhinitis, asthma and reactive airway disease and chronic obstructive pulmonary disease; diseases and disorders mediated by or result in inflammation including arthritis, rheumatoid arthritis and osteoarthritis; myocardial infarction; autoimmune diseases and disorders; uveitis and atherosclerosis; itch/pruritus, psoriasis; alopecia (hair loss); obesity; lipid disorders; cancer; high blood pressure; spinal cord injury; irritable bowel syndrome; overactive bladder; or renal disorders.

* * * * *

UNITED STATES PATENT AND TRADEMARK OFFICE
CERTIFICATE OF CORRECTION

PATENT NO. : 9,156,862 B2  
APPLICATION NO. : 14/353511  
DATED : October 13, 2015  
INVENTOR(S) : David A. Becker et al.

Page 1 of 2

It is certified that error appears in the above-identified patent and that said Letters Patent is hereby corrected as shown below:

On the Title Page, item 71:

"FLORDIA" should be -- FLORIDA --.

In the Claims:

At Column 71, lines 37-55, " 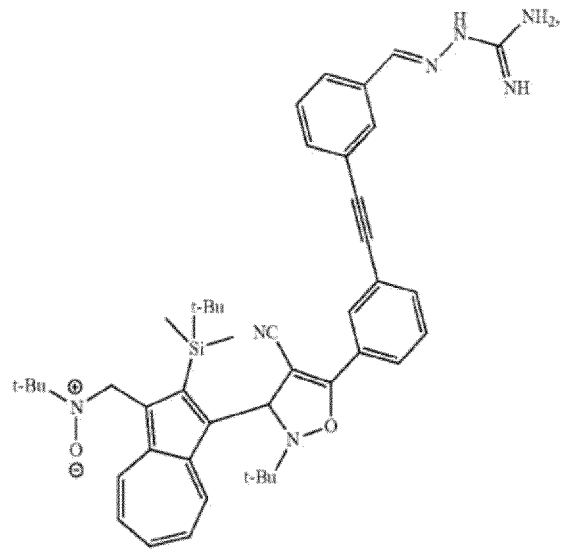 [SMILES: CC(C)(C)N1OC(c2cccc(C#Cc3cccc(/C=N/NC(=N)N)c3)c2)=C(C#N)C1c1c2cccccc-2c(C[NH+]([O-])C(C)(C)C)c1[Si](C)(C)C(C)(C)C] "

Signed and Sealed this  
Tenth Day of May, 2016

Michelle K. Lee  
*Director of the United States Patent and Trademark Office*

CERTIFICATE OF CORRECTION (continued)
U.S. Pat. No. 9,156,862 B2 should be --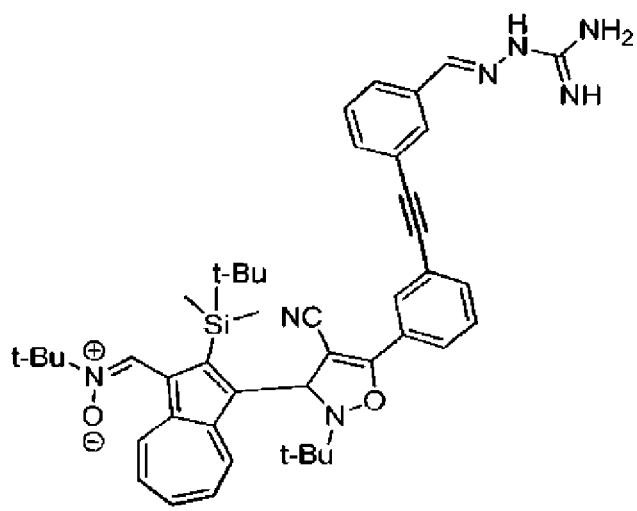,--.